(12) United States Patent
Ashoorzadeh et al.

(10) Patent No.: US 11,661,404 B2
(45) Date of Patent: May 30, 2023

(54) PRODRUG COMPOUNDS ACTIVATED BY AKR1C3 AND THEIR USE FOR TREATING HYPERPROLIFERATIVE DISORDERS

(71) Applicant: ACHILLES MEDICAL LIMITED, Auckland (NZ)

(72) Inventors: Amir Ashoorzadeh, Auckland (NZ); Christopher Paul Guise, Auckland (NZ); Adam Vorn Patterson, Auckland (NZ); Jeffrey Bruce Smaill, Auckland (NZ)

(73) Assignee: ACHILLES MEDICAL LIMITED, Auckland (NZ)

( * ) Notice: Subject to any disclaimer, the term of this patent is extended or adjusted under 35 U.S.C. 154(b) by 149 days.

(21) Appl. No.: 17/041,125

(22) PCT Filed: Mar. 25, 2019

(86) PCT No.: PCT/NZ2019/050030
§ 371 (c)(1),
(2) Date: Sep. 24, 2020

(87) PCT Pub. No.: WO2019/190331
PCT Pub. Date: Oct. 3, 2019

(65) Prior Publication Data
US 2021/0115002 A1 Apr. 22, 2021

(30) Foreign Application Priority Data

Mar. 29, 2018 (NZ) ......................................... 741199

(51) Int. Cl.
C07D 295/033 (2006.01)
A61P 35/04 (2006.01)
(52) U.S. Cl.
CPC .......... *C07D 295/033* (2013.01); *A61P 35/04* (2018.01)
(58) Field of Classification Search
CPC ................................................ C07D 295/033
See application file for complete search history.

(56) References Cited

U.S. PATENT DOCUMENTS

| | | | | |
|---|---|---|---|---|
| 7,776,924 B2 * | 8/2010 | Denny | ................. | C07D 263/04 |
| | | | | 514/646 |
| 9,505,791 B2 * | 11/2016 | Smaill | .................. | C07C 255/58 |
| 9,873,710 B2 * | 1/2018 | Smaill | .................. | C07C 309/66 |
| 10,202,408 B2 * | 2/2019 | Smaill | ..................... | C07F 9/09 |
| 2007/0032455 A1 * | 2/2007 | Denny | ................. | C07C 317/48 |
| | | | | 514/79 |

FOREIGN PATENT DOCUMENTS

WO 2010/044686 A1 4/2010
WO 2014/031012 A1 2/2014

OTHER PUBLICATIONS

Guise; Chin J Cancer; 2014; 33, 80-86. DOI: 10.5732/cjc.012. 10285 (Year: 2014).*
Copp; Cell Chemical Biology, 2017, 24, 391-40. DOI: 10.1016/j.chembiol.2017.02.005 (Year: 2017).*
Thiolloy; Proceedings of the American Association for Cancer Research Annual Meeting 2018; Apr. 14-18, 2018; Chicago, IL. Philadelphia (PA): AACR; Cancer Res 2018;78(13 Suppl):Abstract nr 4959. (Year: 2018).*
Van der Wiel; Mol Cancer Ther, 2021 DOI: 10.1158/1535-7163. MCT-21-0406 (Year: 2021).*
Denny, W. A., et al., "Considerations for the design of nitrophenyl mustards as agents with selective toxicity for hypoxic tumor cells," Journal of Medicinal Chemistry, vol. 29(6): 879-887 (1986).
Flanagan, J. et al., "Morpholylureas are a new class of potent and selective inhibitors of the type 5 17-beta-hydroxysteroid dehydrogenase (AKR1C3)," Bioorganic & Medicinal Chemistry, vol. 22(3):967-977 (2014).
Gu, Y. et al, "Roles of DNA repair and reductase activity in the cytotoxicity of the hypoxia-activated dinitrobenzamide mustard PR-104A," Molecular Cancer Therapeutics, vol. 8: 1714-1723 (2009).
Gu. Y. et al., "Glucuronidation of anticancer prodrug PR-104A: species differences, identification of human UDP-glucuronosyltransferases, and implications for therapy," J Pharm Exp Ther., vol. 337:692-702 (2011).

(Continued)

*Primary Examiner* — Daniel R Carcanague
(74) *Attorney, Agent, or Firm* — Nelson Mullins Riley & Scarborough LLP; Jane E. Remillard, Esq.; Cynthia L. Kanik

(57) ABSTRACT

AKR1C3-activated prodrugs of Formula (I), pharmaceutical compositions comprising prodrugs of Formula (I), and their use in the treatment of hyperproliferative diseases such as cancer and for cell ablation. The compounds of the invention are able to penetrate neoplasm tissue and be selectively reduced to an active (cytotoxic) form by contact with an AKR1C3 enzyme found in the neoplasm. This active form is therefore able to ablate AKR1C3-expressing target cells of the neoplasm and therefore has particular utility in the treatment of cancer and other hyperproliferative disorders.

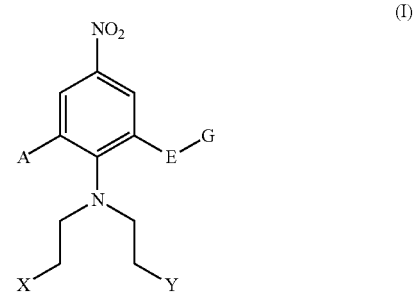

(I)

15 Claims, 8 Drawing Sheets

(56) References Cited

OTHER PUBLICATIONS

Guise, C. et al., "The Bioreductive Prodrug PR-104A Is Activated under Aerobic Conditions by Human Aldo-Keto Reductase 1C3," Therapeutics, Targets, and Chemical Biology, Cancer Research, vol. 70(4):1573-1584 (2010).
Helsby, N. et al, "Effect of nitroreduction on the alkylating reactivity and cytotoxicity of the 2,4-dinitrobenzamide-5-aziridine CB 1954 and the corresponding nitrogen mustard SN 23862: distinct mechanisms of bioreductive activation," Chemical Research in Toxicology, vol. 16(4): 469-478 (2003).
Hicks, K. et al., "Oxygen dependence and extravascular transport of hypoxia-activated prodrugs: comparison of the dinitrobenzamide mustard PR-104A and tirapazamine," International Journal of Radiation Oncology, Biology, Physics, vol. 69(2): 560-571 (2007).
International Search Report and Written Opinion, PCT/NZ2019/050030, dated May 24, 2019, 9 pages.
Mowday, A. et al., "Rational design of an AKR1C3-resistant analog of PR-104 forenzyme-prodrug therapy," Biochemical Pharmacology, vol. 116: 176-187 (2016).
Palmer, B. et al., "Hypoxia-selective antitumor agents. 5. Synthesis of water-soluble nitroaniline mustards with selective cytotoxicity for hypoxic mammalian cells," Journal of Medicinal Chemistry, vol. 35: 3214-3222 (1992).
Patterson, A. et al., "Mechanism of action and preclinical antitumor activity of the novel hypoxia-activated DNA cross-linking agent PR-104," Clinical Cancer Research, vol. 13(13): 3922-3932 (2007).
Silva, S., "The design and characterization of aldo-keto reductase 1C3 (AKR1C3) prodrugs for acute myeloid leukaemia," Auckland Cancer Society Research Centre Faculty of Medical and Health Sciences University of Auckland, 190 pages (2012).
Singleton, D. et al., "The nitroreductase prodrug SN 28343 enhances the potency of systemically administered armed oncolytic adenovirus ONYX-411(NTR)," Cancer Gene Therapy, vol. 14(12): 953-967 (2007).
Singleton, R. et al., "DNA cross-links in human tumor cells exposed to the prodrug PR-104A: relationships to hypoxia, bioreductive metabolism, and cytotoxicity," Cancer Research, vol. 69: 3884-3891 (2009).

\* cited by examiner

PRODRUG COMPOUNDS ACTIVATED BY AKR1C3 AND THEIR USE FOR TREATING HYPERPROLIFERATIVE DISORDERS

RELATED APPLICATIONS

This application is a 35 U.S.C. 371 national stage filing of International Application PCT/NZ2019/050030, filed Mar. 25, 2019, which claims priority from New Zealand Patent Application No. 741199 filed on Mar. 29, 2018. The entire contents of each of these applications are incorporated herein by reference in their entirety.

TECHNICAL FIELD

The invention relates to compounds useful as targeted cytotoxic agents, pharmaceutical compositions comprising them and methods of using them. In particular, the invention relates to nitroaromatic mustards and nitroaromatic mustard sulfonamides and their use as therapeutic agents for treating hyperproliferative disorders including cancer.

BACKGROUND OF THE INVENTION

Dinitrobenzamide mustard (DNBM) prodrugs were initially conceived as hypoxia-selective cytotoxins (Denny, W. A., and Wilson, W. R. Journal of Medicinal Chemistry, 1986, 29, 879-887). Nitro group reduction by human one-electron reductases is required to activate a latent nitrogen mustard moiety. Nitroreduction initially leads to the generation of an intermediary nitro radical anion metabolite. This intermediate can undergo further non-enzymatic reduction to the cytotoxic hydroxylamine and amine species in hypoxic cells, or, in the presence of molecular oxygen, it can be back-oxidised to the parent compound in a futile redox cycle, which is the basis of the hypoxia-selectivity of the class (as shown for PR-104A in Scheme 1) (Helsby et al, Chemical Research in Toxicology, 2003, 16, 469-478; Palmer et al, Journal of Medicinal Chemistry, 1992, 35, 3214-3222).

PR-104 is a phosphate ester "pre-prodrug" hydrolysed in vivo to the corresponding alcohol DNBM prodrug PR-104A, initially designed and optimised as a hypoxia-selective cytotoxin (Patterson et al, Clinical Cancer Research, 2007, 13, 3922-3932). PR-104 is 2-((2-bromo-ethyl)(2,4-dinitro-6-((2-(phosphonooxy)ethyl)carbamoyl)phenyl)-amino)ethyl methanesulfonate. PR-104A is 2-((2-bromoethyl)(2-((2-hydroxyethyl)-carbamoyl)-4,6-dinitrophenyl)amino)ethyl methanesulfonate. PR-104A is subsequently reduced to its cytotoxic metabolites, the hydroxylamine (PR-104H) and amine (PR-104M). These products can form interstrand cross-links with DNA, with disruption of the replication fork upon mitosis being the most likely mechanism of cytotoxicity (Scheme 1) (Gu et al, Molecular Cancer Therapeutics, 2009, 8, 1714-1723; Patterson et al, Clinical Cancer Research, 2007, 13, 3922-3932; Singleton et al, Cancer Research, 2009, 69, 3884-3891).

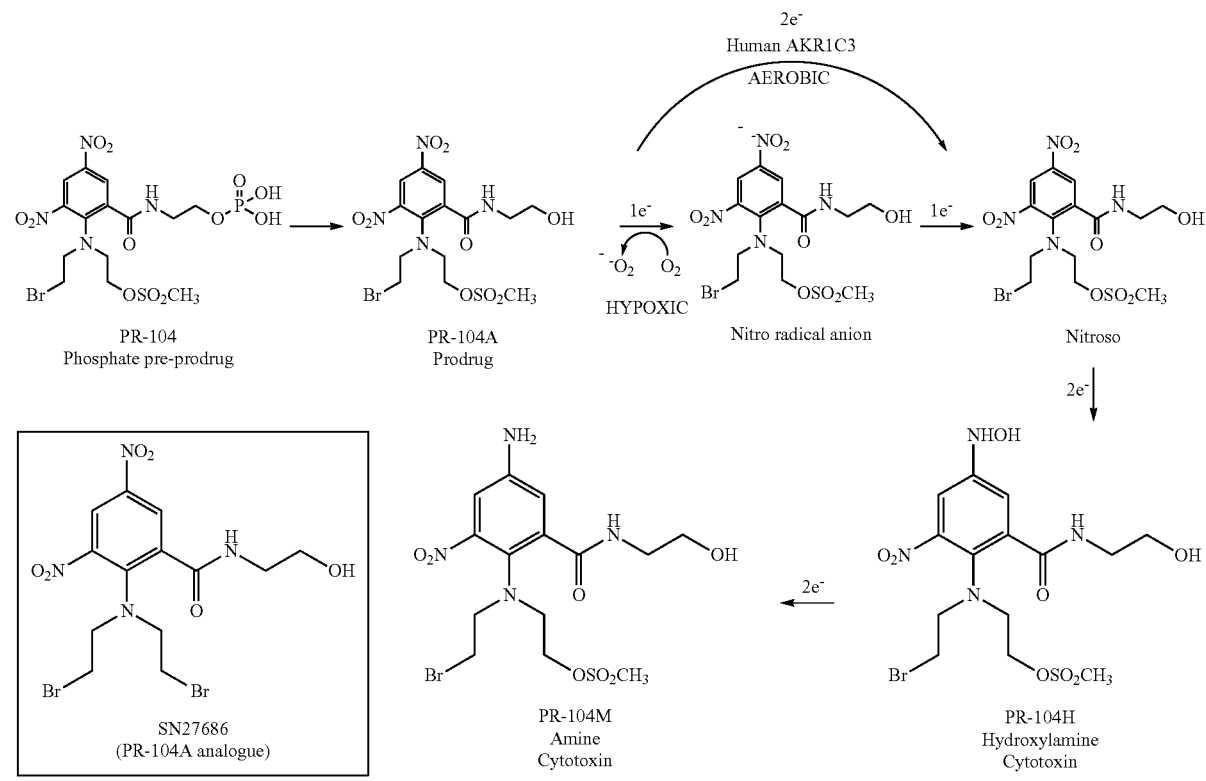

Scheme 1

Apart from its ability to target hypoxic cells in human tumour xenografts, PR-104A also displayed substantial monotherapy activity using in vivo assays which utilized excision assay and growth delay end points (Patterson et al., Clinical Cancer Research, 2007, 13, 3922-3932; Singleton et al., Cancer Research, 2009, 69, 3884-3891). Since only a fraction of cells in such xenografts are hypoxic, this significant monotherapy activity of PR-104A suggested a role for either a "bystander effect" (diffusion of cytotoxic metabolite into adjacent untargeted cells) and/or the aerobic (oxygen independent) activation of PR-104A by 2-electron reductases (Hicks et al, International Journal of Radiation Oncology, Biology, Physics, 2007, 69, 560-571). Microarray profiling of gene expression in a panel of 23 human cancer cell lines identified a distinct cluster of 5 genes (among others) belonging to the AKR superfamily, which were shown to positively correlate with aerobic activation of PR-104A (Guise et al., Cancer Research, 2010, 70, 1573-1584). HCT116 cells overexpressing these candidate reductase genes confirmed human aldo-keto reductase 1C3 (AKR1C3) to be a bona fide oxygen insensitive PR-104A reductase capable of activating PR-104A to its cytotoxic metabolites in vitro (Guise et al., Cancer Research, 2010, 70, 1573-1584). Two isogenic pairs of human tumour xenografts differing in AKR1C3 expression demonstrated a sustained growth delay of the AKR1C3-expressing xenografts when treated with PR-104A, relative to an AKR1C3 negative tumour xenograft.

While the oxygen insensitive activation of PR-104A by AKR1C3 represents an "off-target" mechanism of activation, it also presents the opportunity to exploit AKR1C3-expressing neoplasms with substantial expression of AKR1C3. Typically, the relative expression of AKR1C3 in these neoplasms is higher than the level of endogenous expression of AKR1C3 in healthy normal tissues. Neoplastic diseases reported to have substantial levels of AKR1C3 expression include acute myeloid leukaemia (AML) (Birtwistle et al., 2009, Mutat Res 662: 67-74), T-cell lineage acute lymphocytic leukaemia (T-ALL) (Benito et al., 2011, PLoS ONE, 6:e23108), chronic myeloid leukaemia (CML) (Graham et al., 2007, Stem Cells, 25:3111-20), hepatocellular carcinoma, non-muscle-invasive (superficial) bladder cancer, locally invasive bladder cancer, metastatic bladder cancer, gastric cancer, cervical cancer, pancreatic cancer, colon cancer, rectal cancer, oesophageal cancer, head and neck cancer, ovarian cancer, glioblastoma, sarcoma, endometrial cancer, prostate cancer, renal cancer and lung cancer (Guise et al., Can Res, 2010; 70:1573-84; Clin Can Res, 13:1322-32).

While PR-104A is the first example of a nitrobenzamide mustard prodrug that is metabolised by AKR1C3, it was not designed as such and accordingly it has a number of features that are less than optimal for a preferred AKR1C3-activated prodrug. These features are: 1) PR-104A is only modestly active as a micromolar cytotoxin against AKR1C3-positive cells (Guise et al, Cancer Research, 2010, 70, 1573-1584), 2) PR-104A metabolites possess significant bystander killing properties (Hicks et al., IJROBP, 2007, 69:560-71) and therefore can ablate neighbouring cells that may not express the target enzyme, 3) PR-104A is optimised for hypoxic-activation, and 4) PR-104A has poor pharmacokinetic properties due to rapid and extensive glucuronidation (Gu et al., J Pharm Exp Ther, 337:692-71). Accordingly, it would be useful to provide alternative AKR1C3-activated prodrugs or prodrugs with preferred properties compared to PR-104A.

Dinitrobenzene mustard prodrug analogues of PR-104A as AKR1C3-activated prodrugs are known (WO 2010/044686). However, little data is provided to indicate that these derivatives address any of the limitations of PR-104A as an AKR1C3-activated prodrug.

Further examples of nitrobenzamide mustard prodrugs metabolised by AKR1C3 have been reported (Silva, S. University of Auckland Library, MSc Thesis, 2012). Examples include SN33539, SN34947, SN34951, SN34118, SN33540, SN35028 and SN34454. These examples are reported to have a number of features that are less than optimal for a preferred AKR1C3-activated prodrug, including 1) only modest improvement in AKR1C3-dependent cytotoxicity in AKR1C3-positive cells relative to PR-104, 2) like PR-104A, metabolites possess significant bystander killing properties and therefore can ablate neighbouring cells that may not express the target enzyme, and 3) high binding affinity to the AKR1C3 active site resulting in inhibition of prodrug metabolism at high prodrug concentrations. Accordingly, it would be useful to provide alternative AKR1C3-activated prodrugs or prodrugs with preferred properties compared to SN33539, SN34947, SN34951, SN34118, SN33540, SN35028 and SN34454.

Scheme 2

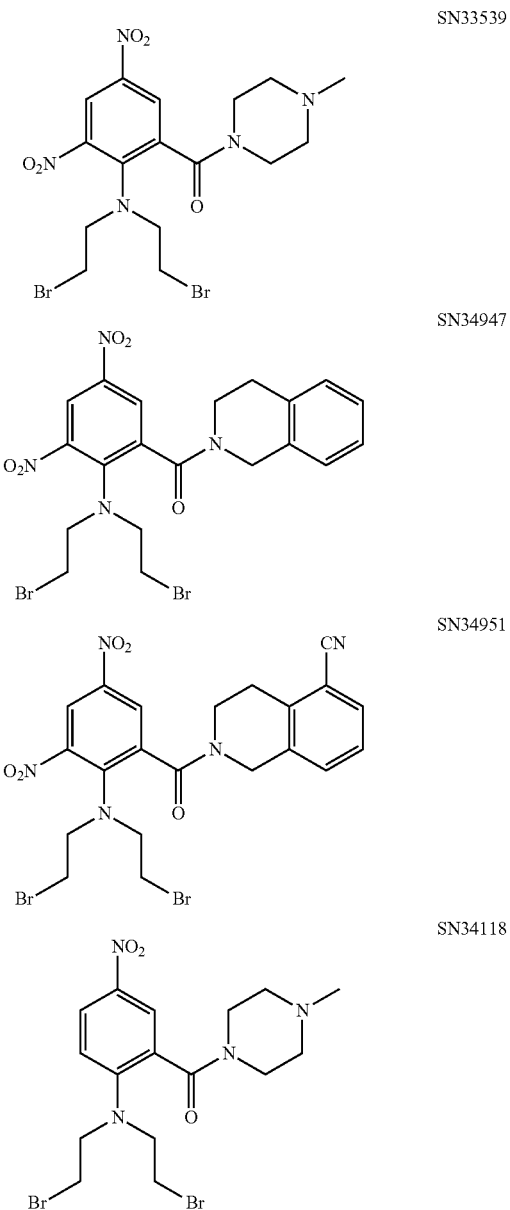

-continued

SN33540

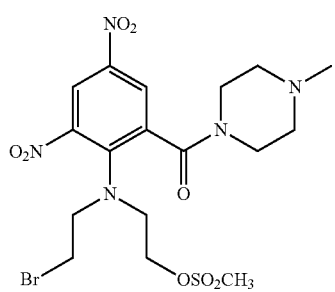

SN35028

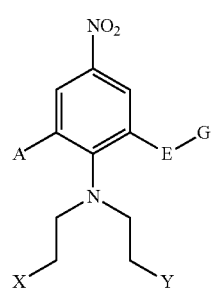

SN34454

It is therefore an object of the invention to provide novel AKR1C3-activated prodrugs for use in the treatment of hyperproliferative diseases such as cancer, or at least to provide a useful alternative to other therapeutic agents.

SUMMARY OF THE INVENTION

In a first aspect of the invention there is provided a compound of Formula (I):

(I)

wherein:
A is H, C1-C6 alkyl, C1-C6 alkenyl, C1-C6 alkynyl, CFH$_2$, CF$_2$H, CF$_3$, F, Cl, Br, I, OCF$_3$, COR, or CON(R)$_2$;
E is SO, or SO$_2$;
X is Cl, Br, I, or OSO$_2$R;
Y is Cl, Br, I, or OSO$_2$R;
each R is independently H or C1-C6 alkyl;
G is a radical selected from the group comprising Formulae (B)-(AA):

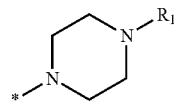 (B)

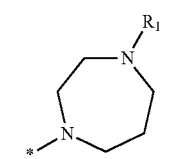 (C)

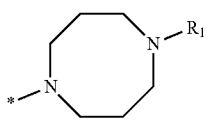 (D)

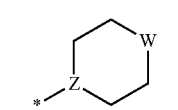 (F)

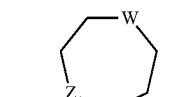 (H)

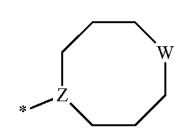 (J)

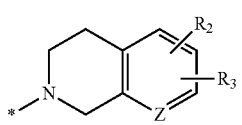 (K)

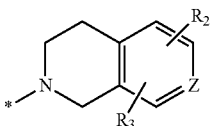 (L)

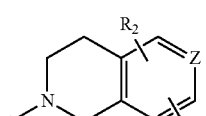 (M)

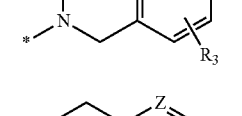 (N)

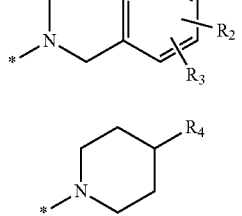 (O)

-continued

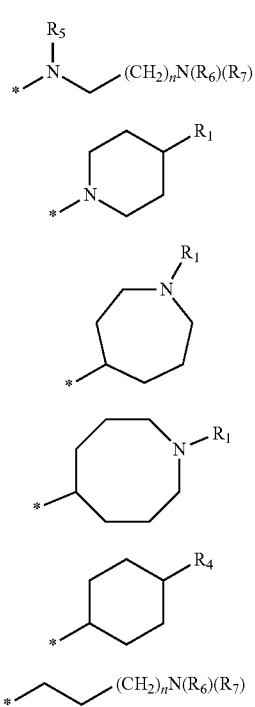

(P)

(Q)

(S)

(T)

(U)

(AA)

wherein:

$R_1$ is H, C1-C6 alkyl, $CH_2(CH_2)_nOH$, $CH_2CH(OH)CH_2OH$, phenyl, pyridinyl, benzyl, or pyridinylmethyl, provided that when $R_1$ is phenyl, pyridinyl, benzyl or pyridinylmethyl, $R_1$ is optionally substituted in any available position with C1-C6 alkyl, C1-C6 alkenyl, C1-C6 alkynyl, $OR_6$, $N(R_6)(R_7)$, $CFH_2$, $CF_2H$, $CF_3$, F, Cl, Br, I, $OCF_3$, $COR_6$, $CON(R_6)(R_7)$, $SOR_6$, $SON(R_6)(R_7)$, $SO_2R_6$, $SO_2N(R_6)(R_7)$, CN, or $NO_2$;

$R_2$ and $R_3$ are each independently H, C1-C6 alkyl, C1-C6 alkenyl, C1-C6 alkynyl, $OR_6$, $N(R_6)(R_7)$, $CFH_2$, $CF_2H$, $CF_3$, F, Cl, Br, I, $OCF_3$, $COR_6$, $CON(R_6)(R_7)$, $SOR_6$, $SON(R_6)(R_7)$, $SO_2R_6$, $SO_2N(R_6)(R_7)$, CN, or $NO_2$;

$R_4$ is $N(R_6)(R_7)_nOH$, $OCH_2(CH_2)_nN(R_6)(R_7)$, or $CH_2(CH_2)_nN(R_6)(R_7)$;

$R_5$ is H, or C1-C6 alkyl group;

$R_6$ and $R_7$ are each independently H, or C1-6 alkyl, or $R_6$ and $R_7$ taken together form a substituted or unsubstituted 5- or 6-membered heterocyclic ring;

Z is CH or N;

W is $CH_2$, O, S, SO, or $SO_2$;

n is 0 to 6;

* represents a point of attachment to Formula (I);

or a pharmaceutically acceptable salt thereof.

In some embodiments of the invention:

A is H, C1-C6 alkyl, C1-C6 alkenyl, C1-C6 alkynyl, $CFH_2$, $CF_2H$, $CF_3$, or $OCF_3$;

E is SO, or $SO_2$;

X is Br, or $OSO_2R$;

Y is Br, or $OSO_2R$;

each R is independently H or C1-C6 alkyl;

G is a radical selected from the group comprising Formulae (B), (C), (D), (O) and (P):

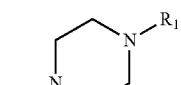

(B)

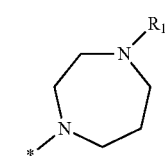

(C)

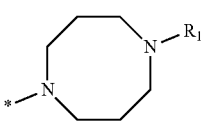

(D)

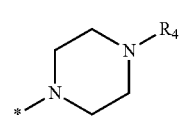

(O)

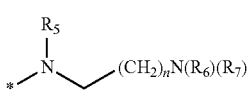

(P)

wherein $R_1$ is H, C1-C6 alkyl, $CH_2(CH_2)_nOH$, $CH_2CH(OH)CH_2OH$;

$R_4$ is $N(R_6)(R_7)$, $OCH_2(CH_2)_nN(R_6)(R_7)$, or $CH_2(CH_2)_nN(R_6)(R_7)$;

$R_5$ is H, or C1-C6 alkyl;

$R_6$ and $R_7$ are each independently H, or C1-6 alkyl, or $R_6$ and $R_7$ taken together form a substituted or unsubstituted 5- or 6-membered heterocyclic ring;

n is 0 to 6;

* represents a point of attachment to Formula I;

or a pharmaceutically acceptable salt thereof.

In some embodiments of the invention:

A is H, C1-C6 alkynyl, $CFH_2$, $CF_2H$, or $CF_3$;

E is $SO_2$;

X is Br, or $OSO_2R$;

Y is Br, or $OSO_2R$;

each R is independently H or C1-C6 alkyl;

G is a radical selected from the group comprising Formulae (B), (C), (D), (O) and (P):

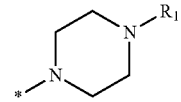

(B)

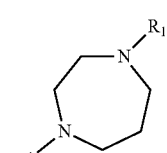

(C)

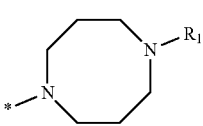

(D)

-continued

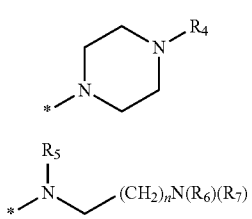

wherein $R_1$ is H, C1-C6 alkyl, $CH_2(CH_2)_nOH$, $CH_2CH(OH)CH_2OH$;

$R_4$ is $N(R_6)(R_7)$, $OCH_2(CH_2)_nN(R_6)(R_7)$, or $CH_2(CH_2)_nN(R_6)(R_7)$;

$R_5$ is H, or C1-C6 alkyl;

$R_6$ and $R_7$ are each independently H, or C1-6 alkyl, or $R_6$ and $R_7$ taken together form a substituted or unsubstituted 5- or 6-membered heterocyclic ring;

n represents 0 to 6;

* represents a point of attachment to Formula I;

or a pharmaceutically acceptable salt thereof.

In some embodiments of the invention A is H.

In some embodiments of the invention the compound has the formula:

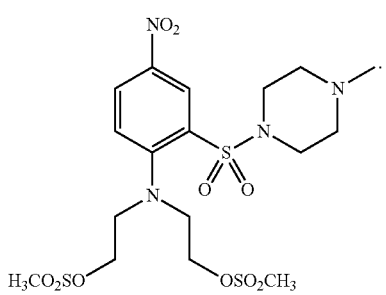

In some embodiments of the invention the compound has the formula:

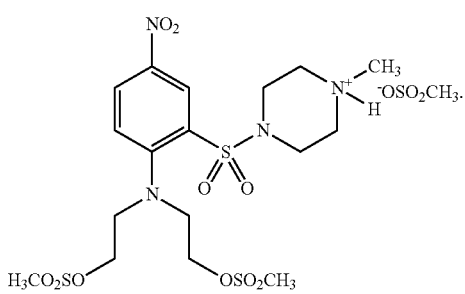

In some embodiments of the invention the pharmaceutically acceptable salt is a mesylate salt.

In a second aspect of the invention there is provided a pharmaceutical composition comprising a compound of the invention together with a pharmaceutically acceptable carrier.

In preferred embodiments, the compound of the invention is:

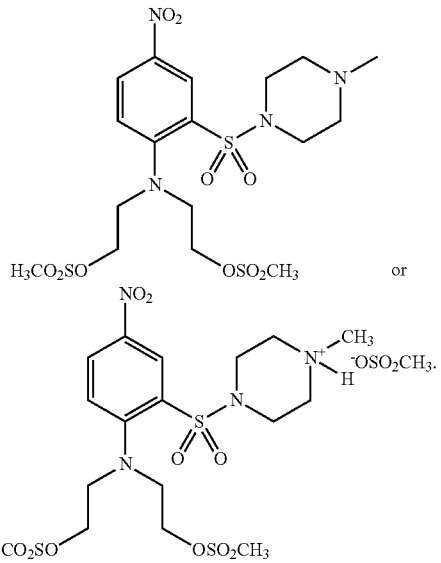

In another aspect of the invention there is provided a method of treating a hyperproliferative disorder comprising administering to a person a compound of the invention. In preferred embodiments, the compound of the invention is:

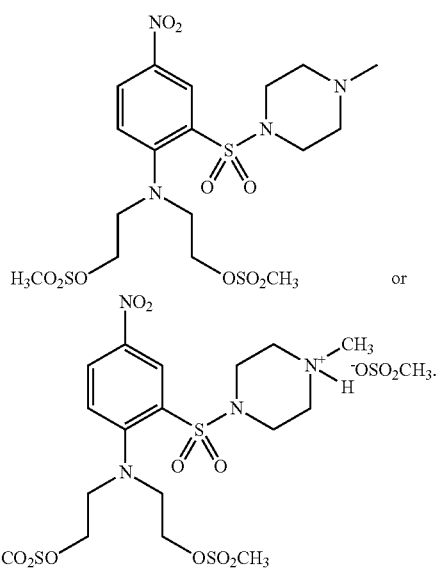

In some embodiments of the invention the hyperproliferative disorder is cancer. Preferably, the hyperproliferative disorder is characterised by association with the formation of neoplasms that express a detectable amount of AKR1C3.

In some embodiments of the invention the cancer is acute myeloid leukaemia, T-cell lineage acute lymphocytic leukaemia (T-ALL), chronic myeloid leukaemia (CML), hepatocellular carcinoma, non-muscle-invasive (superficial) bladder cancer, locally invasive bladder cancer, metastatic bladder cancer, gastric cancer, cervical cancer, pancreatic cancer, colon cancer, rectal cancer, oesophageal cancer, head and neck cancer, ovarian cancer, glioblastoma, sarcoma, endometrial cancer, prostate cancer, renal cancer or lung cancer.

In another aspect of the invention there is provided a method of cell ablation comprising the steps:
  a. activating a compound of the invention with at least one AKR1C3 enzyme to produce a cytotoxic metabolite capable of ablating a target cell; and
  b. contacting the target cell with the cytotoxic metabolite to ablate the cell.

In another aspect of the invention there is provided the use of a compound of the invention in the manufacture of a medicament for treating a hyperproliferative disorder.

In a further aspect of the invention there is provided a pharmaceutical composition comprising a compound of the invention for use in the treatment of a hyperproliferative disorder.

All embodiments referred to above in connection with the first aspect of the invention are also embodiments of the abovementioned subsequent aspects of the invention.

DETAILED DESCRIPTION

Definitions

Figure 1:
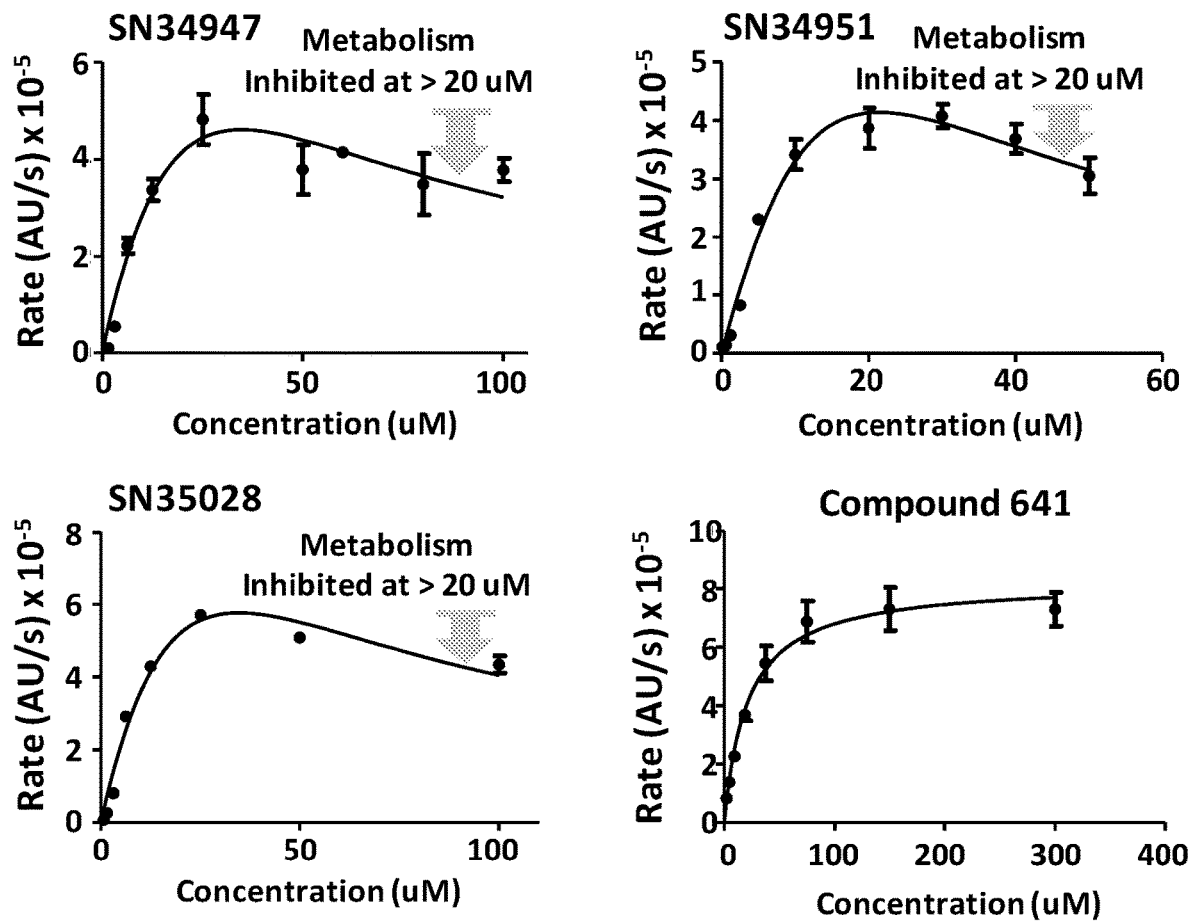
FIG. 1 shows the rate of metabolism of prior art compounds SN34947, SN34951 and SN35028 by recombinant AKR1C3 as a function of drug concentration, compared to the rate of metabolism of compound 641 by recombinant AKR1C3 as a function of drug concentration. Compounds SN34947, SN34951 and SN35028 demonstrate inhibition of metabolism by AKR1C3 at concentrations >20 µM, an unfavourable property not observed for compound 641.

The term "alkyl" means any saturated hydrocarbon radical and is intended to include both straight-chain and branched-chain alkyl groups. Examples of alkyl groups include, but are not limited to, methyl, ethyl, n-propyl, iso-propyl, n-butyl, iso-butyl, sec-butyl, t-butyl, n-pentyl, 1,1-dimethylpropyl, 1,2-dimethylpropyl, 2,2-dimethylpropyl, 1-ethylpropyl, 2-ethylpropyl, n-hexyl, and 1-methyl-2-ethylpropyl. The term "C1-C6 alkyl" means any alkyl radical having up to 6 carbon atoms.

The term "alkenyl" means any hydrocarbon radical having at least one double bond, and is intended to include both straight- and branched-chain alkenyl groups. Examples of alkenyl groups include, but are not limited to, ethenyl, n-propenyl, iso-propenyl, n-butenyl, iso-butenyl, sec-butenyl, t-butenyl, n-pentenyl, 1,1-dimethylpropenyl, 1,2-dimethylpropenyl, 2,2-dimethylpropenyl, 1-ethylpropenyl, 2-ethylpropenyl, n-hexenyl, and 1-methyl-2-ethylpropenyl.

The term "alkynyl" means any hydrocarbon radical having at least one triple bond, and is intended to include both straight- and branched-chain alkynyl groups. Examples of alkynyl groups include, but are not limited to, ethynyl, n-propynyl, iso-propynyl, n-butynyl, iso-butynyl, sec-butynyl, t-butynyl, n-pentynyl, 1,1-dimethylpropynyl, 1,2-dimethylpropynyl, 2,2-dimethylpropynyl, 1-ethylpropynyl, 2-ethylpropynyl, n-hexynyl, and 1-methyl-2-ethylpropynyl.

The term "alkylene" means a diradical corresponding to an alkyl group. Examples of alkylene groups include, but are not limited to, methylene and ethylene.

The term "cycloalkyl" means a saturated or partially saturated non-aromatic carbocyclic group, having preferably from 3 to 8 ring carbon atoms. Examples of cycloalkyl groups include, but are not limited to, cyclopropyl, cyclobutyl, cyclopentyl, cyclohexyl, cycloheptyl, and cyclooctyl.

The term "pyridinyl" includes all possible pyridine isomers including pyridin-2-yl, pyridin-3-yl and pyridin-4-yl.

The term "pyridinylmethyl" includes all possible pyridinylmethyl isomers including (pyridin-2-yl)methyl, (pyridin-3-yl)methyl and (pyridin-4-yl)methyl.

The term "prodrug" means an inactive compound that is converted to a reactive cytotoxic metabolite once activated. Preferably activation occurs within or therapeutically proximate to a target cell within the local tumour microenvironment by reduction of a nitro group. Prodrugs of the present invention may be activated by reduction by an AKR1C3 enzyme independent of tissue oxygen concentration, i.e. in oxic or hypoxic tissues.

The terms "activation" and "metabolism" with reference to prodrugs refer to the catalytic reduction process that a prodrug may undergo following contact with an enzyme. The prodrug may be activated/metabolised to yield alternative compounds such as cytotoxic metabolites that may have beneficial activity for therapeutic applications.

The term "ablation" is to be considered in its broadest context and means the complete ceasing of the function of the target being ablated, and is also intended to encompass any degree of inhibition or suppression of the function of the target where the target includes but is not limited to a cell.

The term "cell" refers to a biological sub-unit that is specialised in carrying out a particular function or functions. For the purposes of the present invention, the term "cell" also encompasses the medium in which the cell is found. For example this may mean a hypoxic region of a tumour or the cell matrix which supports the cell in vivo or in vitro.

The term "cytotoxicity" means the degree to which a compound effects ablation of a target cell. Cytotoxicity may be measured by any known method including, for example, an IC50 half maximal inhibitory concentration assay using an HCT116 cell line as described in the Examples. Cytotoxicity in such assays may be determined by measuring a compound's ability to inhibit proliferation of a neoplastic cell line or by measuring a compound's ability to prevent the clonogenic survival of a neoplastic cell line.

The term "catalytic efficiency" means the relative ease with which the human AKR1C3 enzyme metabolises different prodrug substrates as determined by comparing the substrate's affinity for the enzyme and rate of metabolism by the enzyme.

The term "endogenous" means naturally occurring, originating or produced within an organism, tissue, or cell. For example, endogenous enzymes in a mammal are enzymes that are naturally present in mammalian cells.

The terms "hypoxic", "hypoxic tissue" and the like refer to a concentration of oxygen in tissue that is significantly lower the normal physiological concentration of oxygen in healthy well-perfused tissue. In particular, oxygen tensions below approximately 1% (10,000 parts per million oxygen; 7.6 mmHg) are to be considered hypoxic.

The term "substantially insensitive to activation by hypoxic tissue", and similar terms, indicates that a compound is not metabolised by a hypoxic tissue and therefore does not provide hypoxia-dependent cytotoxicity in that tissue. When tested in vitro in cancer cell lines under oxic and anoxic conditions such a compound will not give Hypoxic Cytotoxicity Ratios of greater than 5.

The term "bystander effect" means an effect triggered by treatment of a target AKR1C3 enzyme expressing cell with a prodrug and refers to the secondary ablation effect on cells or tissues in the local microenvironment to a target cell. Without wishing to be bound by theory, the bystander effect is believed to be caused by the diffusion of cytotoxic prodrug metabolites (activated prodrugs) from the site of production to affect non-AKR1C3 enzyme expressing cells separate from the target cell. Bystander effect may be quantified by any known method including according to methods described in Wilson et al., 2002, Cancer Res. 62:1425-1432, by employing a 3D multicellular layer (MCL) composed of a minority (approximately 1-5%) of AKR1C3 enzyme-expressing 'activator' cells, mixed with a majority (approximately 95-99%) of parental (wild-type) 'target' cells. The prodrug concentrations for 10% survival ($C_{10}$) of target cells (wild-type cells) grown without activators (T), and targets in co-culture ($T_C$) and activators (AKR1C3-expressing cells) in co-culture ($A_C$) can be determined. The bystander effect of a test prodrug is measured by the bystander effect efficiency which can be calculated using the algorithm ((Log $C_{10}$T–Log $C_{10}T_C$)/(Log $C_{10}$T–Log $C_{10}A_C$)). A BEE value of less than about 35% is considered "substantially minimal".

The term "treatment" is to be considered in its broadest context. The term does not necessarily imply that a subject is treated until total recovery. Accordingly, "treatment" broadly includes, for example, the prevention, amelioration or management of one or more symptoms of a disorder, or the severity of one or more symptoms, and preventing or otherwise reducing the risk of developing secondary complications.

The term "prevention" of disease should not be taken to imply that disease development is completely prevented, and includes delay of disease development.

The term "nitroaromatic mustards" means any compound possessing an aromatic ring that is substituted with nitro and aniline mustard functionalities.

The term "nitroaromatic mustard sulfonamide" means any compound possessing an aromatic ring that is substituted with nitro and aniline mustard functionalities where an additional substituent further contains a sulfonamide moiety.

The term "AKR1C3 enzyme" means the human enzyme aldo-keto reductase 1C3. The aldo-keto reductases (AKRs) are a superfamily of cytosolic enzymes that are involved in the reduction of aldehydes and ketones to their corresponding primary and secondary alcohols, respectively, from a variety of endogenous and exogenous substrates (Jez et al, The Biochemical Journal, 1997, 326, 625-636). AKRs require the presence of a cofactor NADPH in order to catalyse the reduction of carbonyl groups (Schlegel et al, Biochemistry, 1998, 37, 3538-3548). The human AKRs are classed into three families (AKR1, AKR6 and AKR7) of which AKR1 is the best characterised in terms of structure and function (Penning, T. M., and Drury, J. E. Archives of Biochemistry and Biophysics, 2007, 464, 241-250). The AKR1C subfamily includes AKR1C1-4, with all four enzymes having hydroxysteroid dehydrogenase (HSD) activity (Penning et al, The Biochemical Journal, 2000, 351, 67-77). The genes encoding AKR1C1-4 share more than 86% amino acid sequence identity, and show differences in substrate and regiospecificity of the sites metabolised (Penning, T. M., and Byrns, M. C. Annals of the New York Academy of Sciences, 2009, 1155, 33-42). AKR1C3 is the enzyme responsible for the reduction of Prostaglandin D2 (PGD2) in humans.

The term "AKR1C3-activated prodrug" means a compound that is readily metabolised by human AKR1C3. AKR1C3 metabolism can be demonstrated by incubating test compounds and NADPH co-factor with recombinant AKR1C3 protein and assaying for the loss of NADPH co-factor, where a loss of co-factor indicates enzymatic metabolism of the compounds.

The term "pharmaceutically acceptable" means entities that are useful in preparing a pharmaceutical composition that is generally safe, non-toxic, and neither biologically nor otherwise undesirable and includes that which is acceptable for veterinary as well as human pharmaceutical use.

The term "pharmaceutically acceptable salts" means salts of a compound that are pharmaceutically acceptable and that possess the desired pharmacological activity of the compound. Such salts include:

acid addition salts formed with inorganic acids such as hydrochloric acid, hydrobromic acid, sulfuric acid, nitric acid, phosphoric acid and the like; or formed with organic acids such as acetic acid, methanesulfonic acid, maleic acid, tartaric acid, citric acid, para-toluenesulfonic acid, isethionic acid and the like;

salts formed when an acidic proton either is replaced by a metal ion, e.g. an alkali metal ion, an alkaline earth ion, or an aluminium ion; or coordinates with an organic or inorganic base. Acceptable organic bases include ethanolamine, diethanolamine, N-methylglucamine, triethanolamine and the like. Acceptable inorganic bases include aluminium hydroxide, calcium hydroxide, potassium hydroxide, sodium carbonate and sodium hydroxide;

salts comprising an ion selected from chloride, bromide, sulfate, nitrate, phosphate, acetate, mesylate, maleate, tartrate, citrate, methanesulfonate, tosylate, isethionate and the like; and salts of phosphate acids and carboxylic acids including sodium, calcium, potassium salts.

It will be understood that the terms "mesylate" and "methanesulfonate" are interchangeable and refer to the same entity.

The term "pharmaceutical composition" as used herein refers to a mixture of one or more of the compounds of Formula (I), or pharmaceutically acceptable salts, or hydrates thereof, with other chemical components, such as physiologically acceptable carriers and excipients. The purpose of a pharmaceutical composition is to facilitate administration of a compound to an organism.

The terms "administered", "administration" and the like when used in reference to the administration of a compound to a target cell are intended to encompass all methods of introduction, for example intravenous, intramuscular, subcutaneous and oral and are not intended to be limited to direct administration to the site of a tumour cell. The terms are also intended to encompass indirect methods of introducing the compound to the target cell, for example intravesical instillation and transcatheter arterial chemoembolisation.

The term "therapeutically effective amount" means an amount of a compound that has the potential to elicit a therapeutic effect. In the case of a prodrug, it will be understood that this will only actually elicit a therapeutic effect after activation/metabolism of that prodrug.

The term "therapeutically proximate" means, in relation to a bystander effect, that a cell is sufficiently close to an enzyme expressing cell capable of activating a prodrug such that the cell receives therapeutically effective concentrations of active/cytotoxic prodrug metabolites. This is typically within 1 to 10 cell diameters of the enzyme expressing cell.

The term "increased expression" and like terms when used in relation to an AKR1C3 enzyme should be taken broadly to include any increase in production of the protein or increase in expression of one or more nucleic acids encoding same protein. It should not be taken to mean that the protein (or nucleic acid) is expressed at any particular level. Methods for measuring expression of an AKR1C3 will be known to those skilled in the art, but exemplary methods include (i) genotyping of nucleic acid sequence, whether amplified or not, performed using a variety of techniques, such as polymerase chain reaction (PCR)-based analysis, sequence analysis, and electrophoretic analysis, which can be used alone or in combination; (ii) determination of a transcriptional gene expression profile using hybridization techniques such as Northern analysis and slot blot hybridisation or by performing reverse-transcriptase (RT)-PCR amplification followed by gel electrophoresis; (iii) detecting the presence or level of expressed protein for determining a protein expression profile. For example, a protein biomarker can be analysed using an immunoassay. A protein expression profile can also be evaluated using electrophoresis, e.g., Western blotting. Any suitable immunoassay can be utilised for determining the presence or level of one or more protein biomarkers in a sample. Suitable immunoassay techniques include enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarisation immunoassays (FPIA); and chemiluminescence assays (CL); (iv) quantitative Western blotting to detect or determine the level of protein biomarker in a sample. Western blots can be quantitated by well-known methods such as scanning densitometry or phosphorimaging; (v) immunohistochemistry (IHC) to determine the level of protein biomarker in a sample.

The term "immunohistochemistry" or "IHC" encompasses techniques that utilise the visual detection of fluorescent dyes or enzymes coupled (i.e., conjugated) to antibodies that react with the biomarker using fluorescent microscopy or light microscopy.

The term "substantial expression of AKR1C3" means, in relation to a neoplasm, that the neoplasm expresses AKR1C3 in an amount sufficient to be detected by any known method and provides selective metabolism and therefore cytotoxicity of an AKR1C3-activated prodrug relative to a neoplasm that exhibits negligible AKR1C3 expression.

The term "hyperproliferative disorder" and like terms means medical disorders pertaining to, or caused by, the uncontrolled growth (proliferation) of cells and include cancers such as acute myeloid leukaemia (AML), T-cell lineage acute lymphocytic leukaemia (T-ALL), chronic myeloid leukaemia (CML), hepatocellular carcinoma, non-muscle-invasive (superficial) bladder cancer, locally invasive bladder cancer, metastatic bladder cancer, gastric cancer, cervical cancer, pancreatic cancer, colon cancer, rectal cancer, oesophageal cancer, head and neck cancer, ovarian cancer, glioblastoma, sarcoma, endometrial cancer, prostate cancer, renal cancer and lung cancer.

The term "neoplasm" and like terms means an abnormal mass of tissue as a result of abnormal growth or division of cells.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Compounds of the Invention

The compounds of the invention are defined according to Formula (I) above. The inventors have found several prodrug compounds that are activated by AKR1C3 enzymes to produce cytotoxic metabolites useful for the targeted treatment of hyperproliferative disorders including cancer. These compounds have particular utility for the treatment of hyperproliferative disorders that form neoplasms with substantial expression of AKR1C3. The level of expression of AKR1C3 in such neoplasms enables targeted selective activation of these prodrugs at the site of neoplasm formation. This selectivity may be desirable to reduce side effects that would occur if untargeted activation of the prodrugs occurred in normal healthy tissue. The selectivity may also reduce the therapeutically effective dose required which has advantages including reduced cost and a reduction in potential side effects.

The compounds of the invention are able to penetrate neoplasm tissue and be selectively reduced to an active (cytotoxic) form by contact with an AKR1C3 enzyme found in the neoplasm. This active form is therefore able to ablate AKR1C3-expressing target cells of the neoplasm and therefore has particular utility in the treatment of cancer and other hyperproliferative disorders.

The inventors have found that the mesylate salt form of compounds of the invention shows particular advantages that make them suitable for clinical administration. In particular, the mesylate salt forms exhibit higher solubility than the free base form (see Example 13). The mesylate form is also expected to be more stable than other salt forms such as the HCl salt and the HBr salt. Without wishing to be bound by theory, it is believed that stability of the mesylate salt is improved due to the methanesulfonic acid (used to produce the mesylate salt) not being a sufficiently strong nucleophile to displace the X and Y leaving groups of the mustard. In contrast, using HBr or HCl to produce the salt form will result in the Cl— or Br— of these salt forms displacing one or both of the X and Y leaving groups of the mustard. This can reduce stability. For example, if HBr is used to produce a hydrobromide salt of a bis-mesylate mustard, bromomesylate and dibromo mustard impurities are likely to be formed which reduce the overall purity specification of the active pharmaceutical ingredient.

Therefore, the invention also provides a mesylate salt of a compound of Formula (I). Preferably, the mesylate salt is compound 641.Ms:

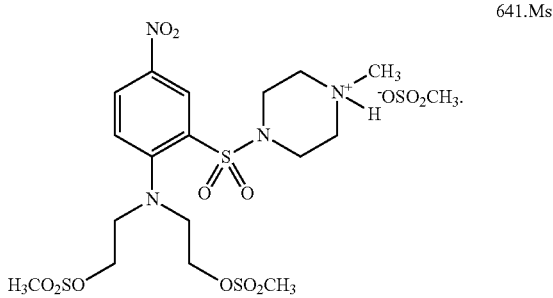

641.Ms

Cytotoxicity Induced by AKR1C3

Example 9 (Table 2) illustrates the increased cytotoxicity of compounds of the invention by increased inhibition of HCT-116 cell growth in the presence of AKR1C3 relative to the absence of AKR1C3. Example 10 (Table 3) demonstrates AKR1C3 dependent inhibition of growth of SNU398 hepatocellular carcinoma cells. AKR1C3 expressing cells exhibit up to 5,150 times less growth than non-AKR1C3 expressing cells. In contrast, PR-104A exhibits only a 77-fold increase in sensitivity when in the presence of AKR1C3.

Example 11 (Table 4) further demonstrates AKR1C3-selective cell growth inhibition in H460 lung cancer cells and PLC/PRF/5 hepatocellular carcinoma cells by compounds of the invention.

Example 14 and FIGS. 2 to 7 show the in vivo effect of compounds of the invention which profoundly reduce cancer tumour growth. This indicates prodrug metabolism by endogenously expressed AKR1C3 in H460, PLC/PRF/5 and SW780 tumour xenografts, and genetically engineered overexpression of AKR1C3 in SNU-398 tumour xenografts.

The AKR1C3-activated compounds exhibit an increase in cytotoxicity relative to the same compounds in the absence of AKR1C3 of at least 10 times, at least 13 times, at least 20 times, at least 28 times, at least 29 times, at least 36 times, at least 38 times, at least 50 times, at least 57 times, at least 91 times, at least 100 times, at least 116 times, at least 144 times, at least 145 times, at least 150 times, at least 167 times, at least 200 times, at least 250 times, at least 300 times, at least 469 times, at least 500 times, at least 597 times, at least 687 times, at least 816 times, at least 978 times, at least 1000 times, at least 1500 times, at least 1632 times, at least 1930 times, at least 2000 times, at least 2955 times, at least 3000 times, at least 3340 times, at least 4000 times, at least 4260 times.

PR-104A is known to be metabolised by AKR1C3 but exhibits properties that are less than optimal for an effective prodrug. The compounds of the invention provide an alternative to PR-104A. These novel compounds have been found to exhibit desirable properties for the treatment of hyperproliferative diseases.

In particular, the AKR1C3 activated compounds of the invention exhibit an increase in cytotoxicity relative to the cytotoxicity of PR-104A, SN27686, SN33539, SN35028, SN34947, SN34951 and SN34118 in the presence of AKR1C3. Examples 9-11 show that the cytotoxicity of several compounds of the invention is many times more cytotoxic than the known reference compounds.

Improved Enzyme Kinetics

The compounds of the invention exhibit surprisingly high catalytic efficiency with respect to metabolism by AKR1C3. They also exhibit increased catalytic efficiency with AKR1C3 relative to the catalytic efficiency of PR-104A with AKR1C3. Increased catalytic efficiency allows the activation of the prodrug to become more efficient, and hence more cytotoxic metabolites are generated in a given time. This improves the likelihood of rapid and complete neoplasm ablation thus resulting in a more effective treatment option.

PR-104A exhibits a catalytic efficiency value ($k_{cat}/K_m$) of 256,206 $M^{-1}s^{-1}$. Compounds of the invention exhibit a catalytic efficiency with AKR1C3 of at least 1,645,614, at least 1,922,414, at least 2,084,888, and at least 2,370,091 $M^{-1}s^{-1}$.

Example 8 (Table 1) illustrates the increased catalytic efficiency of compounds of the invention by analysis of enzyme kinetics of representative compounds compared to compound PR-104A.

Lack of Hypoxia Activation

The inventors have surprisingly found that a number of compounds of the invention exhibit minimal or zero activation in hypoxic tissues relative to their activation in oxic tissues. Since PR-104A is hypoxia activated, this insensitivity to hypoxia is particularly unexpected. Therefore particular compounds of the invention will be selectively activated by AKR1C3 but substantially insensitive to activation in hypoxic tissues. In some circumstances, this property has advantages because hypoxic activation may be considered an off-mechanism behaviour and potentially causes undesirable and uncontrolled effects. Accordingly, the invention also provides a compound that is substantially insensitive to activation by tissue hypoxia.

Insensitivity to hypoxic activation generally occurs in mono-nitro compounds which are unsubstituted in the 3-position. Without wishing to be bound by theory, it is believed that this is because they possess a one-electron reduction potential (E[1]) for the nitro group that is generally too low for hypoxic activation. A reasonably strong electron withdrawing group is required in this 3-position (e.g. $NO_2$, CN, $MeSO_2$ or $CF_3$) to raise the E[1] of the 5-nitro substituent sufficiently to observe hypoxia-selective reduction.

PR-104A is known to be activated in hypoxic tissues and while this property can have advantages in some situations, the compounds indicated above provide treatment options where hypoxia activation is undesirable. Hypoxia insensitive compounds of the invention in a hypoxic tissue are less than 25 times, less than 22 times, less than 21 times, less than 20 times, less than 15 times, less than 10 times, less than 5 times, less than 4 times, less than 3 times as cytotoxic relative to the compound in an oxic tissue, or their cytotoxicity is substantially unchanged between an oxic versus a hypoxic tissue.

PR-104A exhibits a substantial (20 times) increase in cytotoxicity in a hypoxic tissue relative to an oxic tissue. Accordingly, the invention also provides a method of treatment of a hyperproliferative disorder as described above wherein the AKR1C3-activated compound exhibits a decreased difference in cytotoxicity between an oxic versus a hypoxic tissue relative to the difference in cytotoxicity in an oxic versus a hypoxic tissue exhibited by PR-104A.

Lack of Bystander Effect

Certain AKR1C3-activated compounds of the invention also exhibit a bystander effect that is substantially minimal or zero. A substantial bystander effect is desirable in some situations to ablate tissues neighbouring the tissue in which the prodrug is activated. However, this effect can serve to lessen the specificity of the treatment and potentially ablates non-neoplastic, healthy tissues. Accordingly, the compounds of the invention with substantially minimal or zero bystander effect avoid this disadvantage and selectively ablate cells which express the AKR1C3 enzyme.

SN27686, a close analogue of PR-104A, is reported to have a substantial bystander effect of 48% in mixed MCLs that only express 1% of the activating reductase *E. coli* NfsB (Singleton et al., Cancer Gene Therapy, 14, 953-967, 2007). Example 8 and FIG. 4 demonstrate that compound 641 of the invention exhibits a much lower bystander effect efficiency of approximately 28% in mixed MCLs expressing a 5-fold greater proportion of activating reductase (5% AKR1C3) thus minimising AKR1C3-negative cell ablation. Accordingly, the present invention provides AKR1C3-activated compounds which exhibit a bystander effect that is substantially less than the bystander effect of SN27686.

Exemplary Compounds

Provided below are exemplary compounds of Formula (I) of the invention. This list is not intended to be exhaustive and it will be appreciated that further compounds are included within the scope of the invention as claimed.

N,N-bis(2-bromoethyl)-4-nitro-2-(piperazin-1-ylsulfonyl) aniline (562)
N,N-bis(2-bromoethyl)-2-((4-methylpiperazin-1-yl)sulfonyl)-4-nitroaniline (563)
N,N-bis(2-bromoethyl)-2-((4-ethylpiperazin-1-yl)sulfonyl)-4-nitroaniline (564)
2-(4-((2-(bis(2-bromoethyl)amino)-5-nitrophenyl)sulfonyl)piperazin-1-yl)ethanol (565)
3-(4-((2-(bis(2-bromoethyl)amino)-5-nitrophenyl)sulfonyl)piperazin-1-yl)propane-1,2-diol (566)
N,N-bis(2-bromoethyl)-2-((4-methyl-1,4-diazepan-1-yl)sulfonyl)-4-nitroaniline (584)
N,N-bis(2-bromoethyl)-2-((5-methyl-1,5-diazocan-1-yl)sulfonyl)-4-nitroaniline (585)
N,N-bis(2-bromoethyl)-2-((1-methylpiperidin-4-yl)sulfonyl)-4-nitroaniline (586)
1-((2-(bis(2-bromoethyl)amino)-5-nitrophenyl)sulfonyl)piperidin-4-amine (587)
1-((2-(bis(2-bromoethyl)amino)-5-nitrophenyl)sulfonyl)-N,N-dimethylpiperidin-4-amine (588)
N,N-bis(2-bromoethyl)-2-((1-methylazepan-4-yl)sulfonyl)-4-nitroaniline (589)
N,N-bis(2-bromoethyl)-2-((1-methylazocan-5-yl)sulfonyl)-4-nitroaniline (590)
N,N-bis(2-bromoethyl)-2-(morpholinosulfonyl)-4-nitroaniline (591)
2-(bis(2-bromoethyl)amino)-N-(2-(dimethylamino)ethyl)-5-nitrobenzenesulfonamide (592)
2-(bis(2-bromoethyl)amino)-N-(2-(dimethylamino)ethyl)-N-methyl-5-nitrobenzenesulfonamide (593)
2-(bis(2-bromoethyl)amino)-N-(2-morpholinoethyl)-5-nitrobenzenesulfonamide (594)
2-(bis(2-bromoethyl)amino)-N-methyl-N-(2-morpholinoethyl)-5-nitrobenzenesulfonamide (595)
2-((2-bromoethyl)(4-nitro-2-(piperazin-1-ylsulfonyl)phenyl)amino)ethyl methanesulfonate (601)
2-((2-bromoethyl)(2-((4-methylpiperazin-1-yl)sulfonyl)-4-nitrophenyl)amino)ethyl methanesulfonate (602)
2-((2-bromoethyl)(2-((4-ethylpiperazin-1-yl)sulfonyl)-4-nitrophenyl)amino)ethyl methanesulfonate (603)
2-((2-bromoethyl)(2-((4-(2-hydroxyethyl)piperazin-1-yl)sulfonyl)-4-nitrophenyl)amino)ethyl methanesulfonate (604)
2-((2-bromoethyl)(2-((4-(2,3-dihydroxypropyl)piperazin-1-yl)sulfonyl)-4-nitrophenyl)amino)ethyl methanesulfonate (605)
2-((2-bromoethyl)(2-((4-methyl-1,4-diazepan-1-yl)sulfonyl)-4-nitrophenyl)amino)ethyl methanesulfonate (623)
2-((2-bromoethyl)(2-((5-methyl-1,5-diazocan-1-yl)sulfonyl)-4-nitrophenyl)amino)ethyl methanesulfonate (624)
2-((2-bromoethyl)(2-((1-methylpiperidin-4-yl)sulfonyl)-4-nitrophenyl)amino)ethyl methanesulfonate (625)
2-((2-((4-aminopiperidin-1-yl)sulfonyl)-4-nitrophenyl)(2-bromoethyl)amino)ethyl methanesulfonate (626)
2-((2-bromoethyl)(2-((4-(dimethylamino)piperidin-1-yl)sulfonyl)-4-nitrophenyl)amino)ethyl methanesulfonate (627)
2-((2-bromoethyl)(2-((1-methylazepan-4-yl)sulfonyl)-4-nitrophenyl)amino)ethyl methanesulfonate (628)
2-((2-bromoethyl)(2-((1-methylazocan-5-yl)sulfonyl)-4-nitrophenyl)amino)ethyl methanesulfonate (629)
2-((2-bromoethyl)(2-(morpholinosulfonyl)-4-nitrophenyl)amino)ethyl methanesulfonate (630)
2-((2-bromoethyl)(2-(N-(2-(dimethylamino)ethyl)sulfamoyl)-4-nitrophenyl)amino)ethyl methanesulfonate (631)
2-((2-bromoethyl)(2-(N-(2-(dimethylamino)ethyl)-N-methylsulfamoyl)-4-nitrophenyl)amino)ethyl methanesulfonate (632)
2-((2-bromoethyl)(2-(N-(2-morpholinoethyl)sulfamoyl)-4-nitrophenyl)amino)ethyl methanesulfonate (633)
2-((2-bromoethyl)(2-(N-methyl-N-(2-morpholinoethyl)sulfamoyl)-4-nitrophenyl)amino)ethyl methanesulfonate (634)
((4-nitro-2-(piperazin-1-ylsulfonyl)phenyl)azanediyl)bis(ethane-2,1-diyl) dimethanesulfonate (640)
((2-((4-methylpiperazin-1-yl)sulfonyl)-4-nitrophenyl)azanediyl)bis(ethane-2,1-diyl) dimethanesulfonate (641)
((2-((4-ethylpiperazin-1-yl)sulfonyl)-4-nitrophenyl)azanediyl)bis(ethane-2,1-diyl) dimethanesulfonate (642)
((2-((4-(2-hydroxyethyl)piperazin-1-yl)sulfonyl)-4-nitrophenyl)azanediyl)bis(ethane-2,1-diyl) dimethanesulfonate (643)
((2-((4-(2,3-dihydroxypropyl)piperazin-1-yl)sulfonyl)-4-nitrophenyl)azanediyl)bis(ethane-2,1-diyl) dimethanesulfonate (644)
((2-((4-methyl-1,4-diazepan-1-yl)sulfonyl)-4-nitrophenyl)azanediyl)bis(ethane-2,1-diyl) dimethanesulfonate (662)
((2-((5-methyl-1,5-diazocan-1-yl)sulfonyl)-4-nitrophenyl)azanediyl)bis(ethane-2,1-diyl) dimethanesulfonate (663)

((2-((1-methylpiperidin-4-yl)sulfonyl)-4-nitrophenyl) azanediyl)bis(ethane-2,1-diyl) dimethanesulfonate (664)

((2-((4-aminopiperidin-1-yl)sulfonyl)-4-nitrophenyl) azanediyl)bis(ethane-2,1-diyl) dimethanesulfonate (665)

((2-((4-(dimethylamino)piperidin-1-yl)sulfonyl)-4-nitrophenyl)azanediyl)bis(ethane-2,1-diyl) dimethanesulfonate (666)

((2-((1-methylazepan-4-yl)sulfonyl)-4-nitrophenyl) azanediyl)bis(ethane-2,1-diyl) dimethanesulfonate (667)

((2-((1-methylazocan-5-yl)sulfonyl)-4-nitrophenyl) azanediyl)bis(ethane-2,1-diyl) dimethanesulfonate (668)

((2-(morpholinosulfonyl)-4-nitrophenyl)azanediyl)bis(ethane-2,1-diyl) dimethanesulfonate (669)

((2-(N-(2-(dimethylamino)ethyl)sulfamoyl)-4-nitrophenyl) azanediyl)bis(ethane-2,1-diyl) dimethanesulfonate (670)

((2-(N-(2-(dimethylamino)ethyl)-N-methylsulfamoyl)-4-nitrophenyl)azanediyl)bis(ethane-2,1-diyl) dimethanesulfonate (671)

((2-(N-(2-morpholinoethyl)sulfamoyl)-4-nitrophenyl) azanediyl)bis(ethane-2,1-diyl) dimethanesulfonate (672)

((2-(N-methyl-N-(2-morpholinoethyl)sulfamoyl)-4-nitrophenyl)azanediyl)bis(ethane-2,1-diyl) dimethanesulfonate (673)

N,N-bis(2-bromoethyl)-2-methyl-4-nitro-6-(piperazin-1-ylsulfonyl)aniline (679)

N,N-bis(2-bromoethyl)-2-methyl-6-((4-methylpiperazin-1-yl)sulfonyl)-4-nitroaniline (680)

N,N-bis(2-bromoethyl)-2-((4-ethylpiperazin-1-yl)sulfonyl)-6-methyl-4-nitroaniline (681)

3-(4-((2-(bis(2-bromoethyl)amino)-3-methyl-5-nitrophenyl) sulfonyl)piperazin-1-yl)propane-1,2-diol (683)

N,N-bis(2-bromoethyl)-2-methyl-6-((4-methyl-1,4-diazepan-1-yl)sulfonyl)-4-nitroaniline (701)

N,N-bis(2-bromoethyl)-2-methyl-6-((5-methyl-1,5-diazocan-1-yl)sulfonyl)-4-nitroaniline (702)

N,N-bis(2-bromoethyl)-2-methyl-6-((1-methylpiperidin-4-yl)sulfonyl)-4-nitroaniline (703)

1-((2-(bis(2-bromoethyl)amino)-3-methyl-5-nitrophenyl) sulfonyl)piperidin-4-amine (704)

1-((2-(bis(2-bromoethyl)amino)-3-methyl-5-nitrophenyl) sulfonyl)-N,N-dimethylpiperidin-4-amine (705)

2-((2-bromoethyl)(2-methyl-4-nitro-6-(piperazin-1-ylsulfonyl)phenyl)amino)ethyl methanesulfonate (718)

2-((2-bromoethyl)(2-methyl-6-((4-methylpiperazin-1-yl) sulfonyl)-4-nitrophenyl)amino)ethylmethanesulfonate (719)

2-((2-bromoethyl)(2-((4-ethylpiperazin-1-yl)sulfonyl)-6-methyl-4-nitrophenyl)amino)ethyl methanesulfonate (720)

2-((2-bromoethyl)(2-((4-(2,3-dihydroxypropyl)piperazin-1-yl)sulfonyl)-6-methyl-4-nitrophenyl)amino)ethyl methanesulfonate (722)

2-((2-bromoethyl)(2-methyl-6-((4-methyl-1,4-diazepan-1-yl)sulfonyl)-4-nitrophenyl)amino)ethyl methanesulfonate (740)

2-((2-bromoethyl)(2-methyl-6-((5-methyl-1,5-diazocan-1-yl)sulfonyl)-4-nitrophenyl)amino)ethyl methanesulfonate (741)

2-((2-bromoethyl)(2-methyl-6-((1-methylpiperidin-4-yl) sulfonyl)-4-nitrophenyl)amino)ethyl methanesulfonate (742)

2-((2-((4-aminopiperidin-1-yl)sulfonyl)-6-methyl-4-nitrophenyl)(2-bromoethyl)amino)ethyl methanesulfonate (743)

2-((2-bromoethyl)(2-((4-(dimethylamino)piperidin-1-yl) sulfonyl)-6-methyl-4-nitrophenyl)amino)ethyl methanesulfonate (744)

((2-methyl-4-nitro-6-(piperazin-1-ylsulfonyl)phenyl) azanediyl)bis(ethane-2,1-diyl) dimethanesulfonate (757)

((2-methyl-6-((4-methylpiperazin-1-yl)sulfonyl)-4-nitrophenyl)azanediyl)bis(ethane-2,1-diyl) dimethanesulfonate (758)

((2-((4-ethylpiperazin-1-yl)sulfonyl)-6-methyl-4-nitrophenyl)azanediyl)bis(ethane-2,1-diyl) dimethanesulfonate (759)

((2-((4-(2,3-dihydroxypropyl)piperazin-1-yl)sulfonyl)-6-methyl-4-nitrophenyl)azanediyl)bis(ethane-2,1-diyl) dimethanesulfonate (761)

((2-methyl-6-((4-methyl-1,4-diazepan-1-yl)sulfonyl)-4-nitrophenyl)azanediyl)bis(ethane-2,1-diyl) dimethanesulfonate (779)

((2-methyl-6-((5-methyl-1,5-diazocan-1-yl)sulfonyl)-4-nitrophenyl)azanediyl)bis(ethane-2,1-diyl) dimethanesulfonate (780)

((2-methyl-6-((1-methylpiperidin-4-yl)sulfonyl)-4-nitrophenyl)azanediyl)bis(ethane-2,1-diyl) dimethanesulfonate (781)

((2-((4-aminopiperidin-1-yl)sulfonyl)-6-methyl-4-nitrophenyl)azanediyl)bis(ethane-2,1-diyl) dimethanesulfonate (782)

((2-((4-(dimethylamino)piperidin-1-yl)sulfonyl)-6-methyl-4-nitrophenyl)azanediyl)bis(ethane-2,1-diyl) dimethanesulfonate (783)

2-((2-bromoethyl)(2,4-dinitro-6-(piperazin-1-ylsulfonyl) phenyl)amino)ethyl methanesulfonate (835)

2-((2-bromoethyl)(2-((4-methylpiperazin-1-yl)sulfonyl)-4, 6-dinitrophenyl)amino)ethyl methanesulfonate (836)

2-((2-bromoethyl)(2-((4-ethylpiperazin-1-yl)sulfonyl)-4,6-dinitrophenyl)amino)ethyl methanesulfonate (837)

2-((2-bromoethyl)(2-((4-(2,3-dihydroxypropyl)piperazin-1-yl)sulfonyl)-4,6-dinitrophenyl)amino)ethyl methanesulfonate (839)

2-((2-bromoethyl)(2-((4-methyl-1,4-diazepan-1-yl)sulfonyl)-4,6-dinitrophenyl)amino)ethyl methanesulfonate (857)

2-((2-bromoethyl)(2-((5-methyl-1,5-diazocan-1-yl)sulfonyl)-4,6-dinitrophenyl)amino)ethyl methanesulfonate (858)

2-((2-((4-aminopiperidin-1-yl)sulfonyl)-4,6-dinitrophenyl) (2-bromoethyl)amino)ethyl methanesulfonate (860)

2-((2-bromoethyl)(2-((4-(dimethylamino)piperidin-1-yl) sulfonyl)-4,6-dinitrophenyl)amino)ethyl methanesulfonate (861)

((2,4-dinitro-6-(piperazin-1-ylsulfonyl)phenyl)azanediyl) bis(ethane-2,1-diyl) dimethanesulfonate (874)

((2-((4-methylpiperazin-1-yl)sulfonyl)-4,6-dinitrophenyl) azanediyl)bis(ethane-2,1-diyl) dimethanesulfonate (875)

((2-((4-ethylpiperazin-1-yl)sulfonyl)-4,6-dinitrophenyl) azanediyl)bis(ethane-2,1-diyl) dimethanesulfonate (876)

((2-((4-methyl-1,4-diazepan-1-yl)sulfonyl)-4,6-dinitrophenyl)azanediyl)bis(ethane-2,1-diyl) dimethanesulfonate (896)

((2-((5-methyl-1,5-diazocan-1-yl)sulfonyl)-4,6-dinitrophenyl)azanediyl)bis(ethane-2,1-diyl) dimethanesulfonate (897)

((2-((4-aminopiperidin-1-yl)sulfonyl)-4,6-dinitrophenyl) azanediyl)bis(ethane-2,1-diyl) dimethanesulfonate (899)

((2-((4-(dimethylamino)piperidin-1-yl)sulfonyl)-4,6-dinitrophenyl)azanediyl)bis(ethane-2,1-diyl) dimethanesulfonate (900)

2-((2-bromoethyl)(4-nitro-2-(piperazin-1-ylsulfonyl)-6-(trifluoromethyl)phenyl)amino)ethyl methanesulfonate (952)

2-((2-bromoethyl)(2-((4-methylpiperazin-1-yl)sulfonyl)-4-nitro-6-(trifluoromethyl)phenyl)amino)ethyl methanesulfonate (953)

2-((2-bromoethyl)(2-((4-ethylpiperazin-1-yl)sulfonyl)-4-nitro-6-(trifluoromethyl)phenyl)amino)ethyl methanesulfonate (954)

2-((2-bromoethyl)(2-((4-(2,3-dihydroxypropyl)piperazin-1-yl)sulfonyl)-4-nitro-6-(trifluoromethyl)phenyl)amino)ethyl methanesulfonate (956)

2-((2-bromoethyl)(2-((4-methyl-1,4-diazepan-1-yl)sulfonyl)-4-nitro-6-(trifluoromethyl)phenyl)amino)ethyl methanesulfonate (974)

2-((2-bromoethyl)(2-((5-methyl-1,5-diazocan-1-yl)sulfonyl)-4-nitro-6-(trifluoromethyl)phenyl)amino)ethyl methanesulfonate (975)

2-((2-((4-aminopiperidin-1-yl)sulfonyl)-4-nitro-6-(trifluoromethyl)phenyl)(2-bromoethyl)amino)ethyl methanesulfonate (977)

2-((2-bromoethyl)(2-((4-(dimethylamino)piperidin-1-yl)sulfonyl)-4-nitro-6-(trifluoromethyl)phenyl)amino)ethyl methanesulfonate (978)

((4-nitro-2-(piperazin-1-ylsulfonyl)-6-(trifluoromethyl)phenyl)azanediyl)bis(ethane-2,1-diyl) dimethanesulfonate (991)

((2-((4-methylpiperazin-1-yl)sulfonyl)-4-nitro-6-(trifluoromethyl)phenyl)azanediyl)bis(ethane-2,1-diyl) dimethanesulfonate (992)

((2-((4-ethylpiperazin-1-yl)sulfonyl)-4-nitro-6-(trifluoromethyl)phenyl)azanediyl)bis(ethane-2,1-diyl) dimethanesulfonate (993)

((2-((4-(2,3-dihydroxypropyl)piperazin-1-yl)sulfonyl)-4-nitro-6-(trifluoromethyl)phenyl)azanediyl)bis(ethane-2,1-diyl) dimethanesulfonate (995)

((2-((4-methyl-1,4-diazepan-1-yl)sulfonyl)-4-nitro-6-(trifluoromethyl)phenyl)azanediyl)bis(ethane-2,1-diyl) dimethanesulfonate (1013)

((2-((5-methyl-1,5-diazocan-1-yl)sulfonyl)-4-nitro-6-(trifluoromethyl)phenyl)azanediyl)bis(ethane-2,1-diyl) dimethanesulfonate (1014)

((2-((4-aminopiperidin-1-yl)sulfonyl)-4-nitro-6-(trifluoromethyl)phenyl)azanediyl)bis(ethane-2,1-diyl) dimethanesulfonate (1016)

((2-((4-(dimethylamino)piperidin-1-yl)sulfonyl)-4-nitro-6-(trifluoromethyl)phenyl)azanediyl)bis(ethane-2,1-diyl) dimethanesulfonate (1017)

2-((2-bromoethyl)(2-ethynyl-4-nitro-6-(piperazin-1-ylsulfonyl)phenyl)amino)ethyl methanesulfonate (1069)

2-((2-bromoethyl)(2-ethynyl-6-((4-methylpiperazin-1-yl)sulfonyl)-4-nitrophenyl)amino)ethyl methanesulfonate (1070)

2-((2-bromoethyl)(2-((4-ethylpiperazin-1-yl)sulfonyl)-6-ethynyl-4-nitrophenyl)amino)ethyl methanesulfonate (1071)

((2-ethynyl-4-nitro-6-(piperazin-1-ylsulfonyl)phenyl)azanediyl)bis(ethane-2,1-diyl) dimethanesulfonate (1108)

((2-ethynyl-6-((4-methylpiperazin-1-yl)sulfonyl)-4-nitrophenyl)azanediyl)bis(ethane-2,1-diyl) dimethanesulfonate (1109)

((2-((4-ethylpiperazin-1-yl)sulfonyl)-6-ethynyl-4-nitrophenyl)azanediyl)bis(ethane-2,1-diyl) dimethanesulfonate (1110)

4-((2-(bis(2-((methylsulfonyl)oxy)ethyl)amino)-5-nitrophenyl)sulfonyl)piperazin-1-ium methanesulfonate (640.Ms)

4-((2-(bis(2-((methylsulfonyl)oxy)ethyl)amino)-5-nitrophenyl)sulfonyl)-1-methylpiperazin-1-ium methanesulfonate (641.Ms)

4-((2-(bis(2-((methylsulfonyl)oxy)ethyl)amino)-5-nitrophenyl)sulfonyl)-1-ethylpiperazin-1-ium methanesulfonate (642.Ms)

4-((2-(bis(2-((methylsulfonyl)oxy)ethyl)amino)-5-nitrophenyl)sulfonyl)-1-(2-hydroxyethyl)piperazin-1-ium methanesulfonate (643.Ms)

4-((2-(bis(2-((methylsulfonyl)oxy)ethyl)amino)-5-nitrophenyl)sulfonyl)-1-(2,3-dihydroxypropyl)piperazin-1-ium methanesulfonate (644.Ms)

4-((2-(bis(2-((methylsulfonyl)oxy)ethyl)amino)-3-methyl-5-nitrophenyl)sulfonyl)piperazin-1-ium methanesulfonate (757.Ms)

4-((2-(bis(2-((methylsulfonyl)oxy)ethyl)amino)-3-methyl-5-nitrophenyl)sulfonyl)-1-methylpiperazin-1-ium methanesulfonate (758.Ms)

4-((2-(bis(2-((methylsulfonyl)oxy)ethyl)amino)-5-nitro-3-(trifluoromethyl)phenyl)sulfonyl)piperazin-1-ium methanesulfonate (991.Ms)

4-((2-(bis(2-((methylsulfonyl)oxy)ethyl)amino)-5-nitro-3-(trifluoromethyl)phenyl)sulfonyl)-1-methylpiperazin-1-ium methanesulfonate (992.Ms)

4-((2-(bis(2-((methylsulfonyl)oxy)ethyl)amino)-3-ethynyl-5-nitrophenyl)sulfonyl)piperazin-1-ium methanesulfonate (1108.Ms)

4-((2-(bis(2-((methylsulfonyl)oxy)ethyl)amino)-3-ethynyl-5-nitrophenyl)sulfonyl)-1-methylpiperazin-1-ium methanesulfonate (1109.Ms)

The following are the chemical structures of some exemplary compounds of the invention.

5-Nitrobenzenesulfonamide dibromo, bromomesylate and bismesylate mustards (562-674):

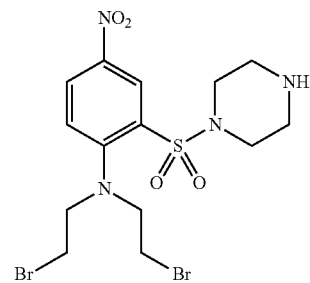

562

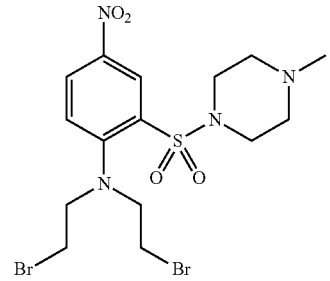

563

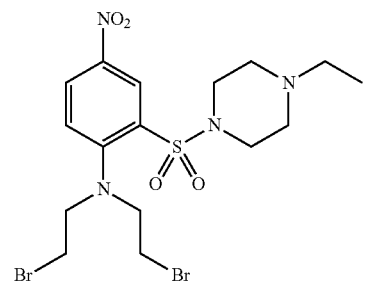

564

565 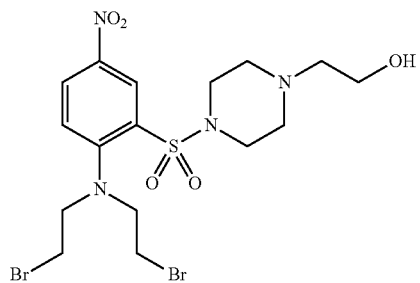
566 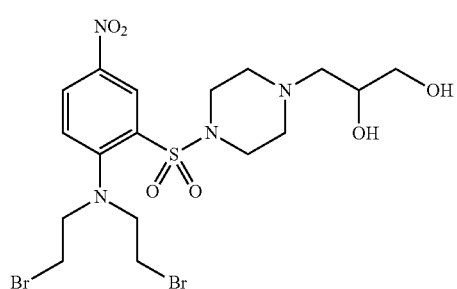
567 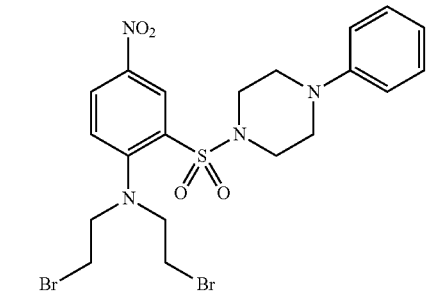
568 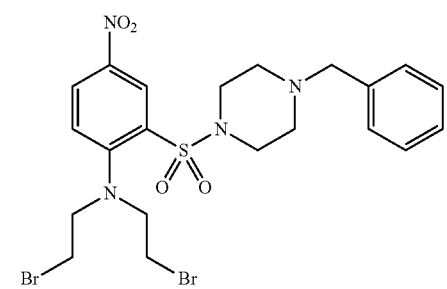
569 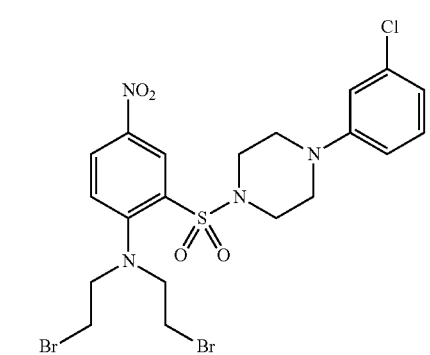
570 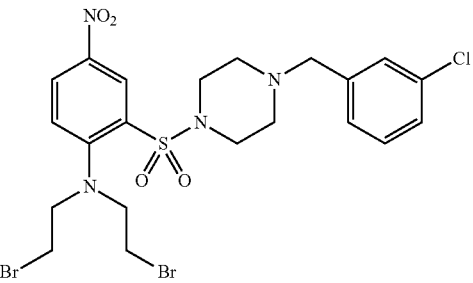
571 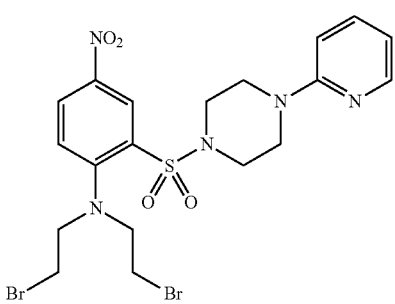
572 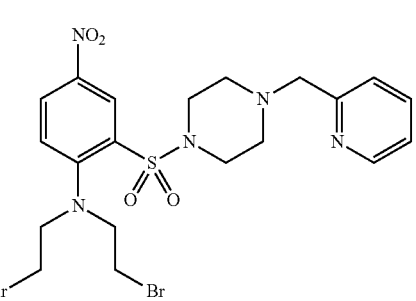
573 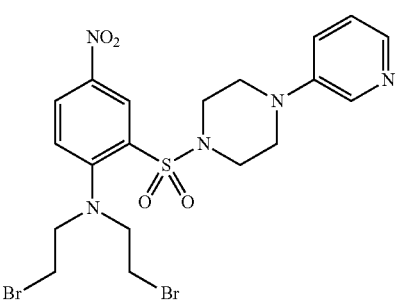
574 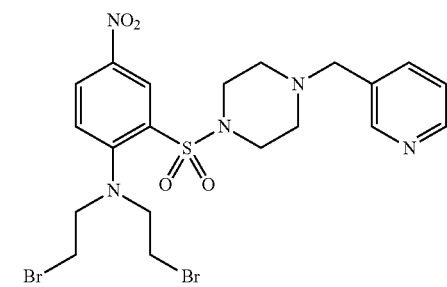

| | |
|---|---|
| 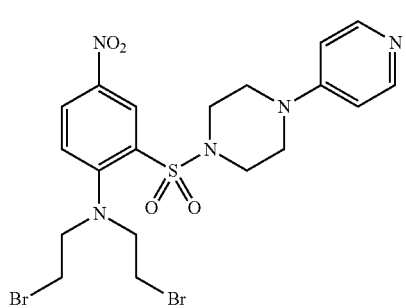 575 | 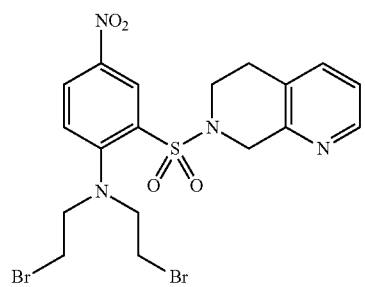 580 |
| 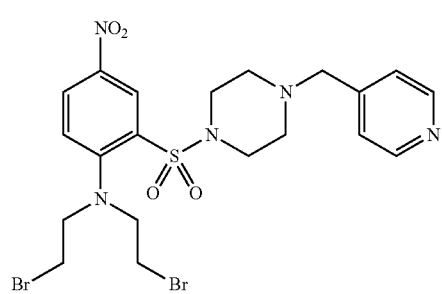 576 | 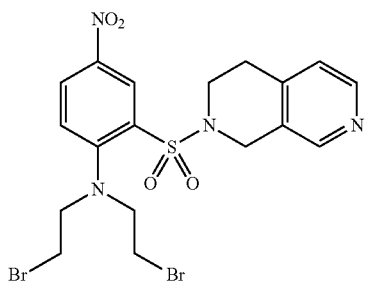 581 |
| 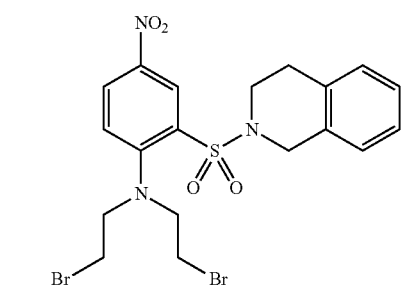 577 | 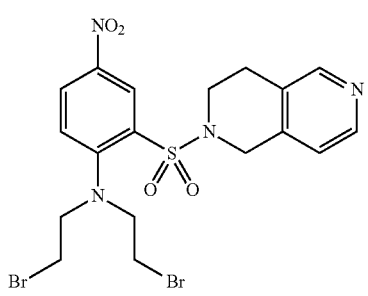 582 |
| 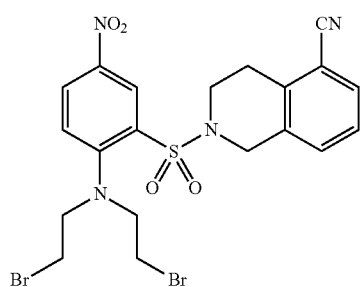 578 | 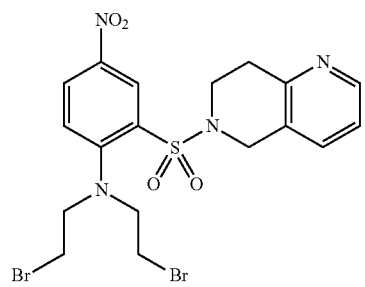 583 |
| 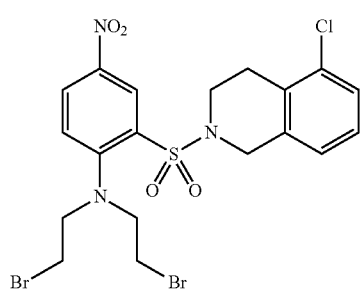 579 | 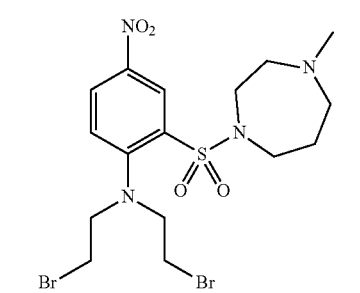 584 |

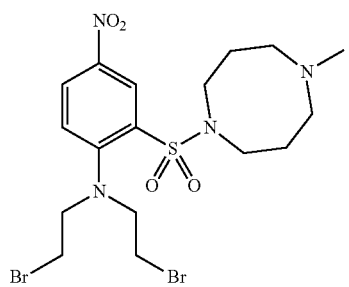
585
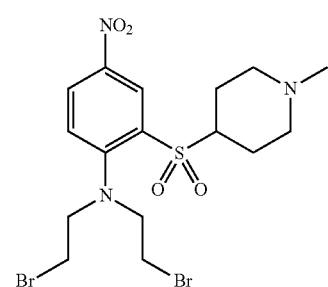
586
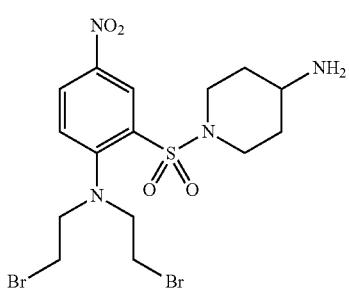
587
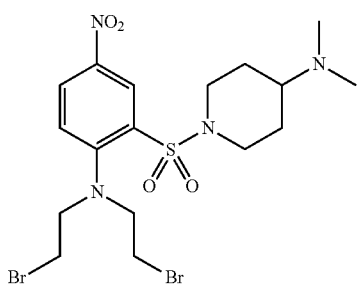
588
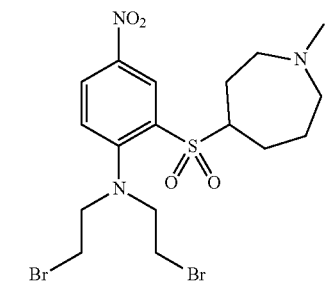
589
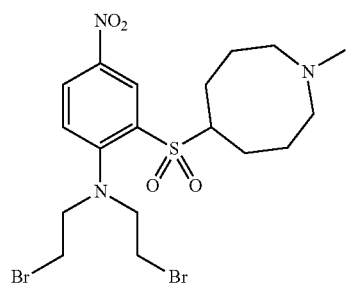
590
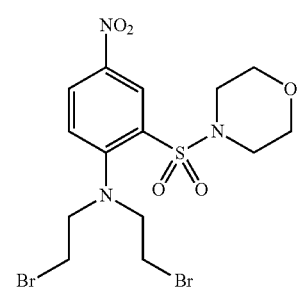
591
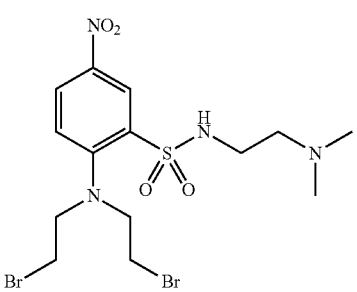
592
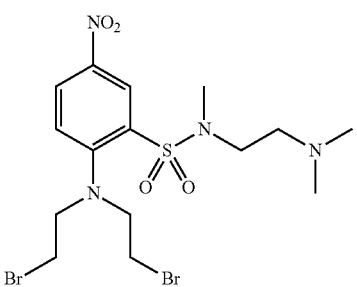
593
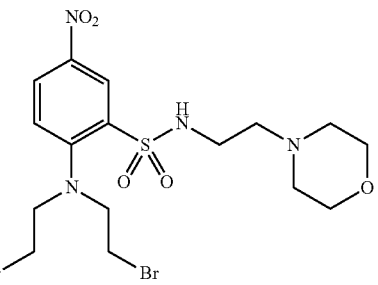
594

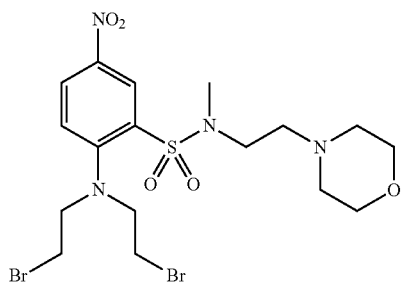
595
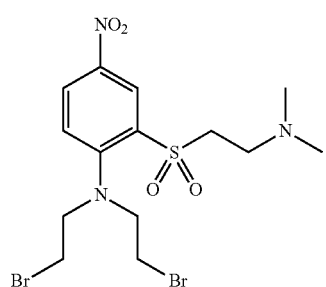
596
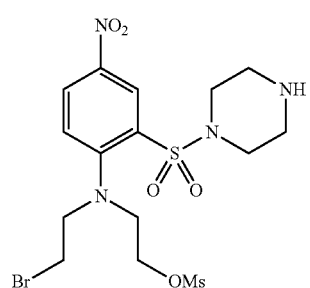
601
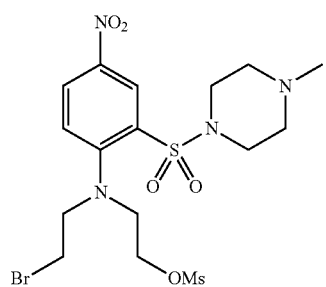
602
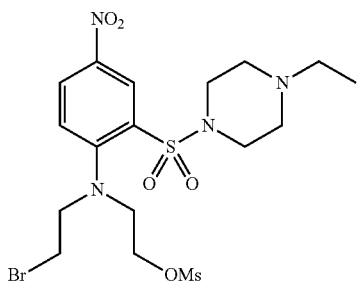
603
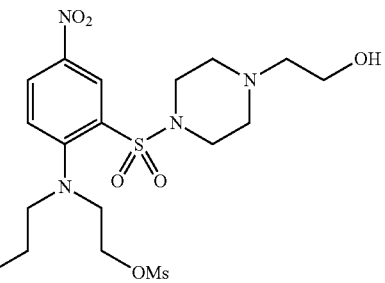
604
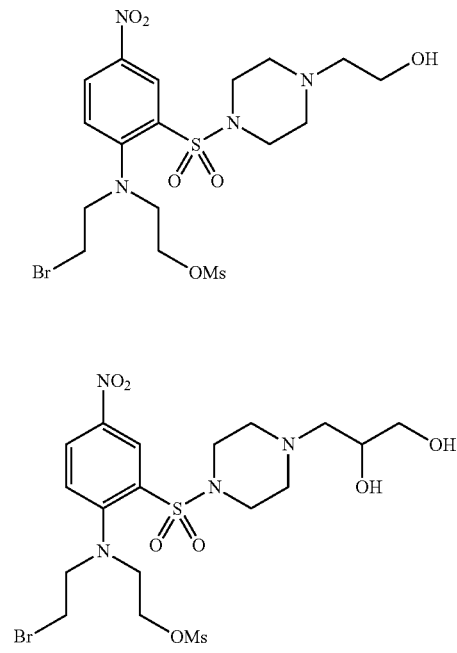
605
606
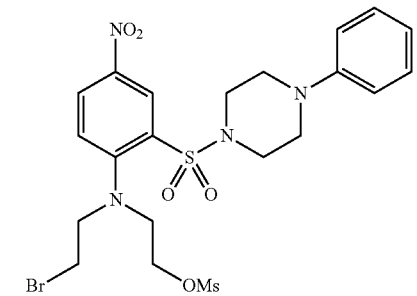
607
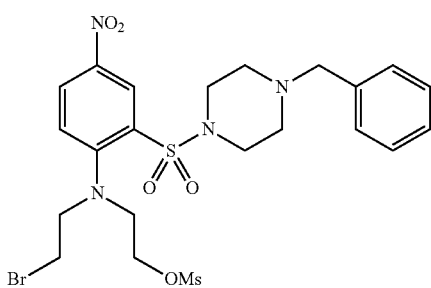
608
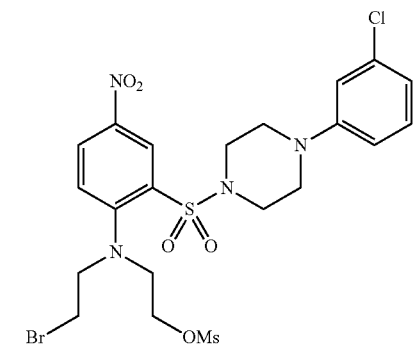

609
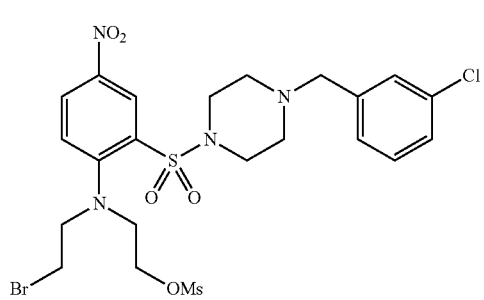
610
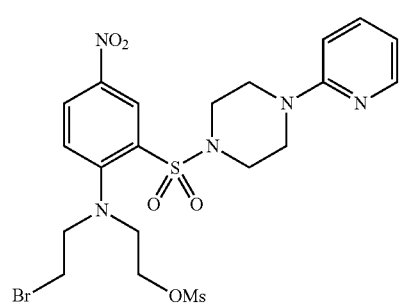
611
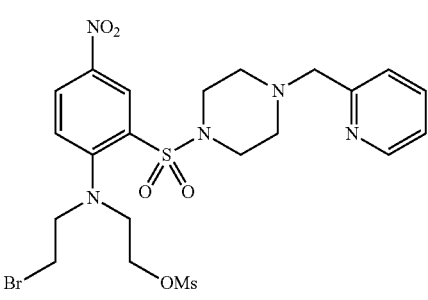
612
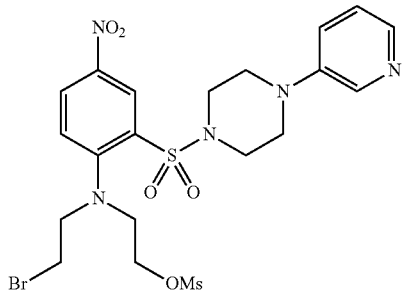
613
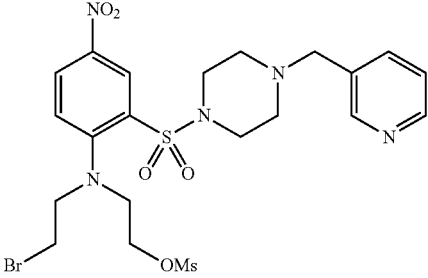
614
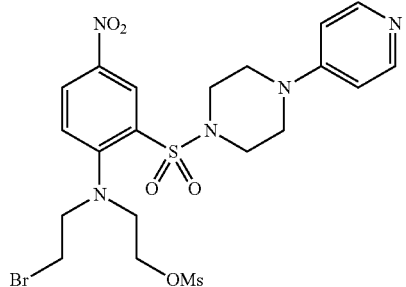
615
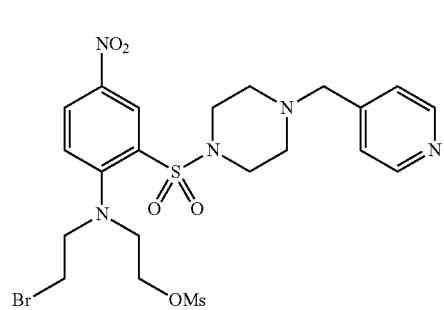
616
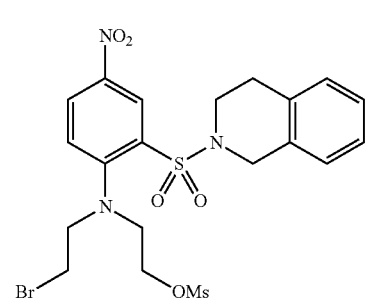
617
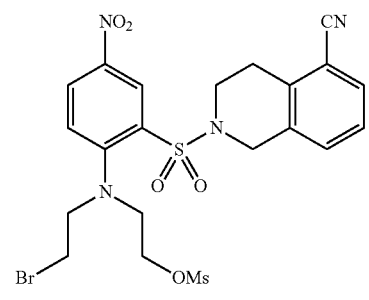
618
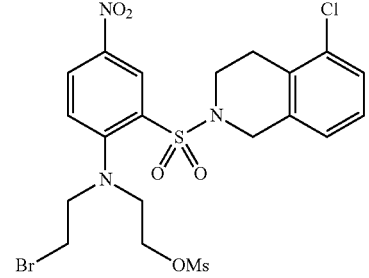

| 619 | 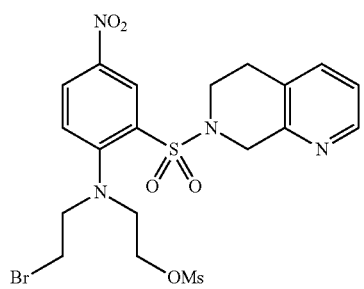 | 624 | 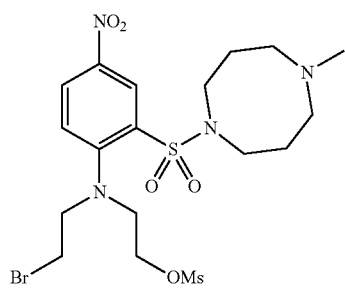 |
| 620 | 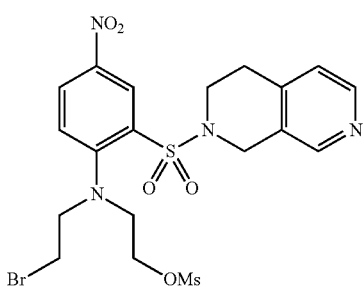 | 625 | 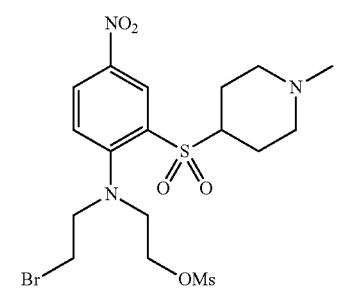 |
| 621 | 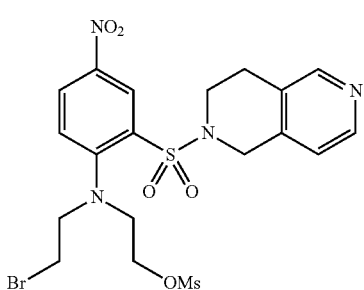 | 626 | 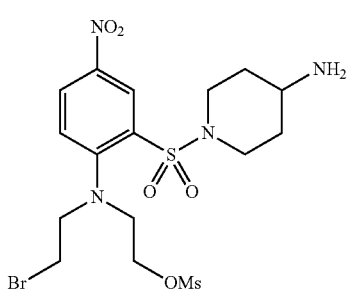 |
| 622 | 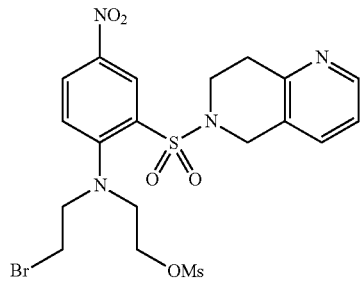 | 627 | 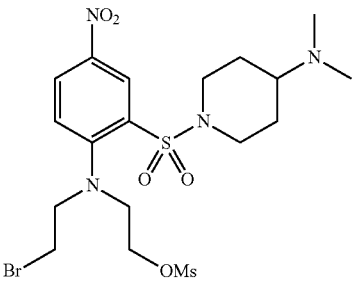 |
| 623 | 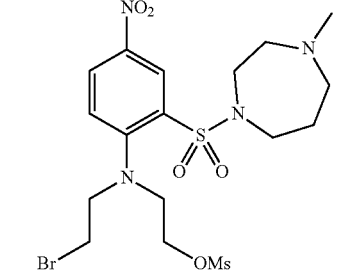 | 628 | 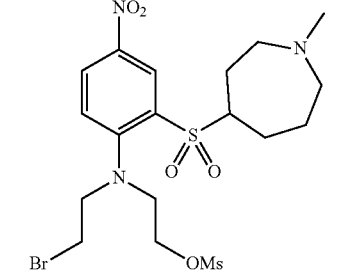 |

629
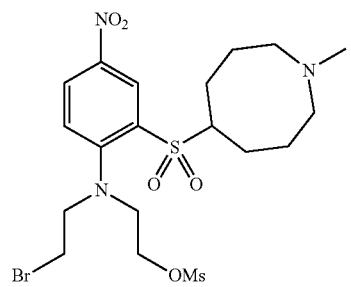
630
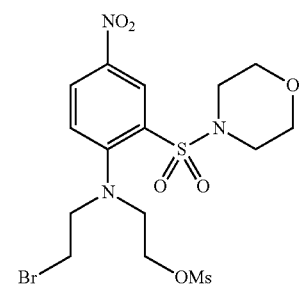
631
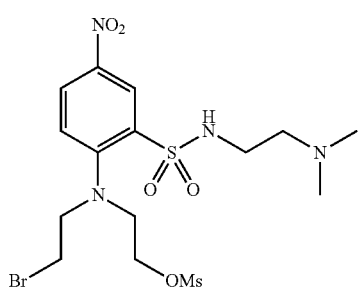
632
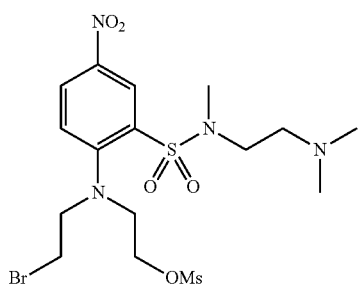
633
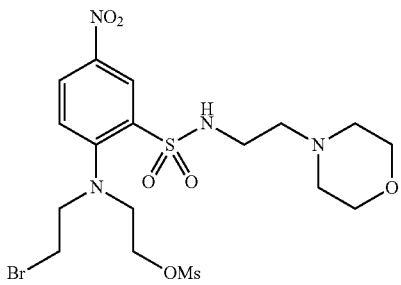
634
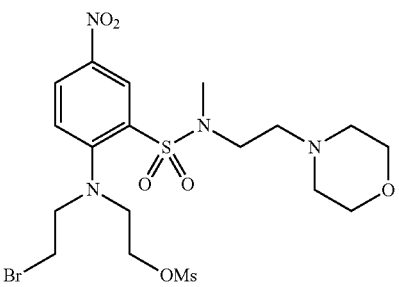
635
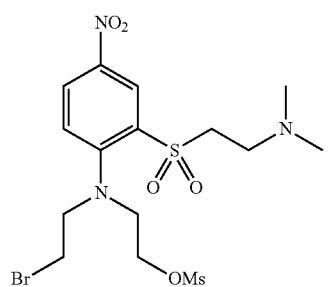
640
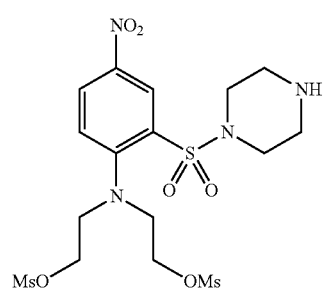
641
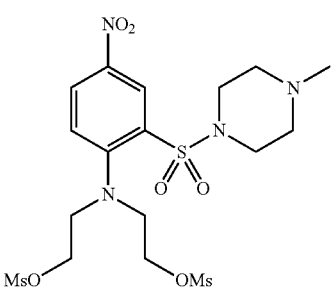
642
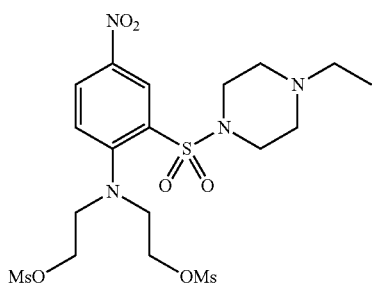

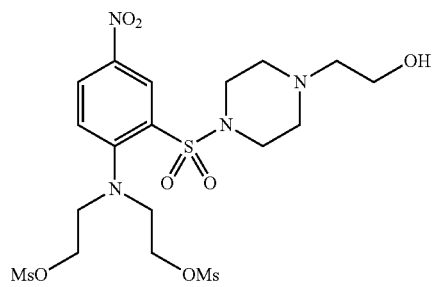
643
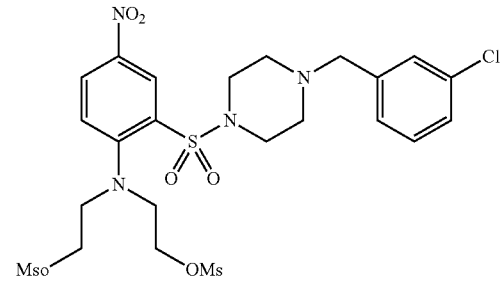
648
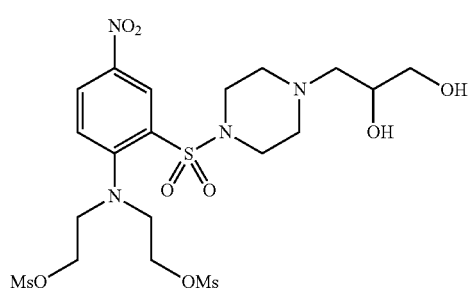
644
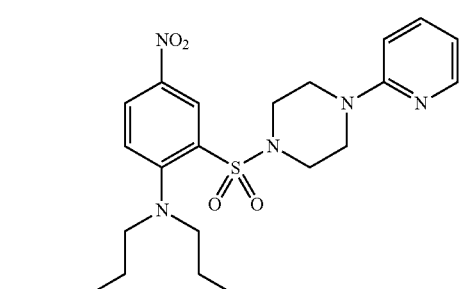
649
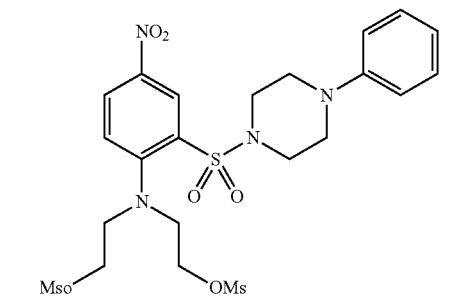
645
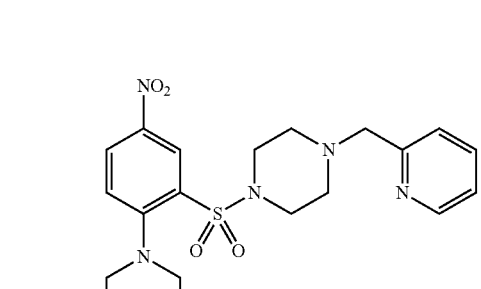
650
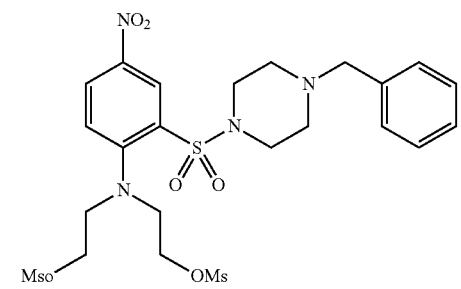
646
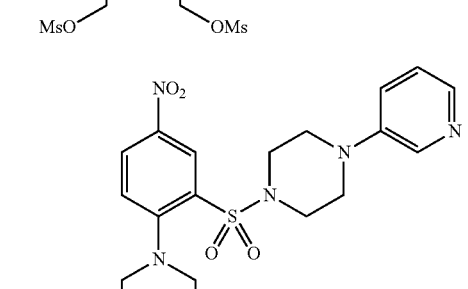
651
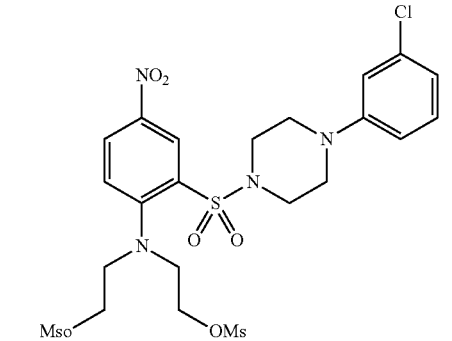
647
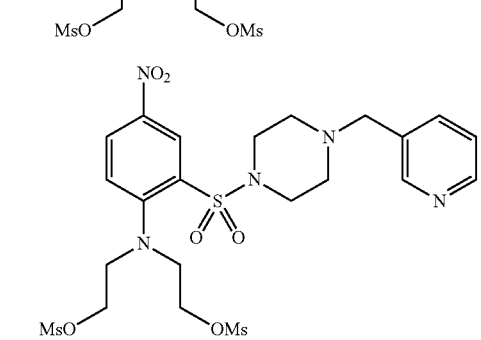
652

653
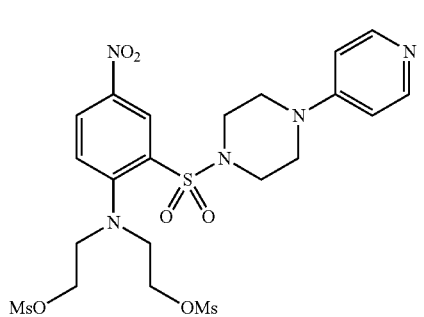
654
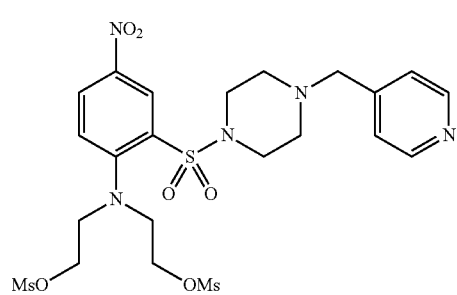
655
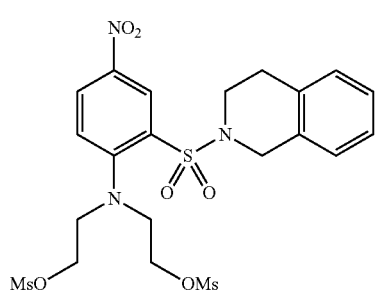
656
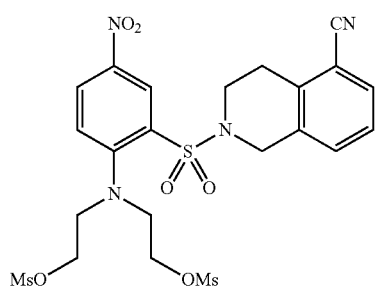
657
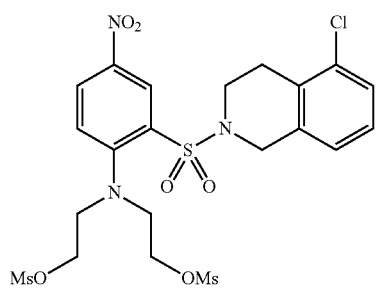
658
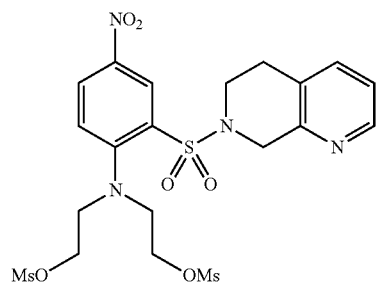
659
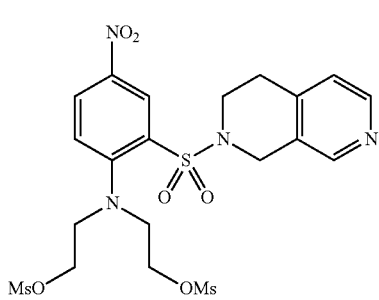
660
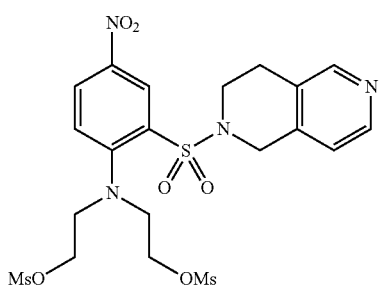
661
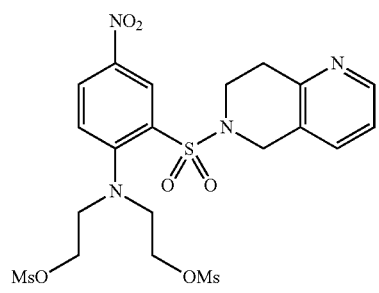
662
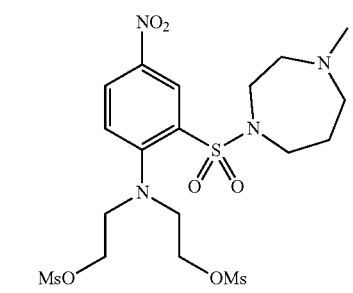

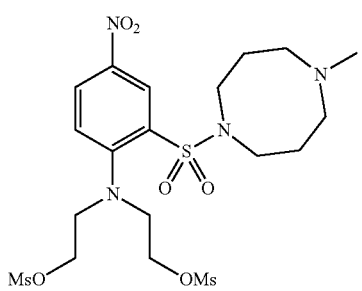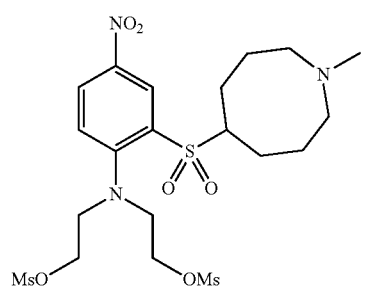

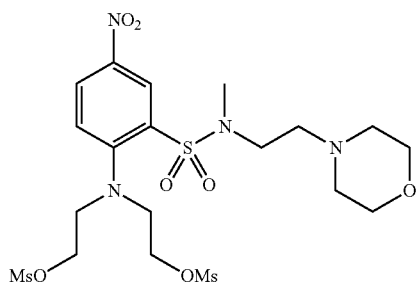
673
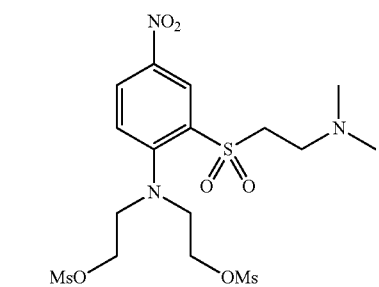
674
3-Methyl-5-nitrobenzenesulfonamide dibromo, bromomesylate and bismesylate mustards (679-791):
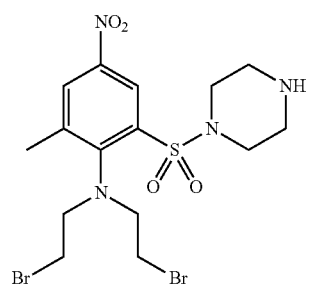
679
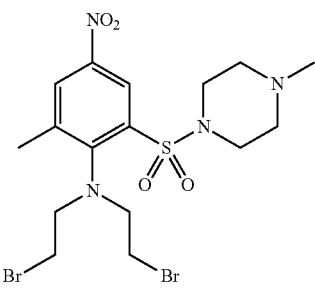
680
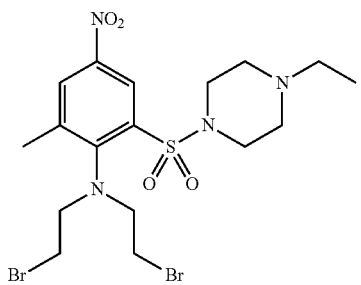
681
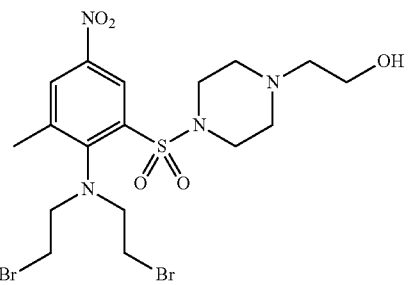
682
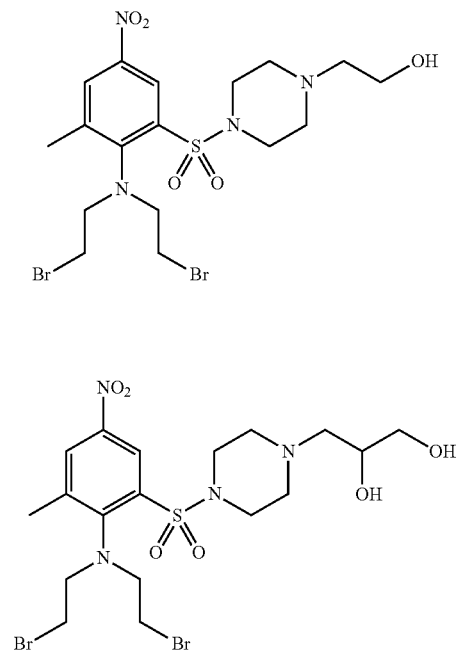
683
684
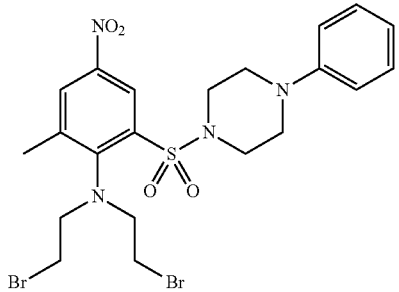
685
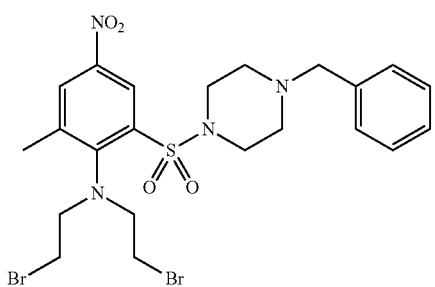
686
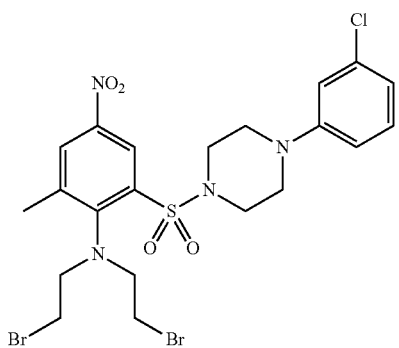

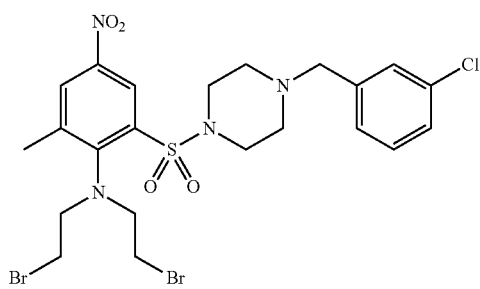
687
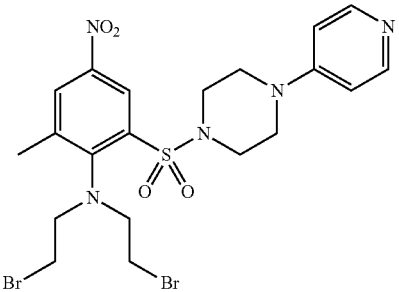
692
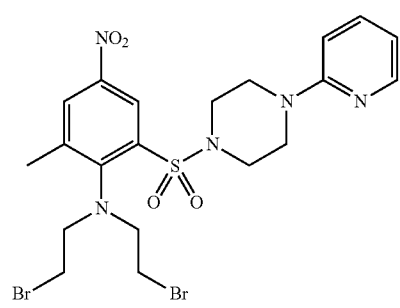
688
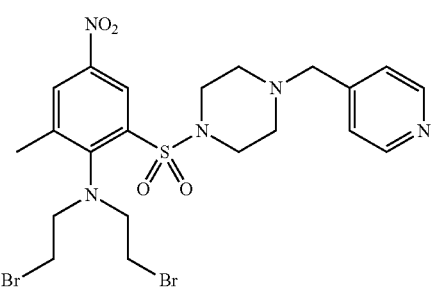
693
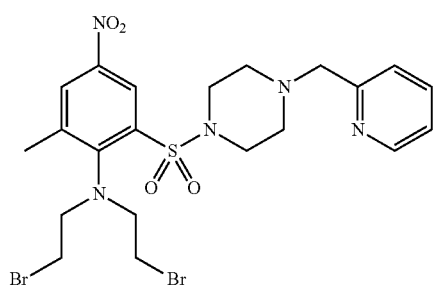
689
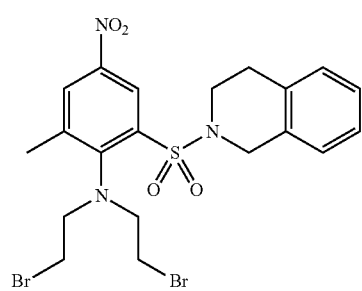
694
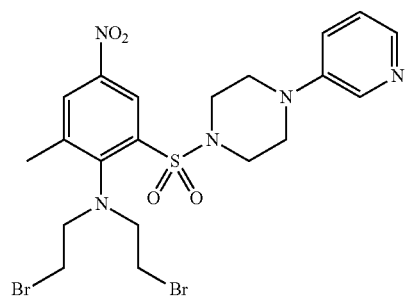
690
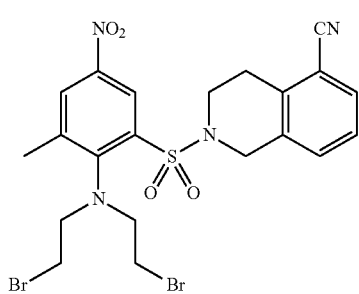
695
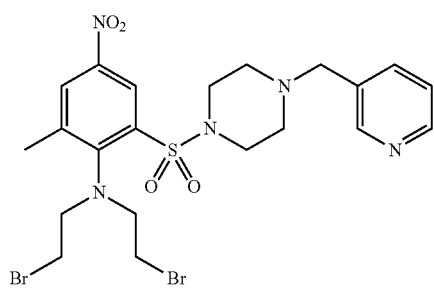
691
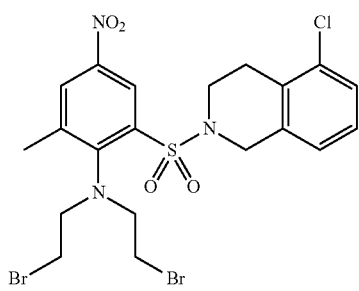
696

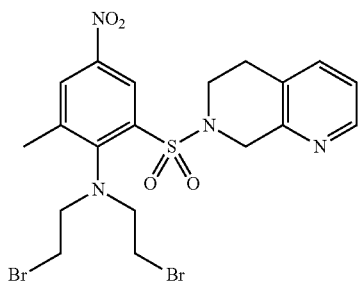
697
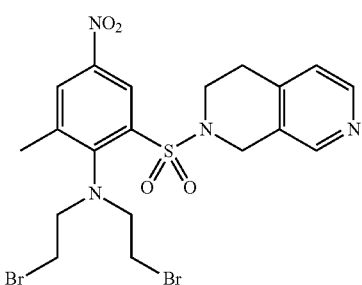
698
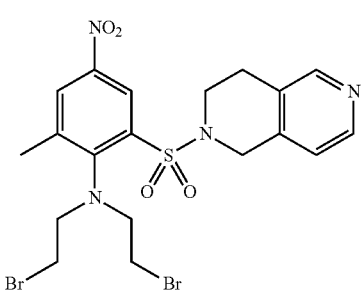
699
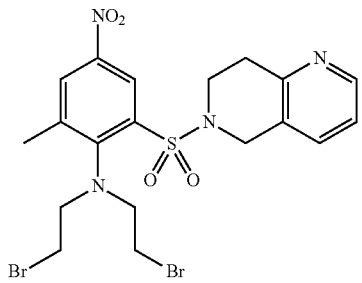
700
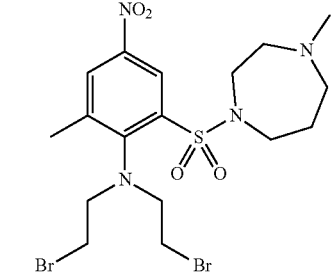
701
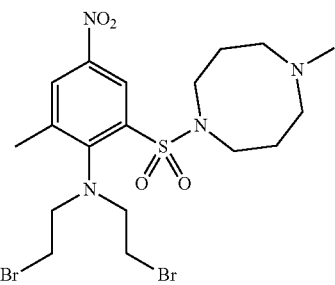
702
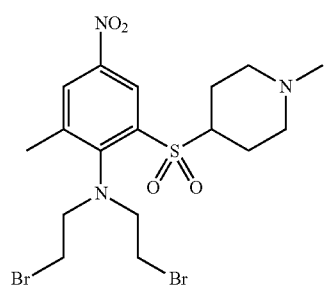
703
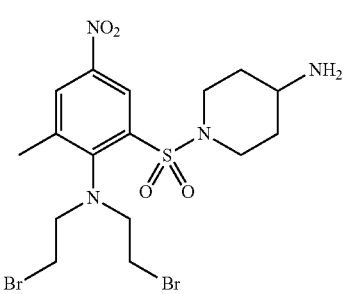
704
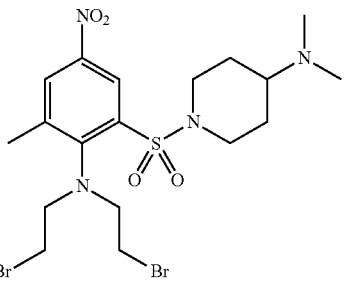
705
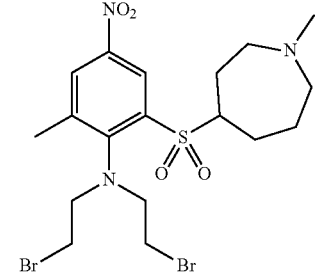
706

| 707 | 712 |
|---|---|
| 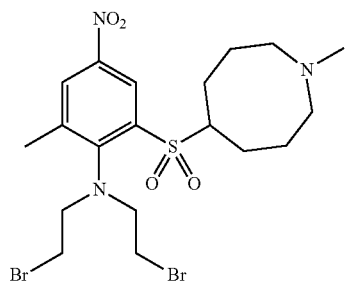 | 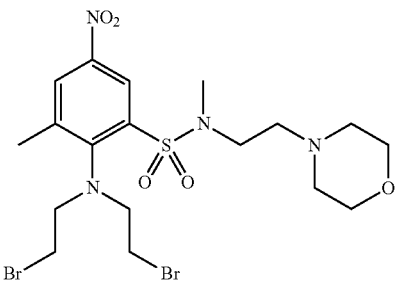 |
| 708 | 713 |
|---|---|
| 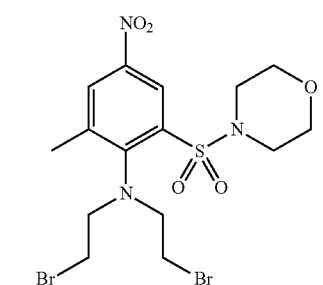 | 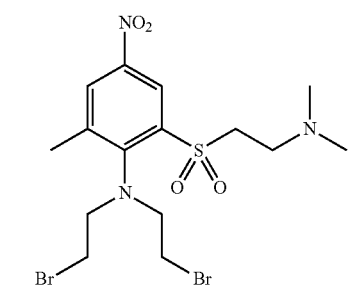 |
| 709 | 718 |
|---|---|
| 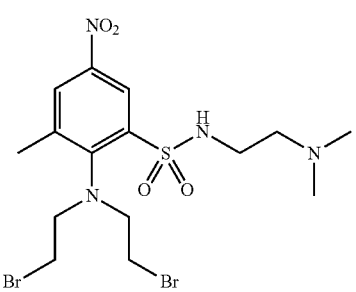 | 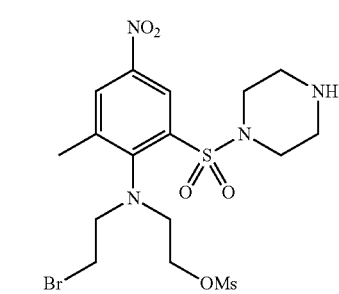 |
| 710 | 719 |
|---|---|
| 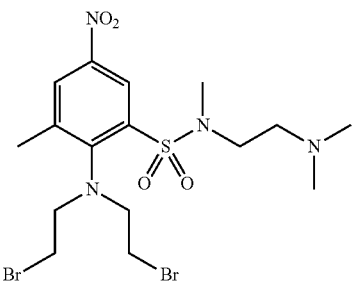 | 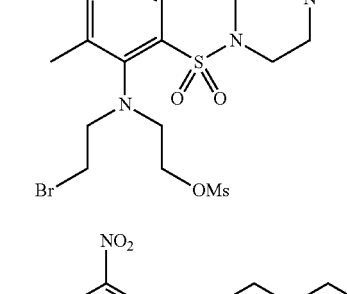 |
| 711 | 720 |
|---|---|
| 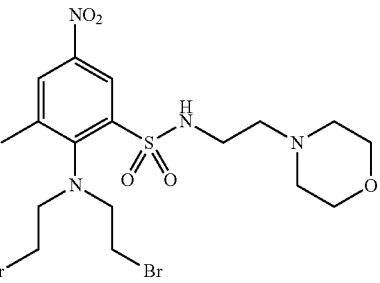 | 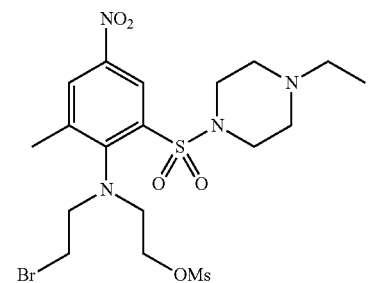 |

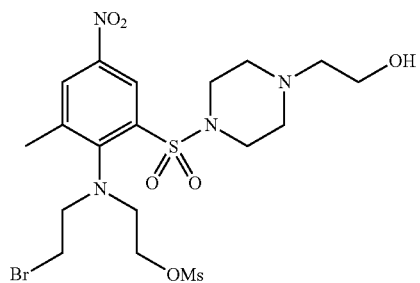
721
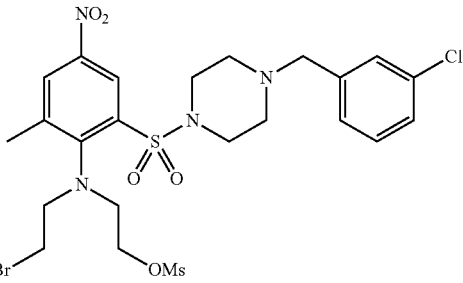
726
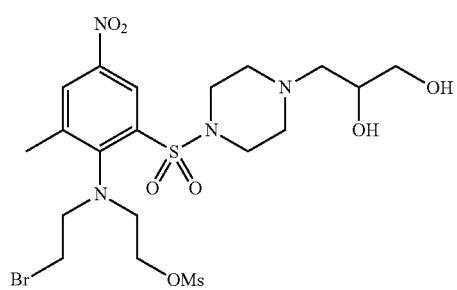
722
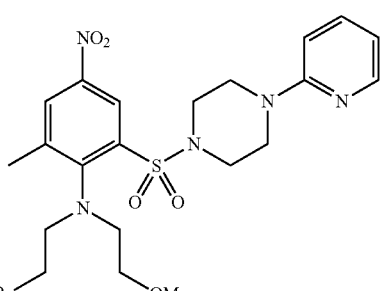
727
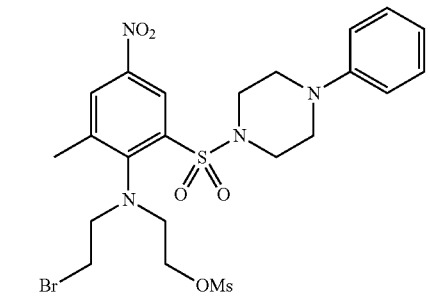
723
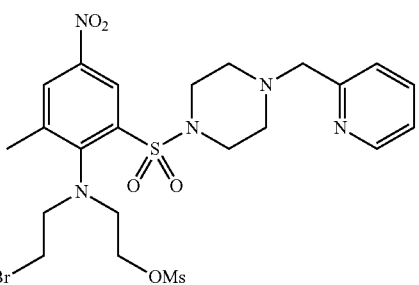
728
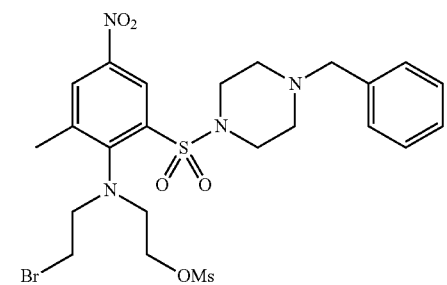
724
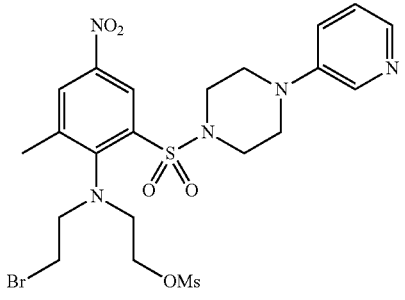
729
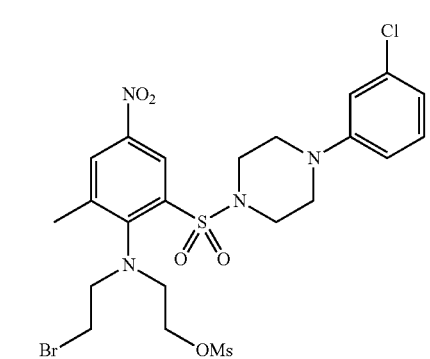
725
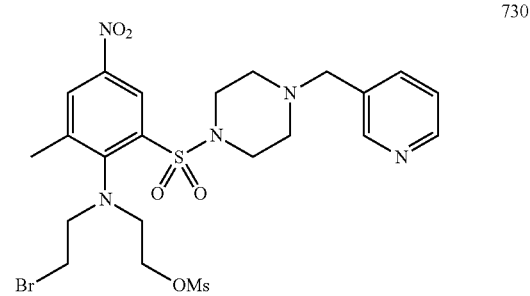
730

| | |
|---|---|
| 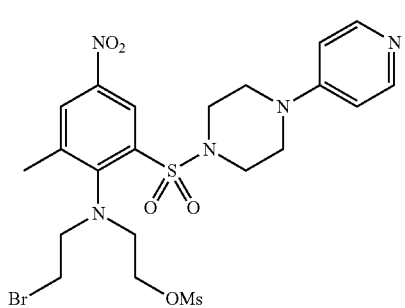 731 | 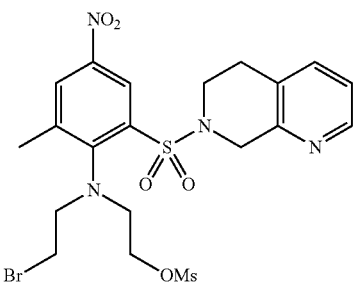 736 |
| 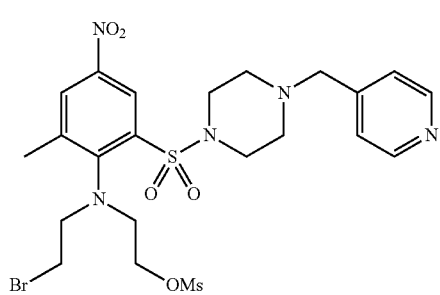 732 | 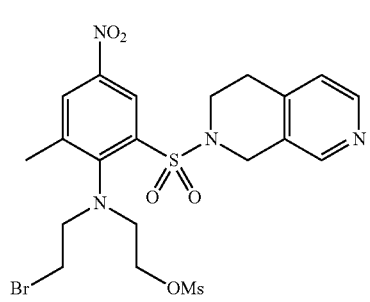 737 |
| 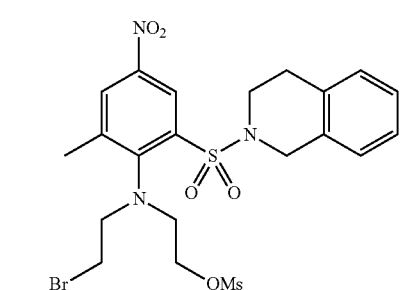 733 | 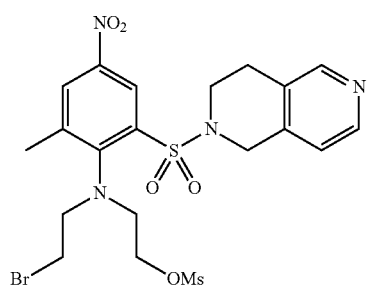 738 |
| 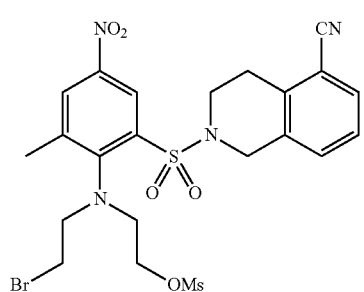 734 | 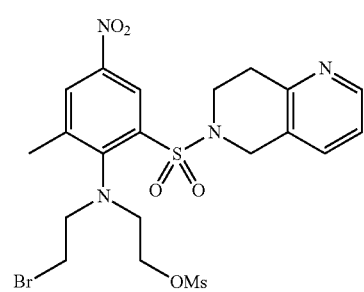 739 |
| 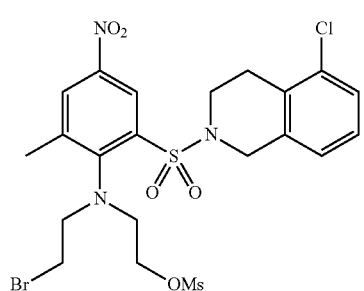 735 | 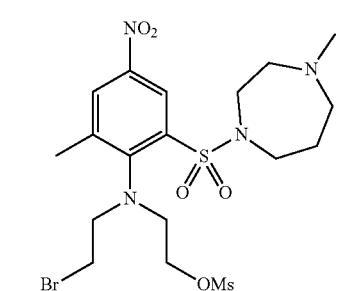 740 |

| | |
|---|---|
| 741 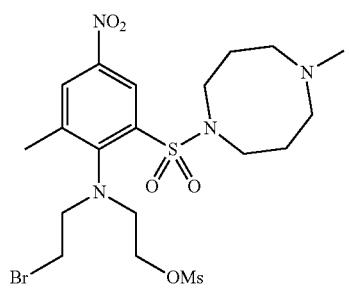 | 746 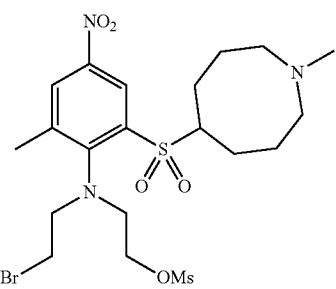 |
| 742 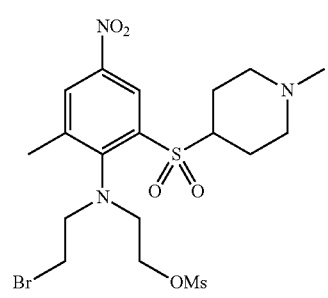 | 747 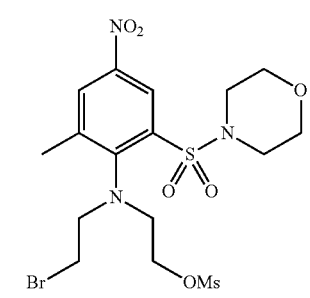 |
| 743 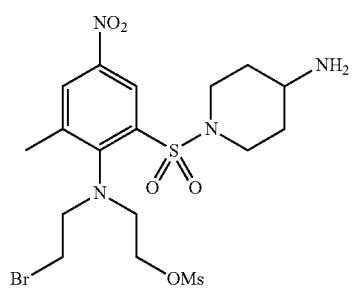 | 748 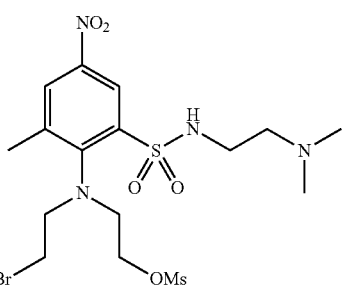 |
| 744 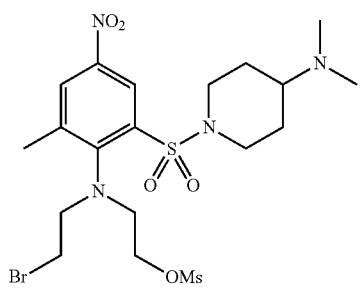 | 749 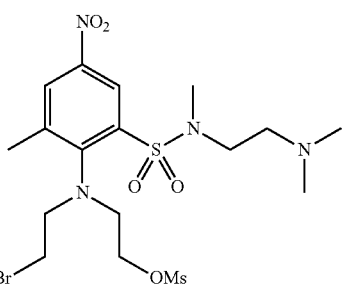 |
| 745 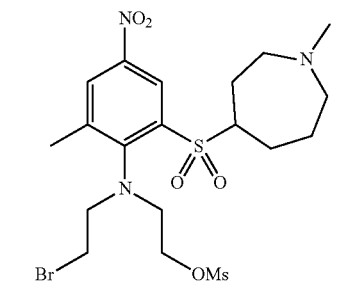 | 750 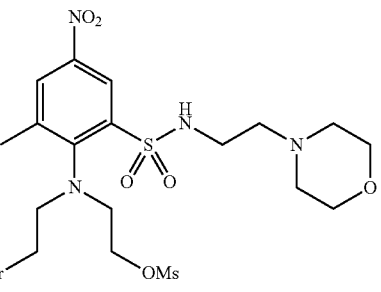 |

751 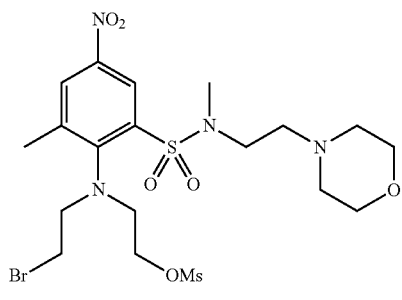
752 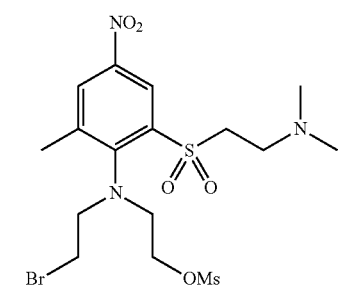
757 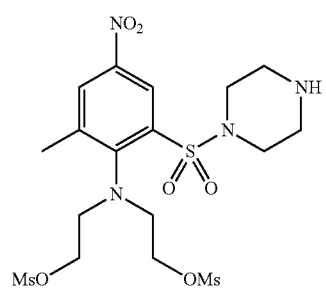
758 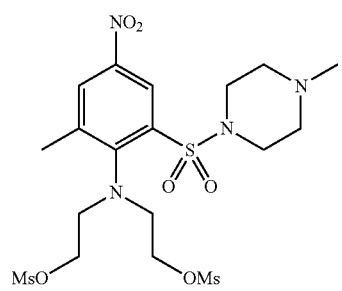
759 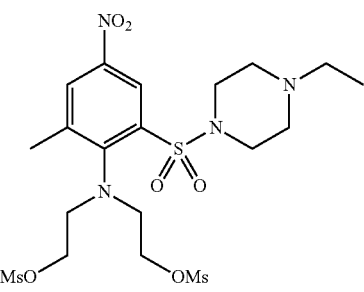
760 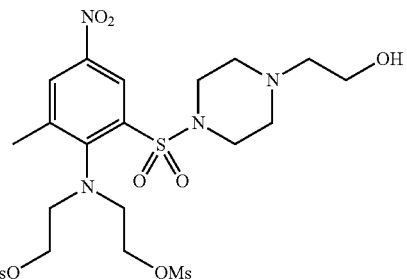
761 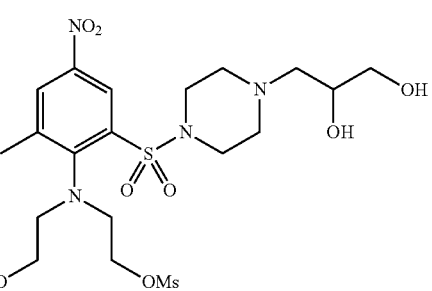
762 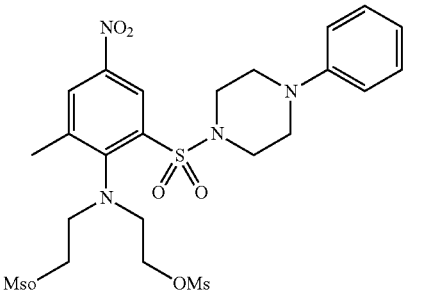
763 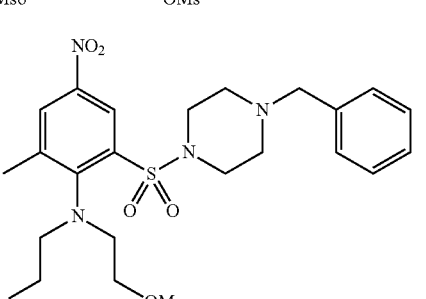
764 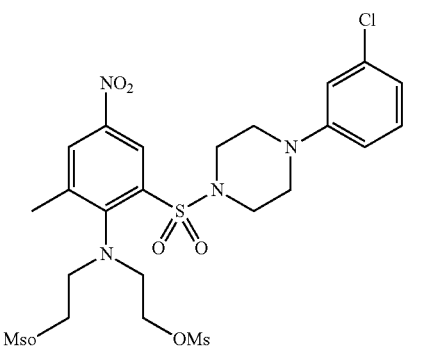

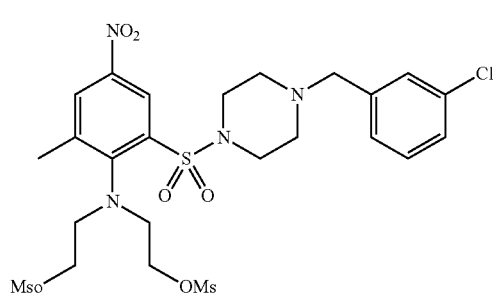
765
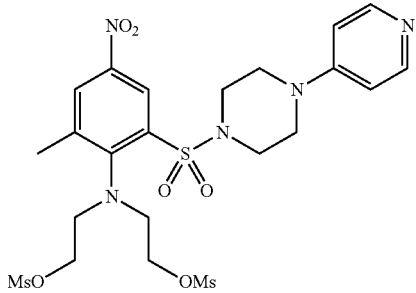
770
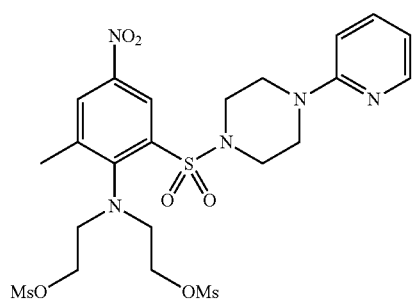
766
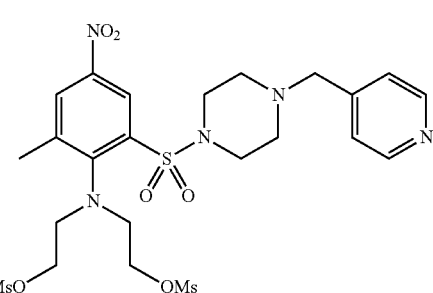
771
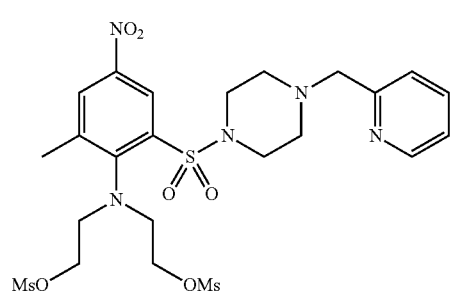
767
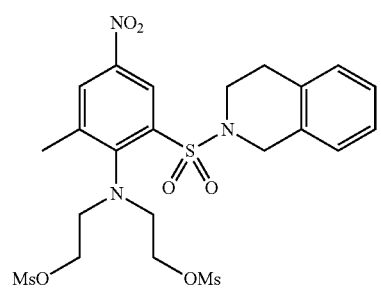
772
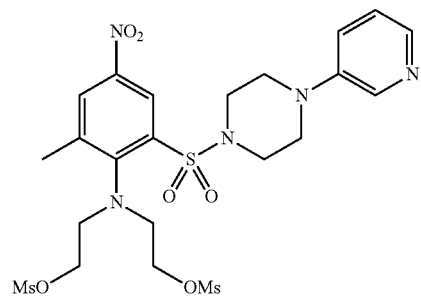
768
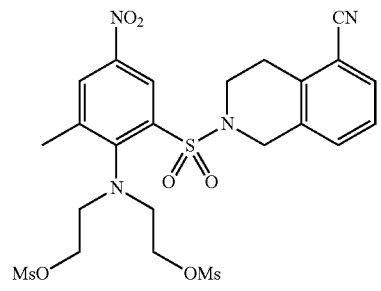
773
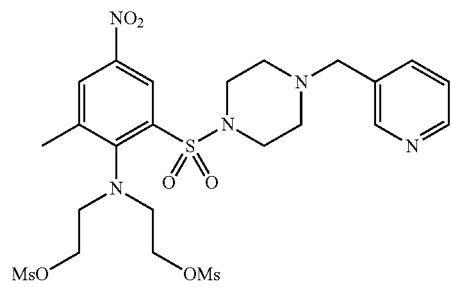
769
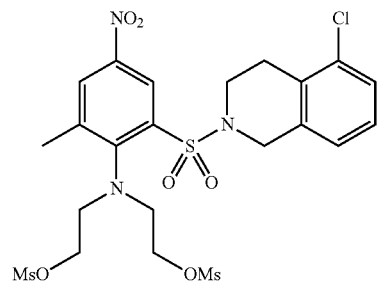
774

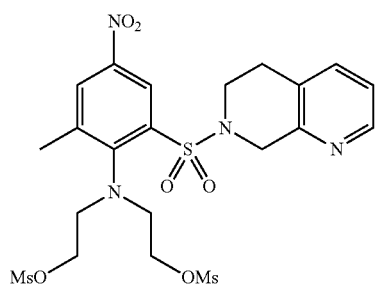 775
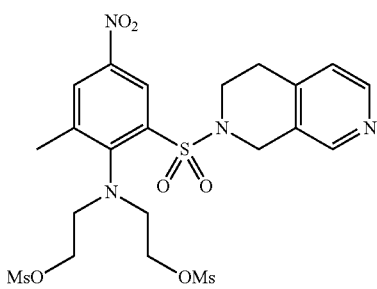 776
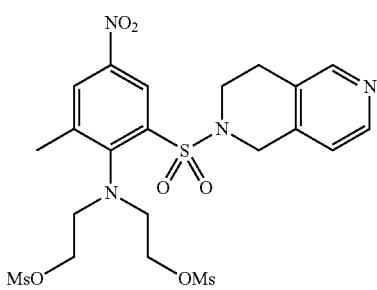 777
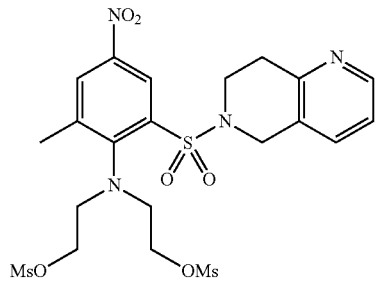 778
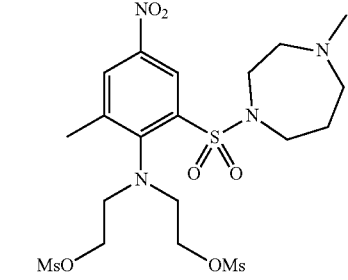 779
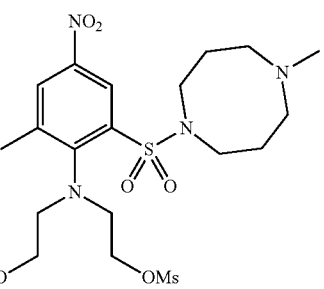 780
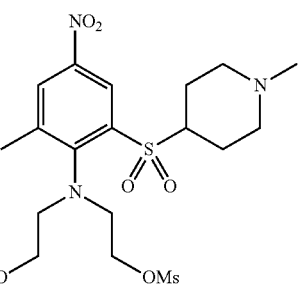 781
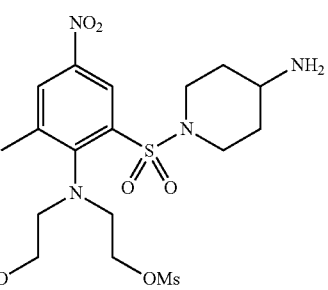 782
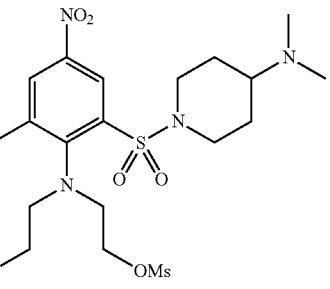 783
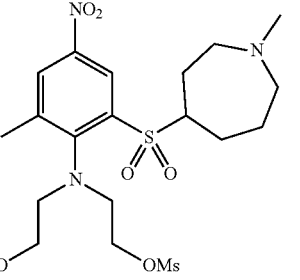 784

785 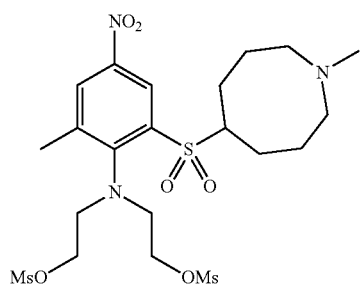
786 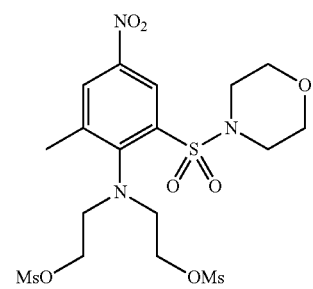
787 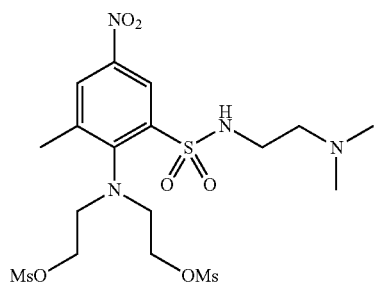
788 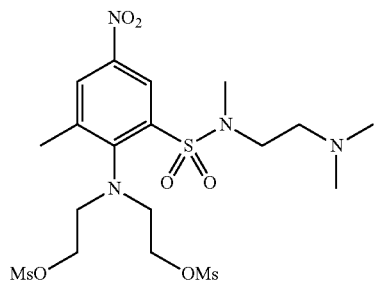
789 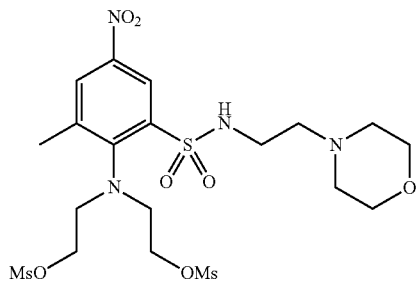
790 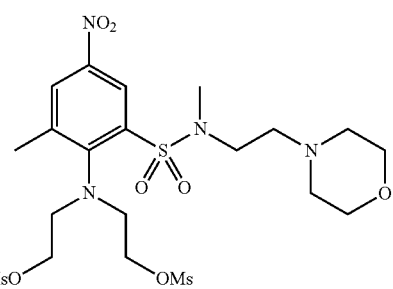
791 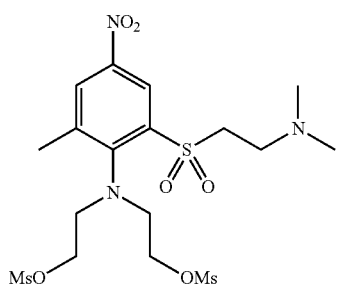
3-Trifluoromethyl-5-nitrobenzenesulfonamide dibromo, bromomesylate and bismesylate mustards (913-1025):
913 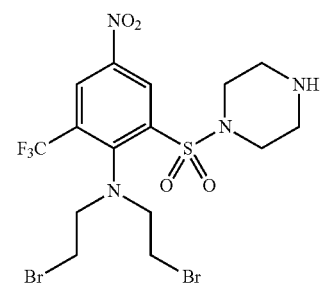
914 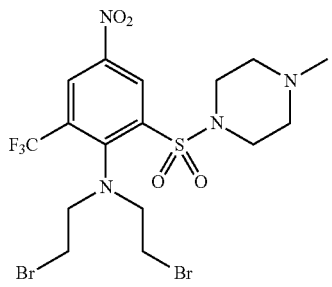
915 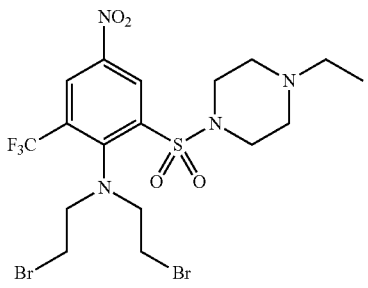

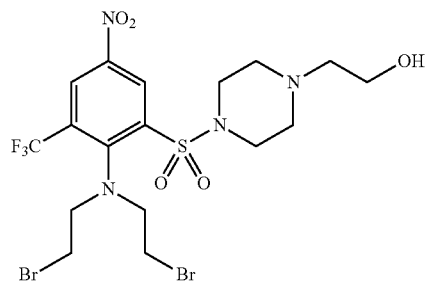
916
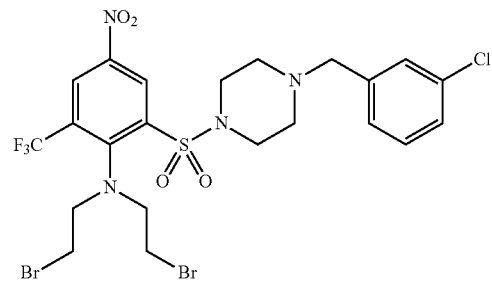
921
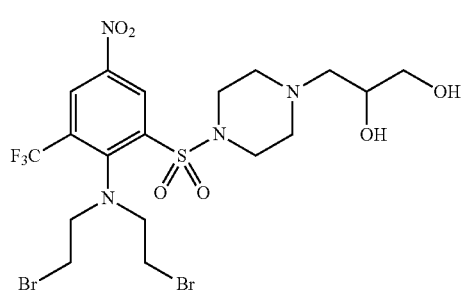
917
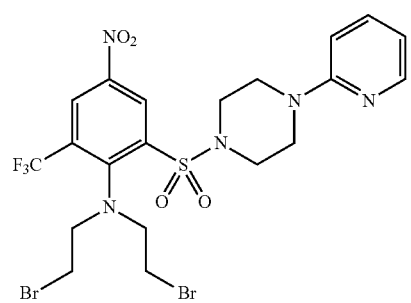
922
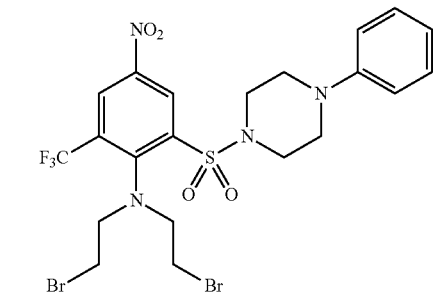
918
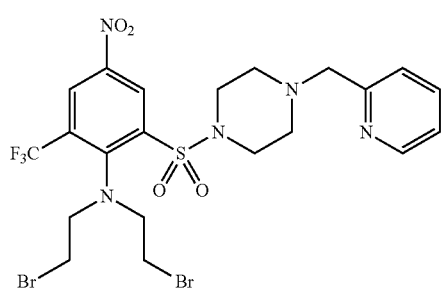
923
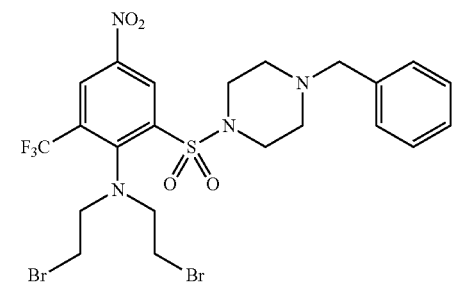
919
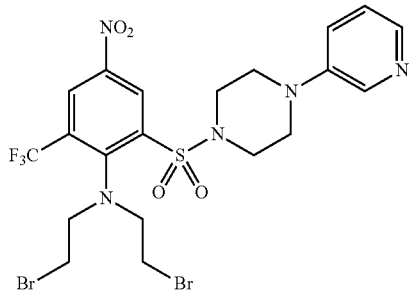
924
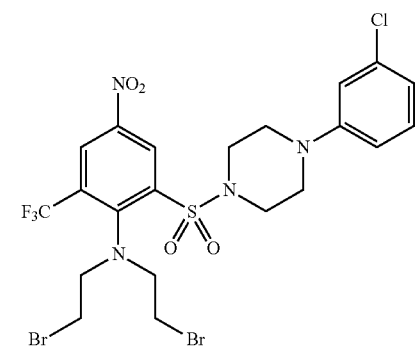
920
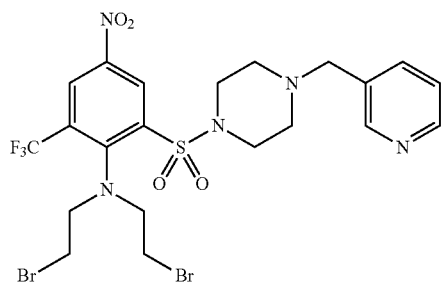
925

-continued
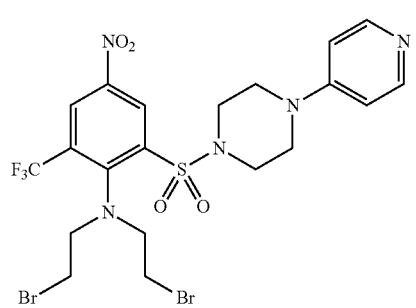 926
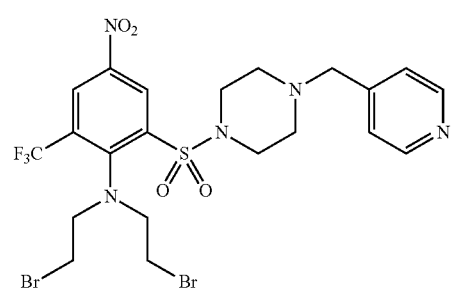 927
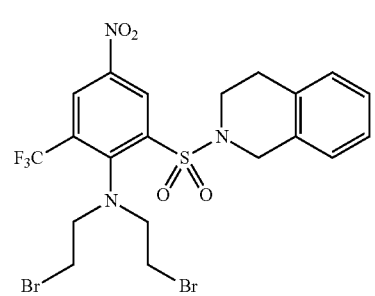 928
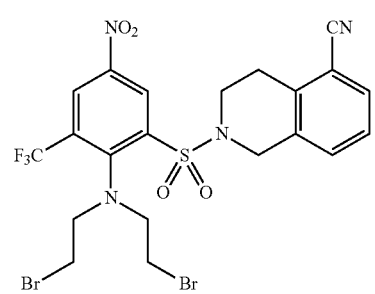 929
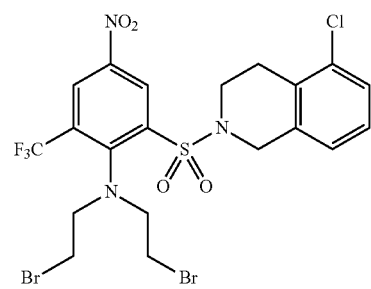 930
-continued
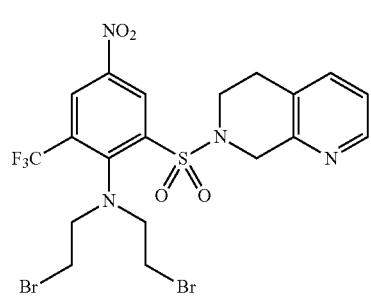 931
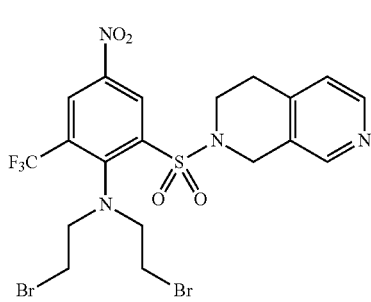 932
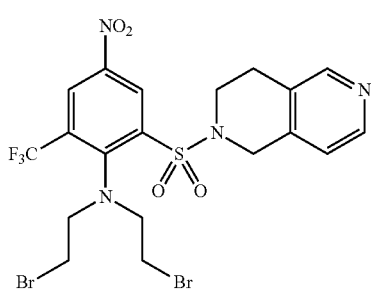 933
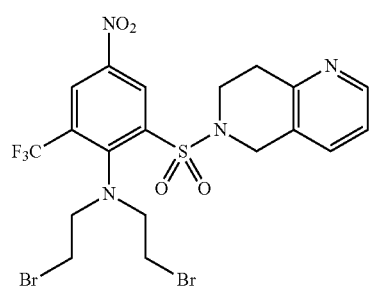 934
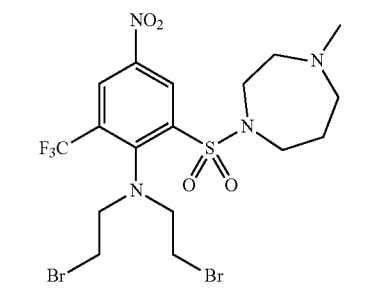 935

| | |
|---|---|
| 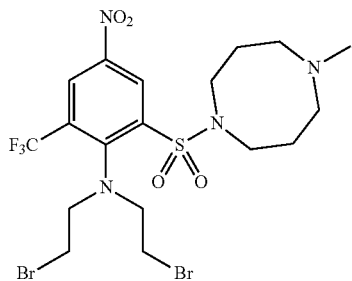 936 | 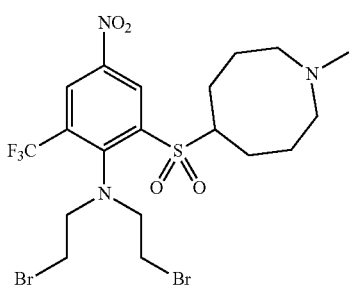 941 |
| 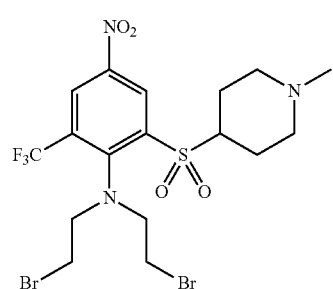 937 | 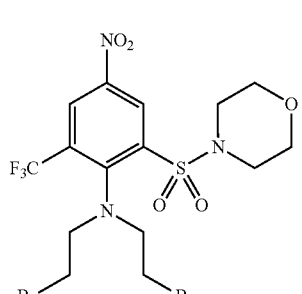 942 |
| 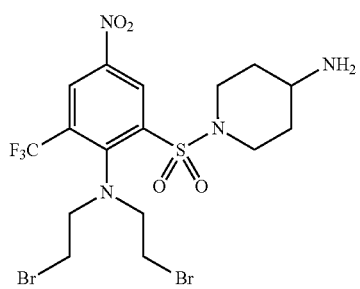 938 | 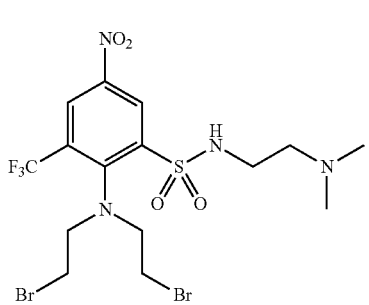 943 |
| 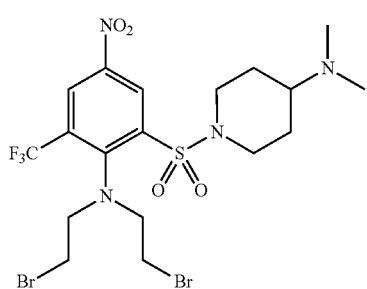 939 | 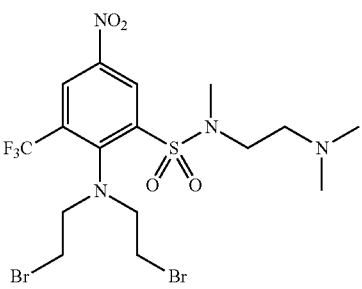 944 |
| 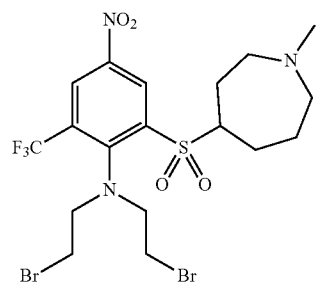 940 | 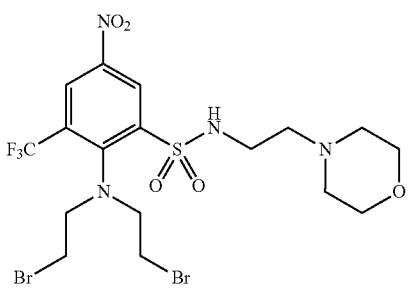 945 |

946 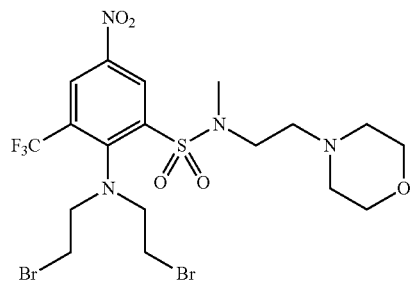
947 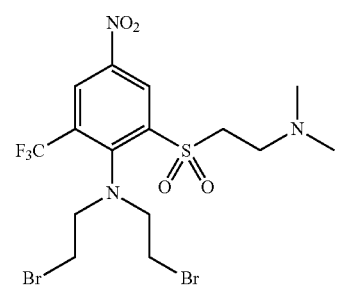
952 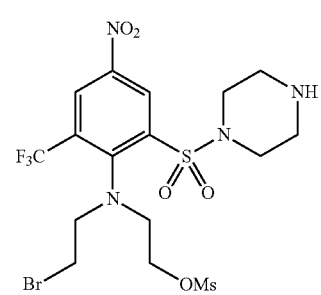
953 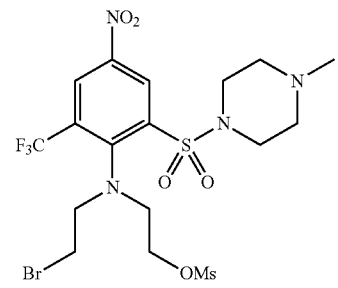
954 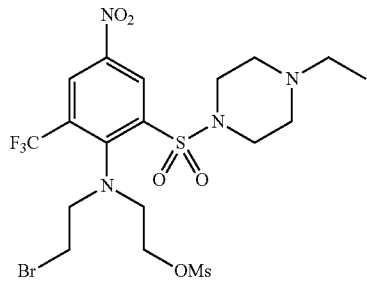
955 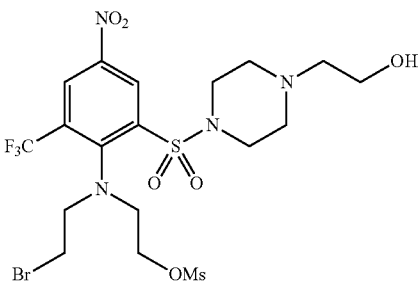
956 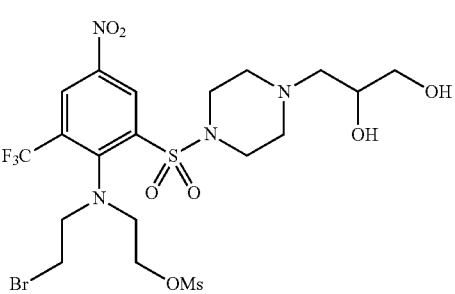
957 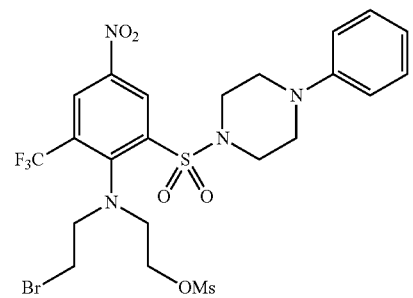
958 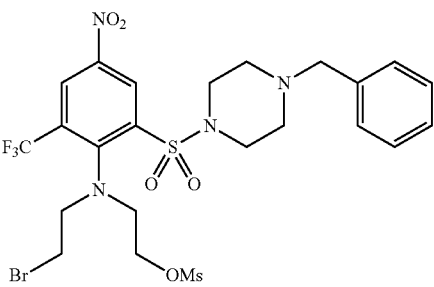
959 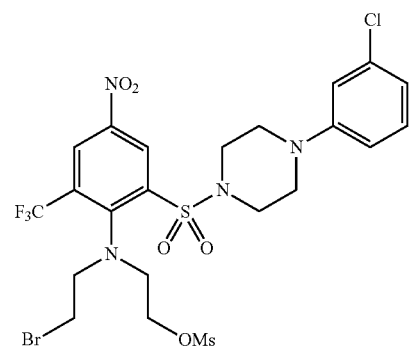

960 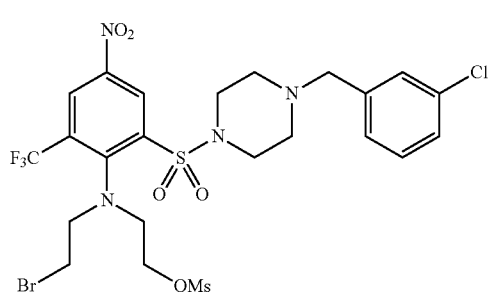
961 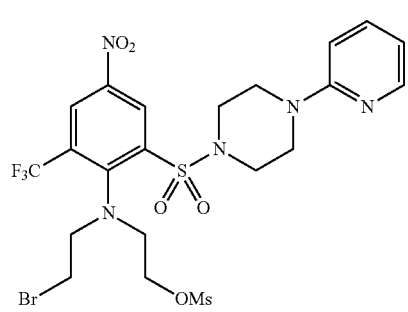
962 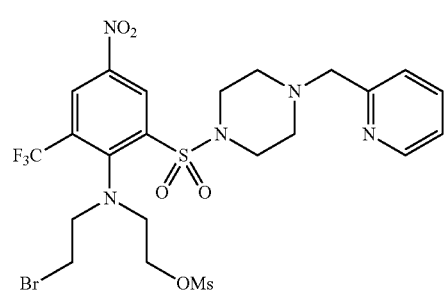
963 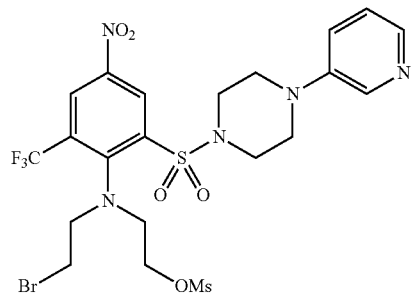
964 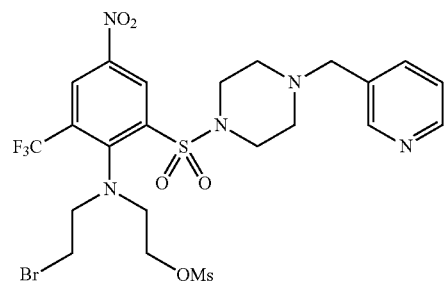
965 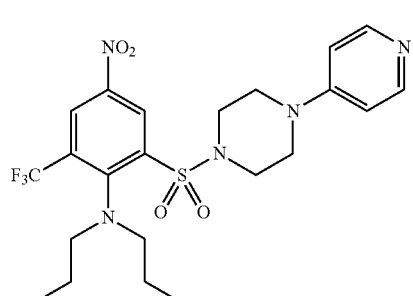
966 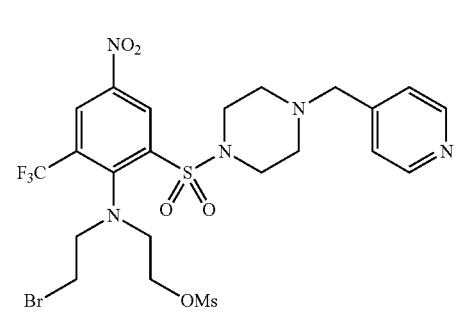
967 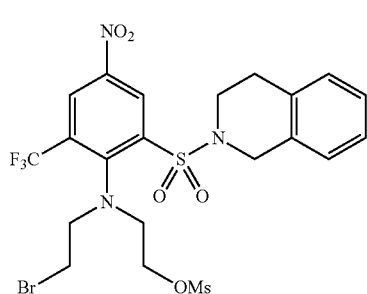
968 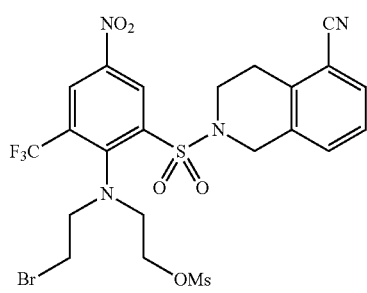
969 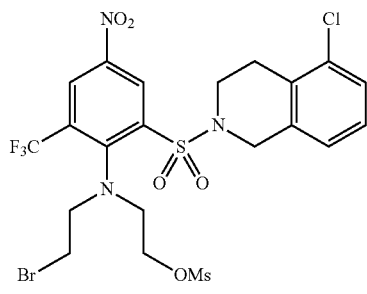

77
-continued
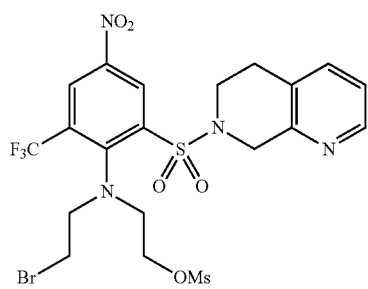
970
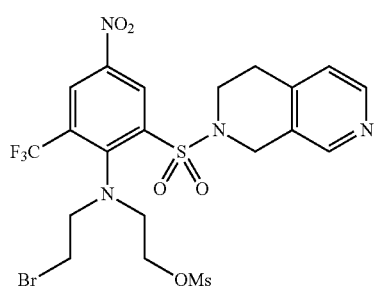
971
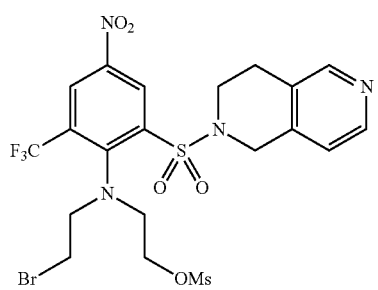
972
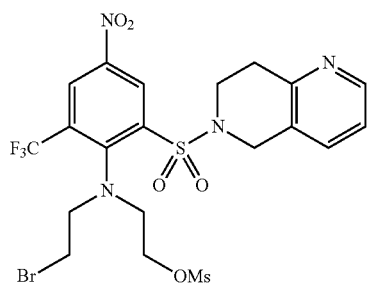
973
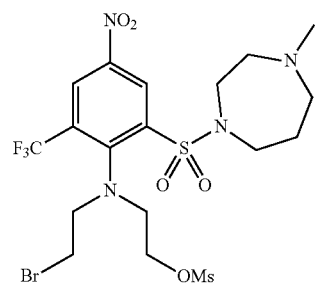
974
78
-continued
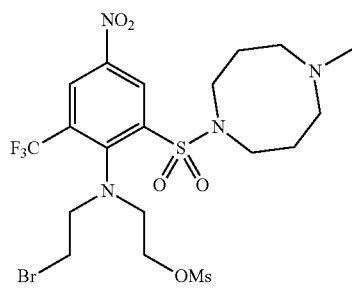
975
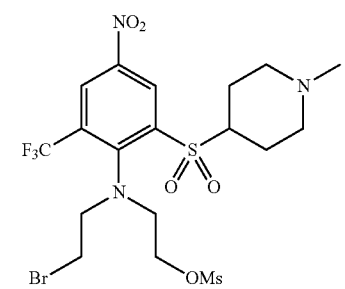
976
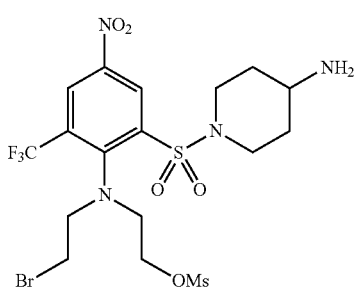
977
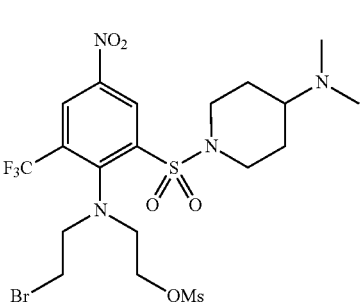
978
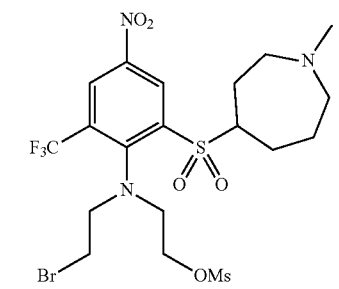
979

| | |
|---|---|
| 980 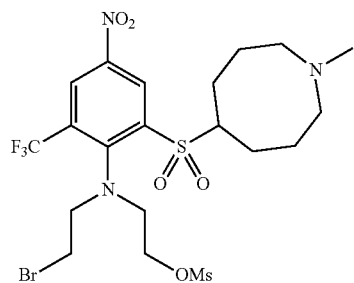 | 985 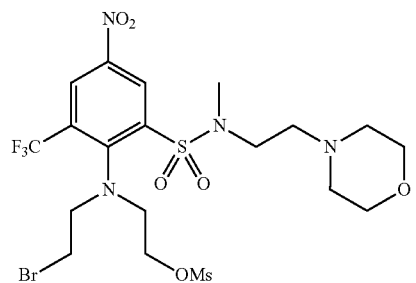 |
| 981 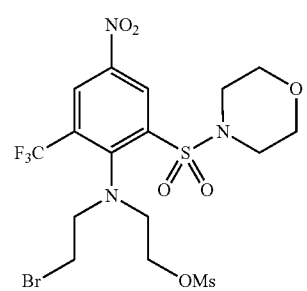 | 986 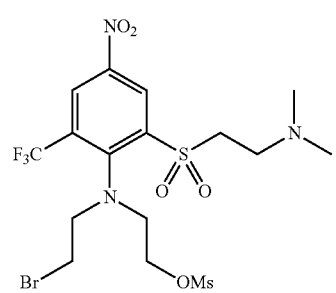 |
| 982 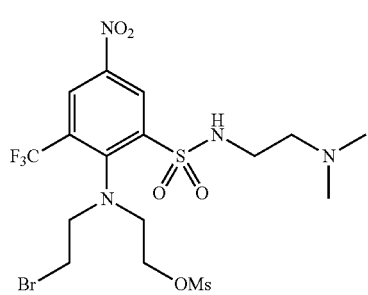 | 991 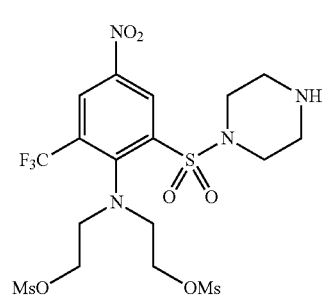 |
| 983 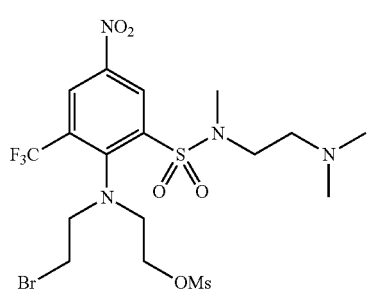 | 992 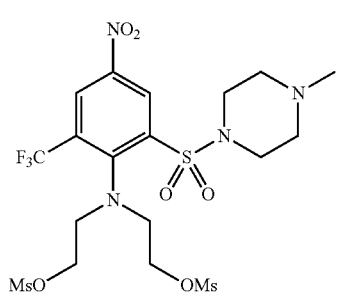 |
| 984 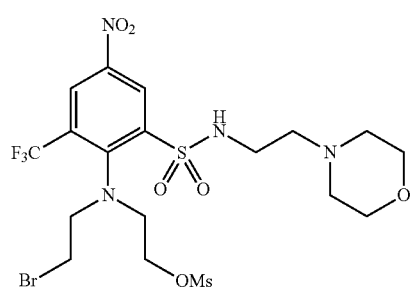 | 993 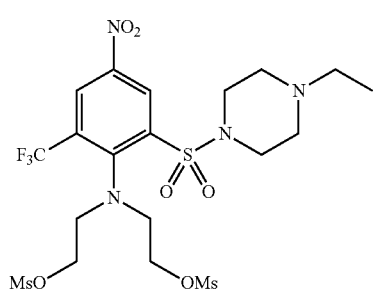 |

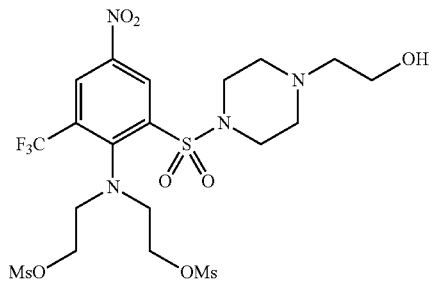
994
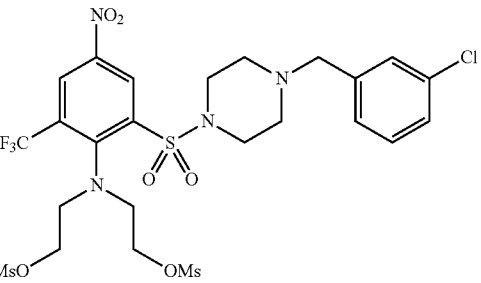
999
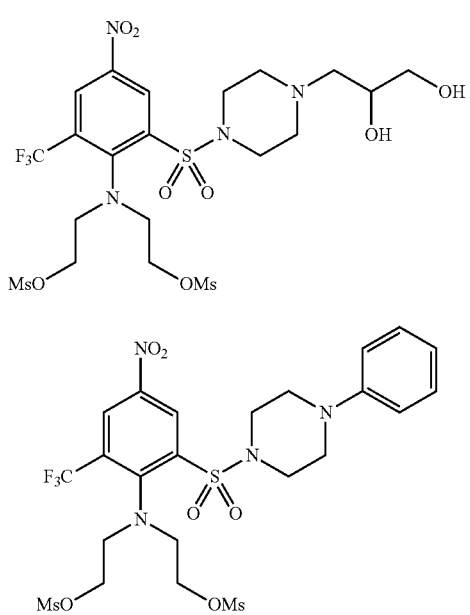
995
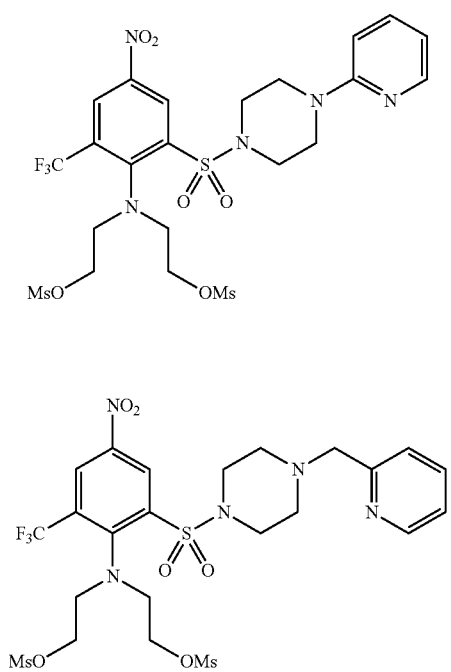
1000
996
1001
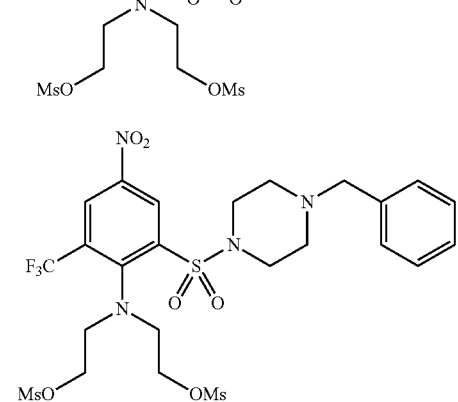
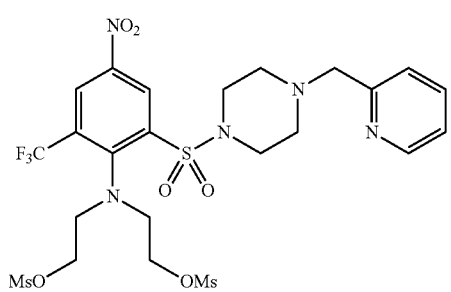
997
1002
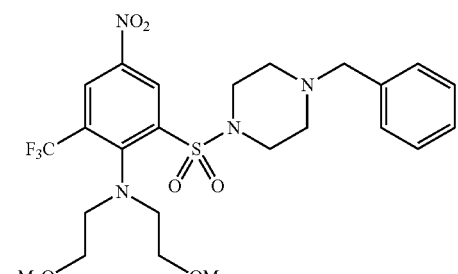
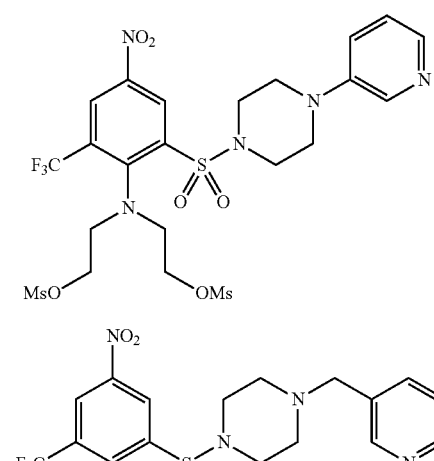
998
1003
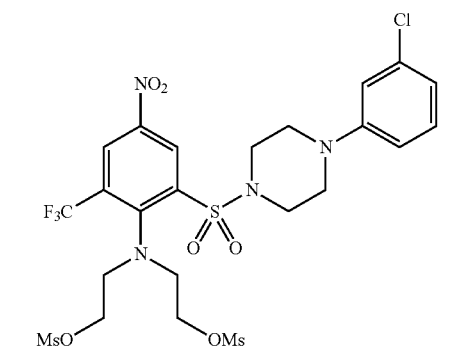
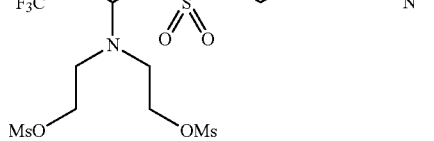

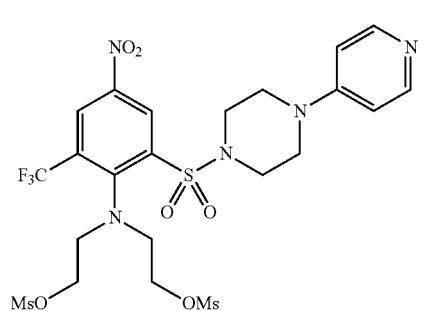 1004
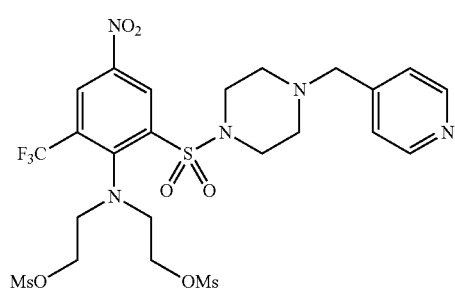 1005
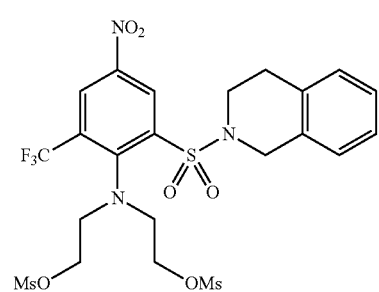 1006
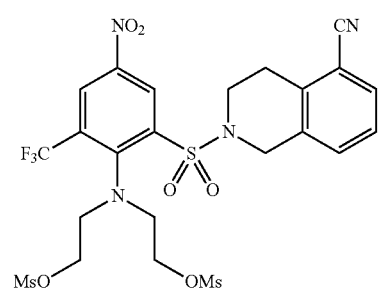 1007
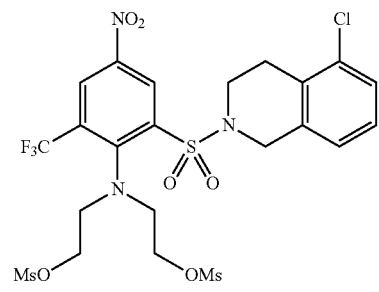 1008
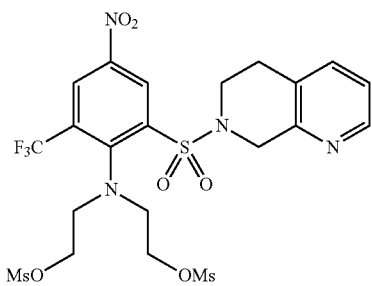 1009
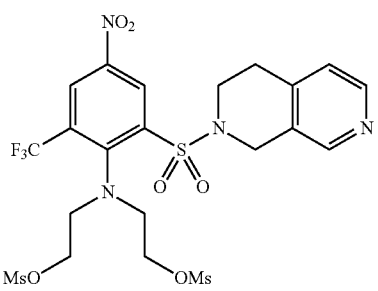 1010
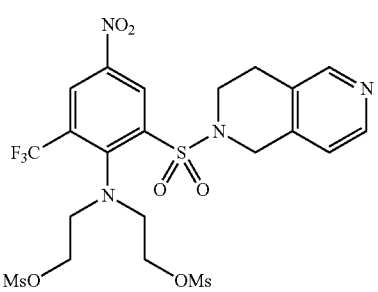 1011
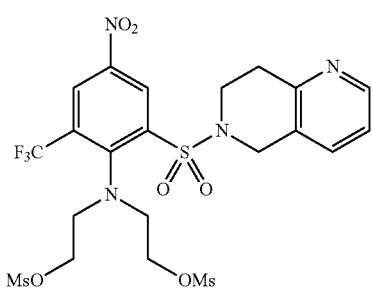 1012
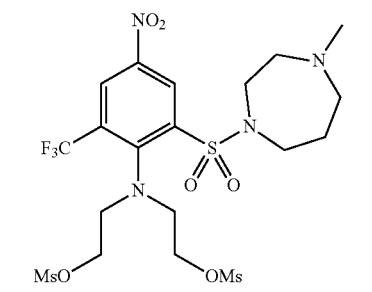 1013

-continued
1014 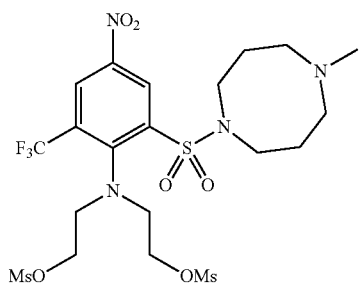
1015 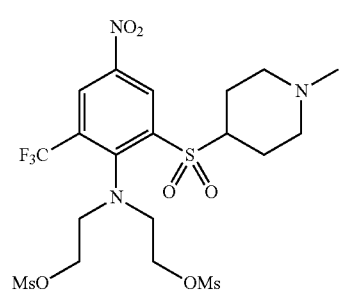
1016 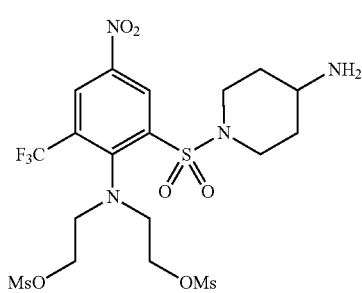
1017 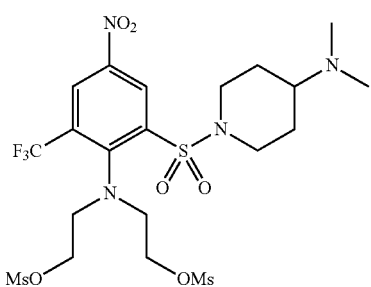
1018 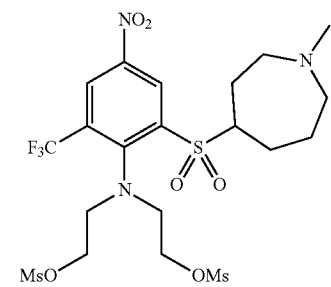
-continued
1019 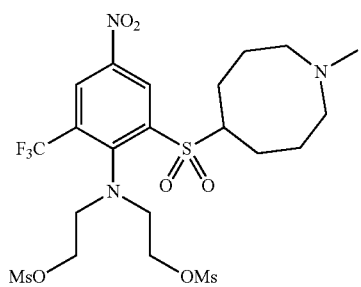
1020 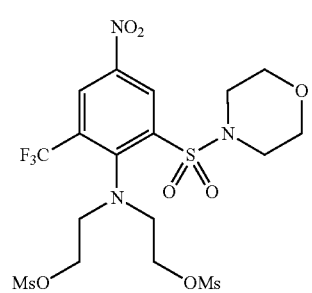
1021 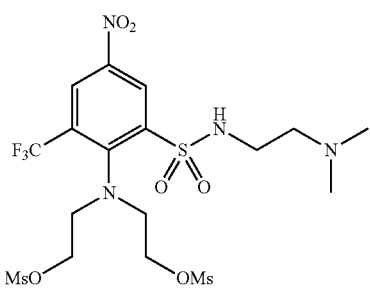
1022 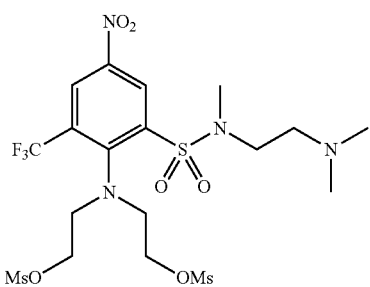
1023 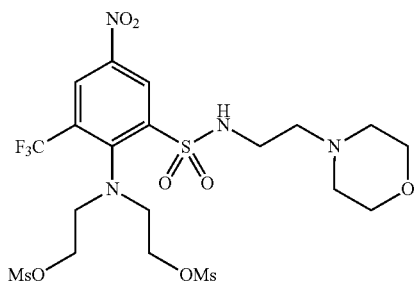

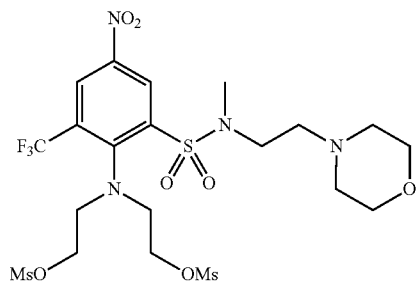
1024
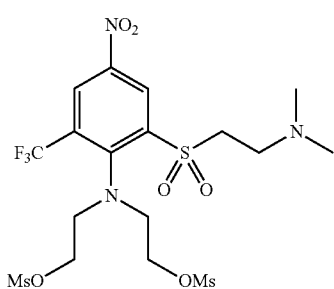
1025
3-Ethynyl-5-nitrobenzenesulfonamide dibromo, bromomesylate and bismesylate mustards (1030-1142):
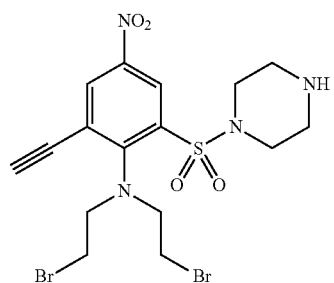
1030
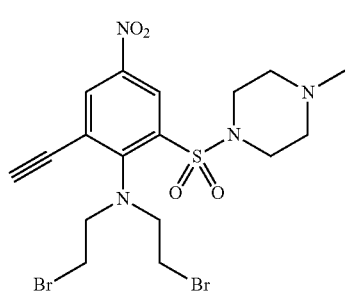
1031
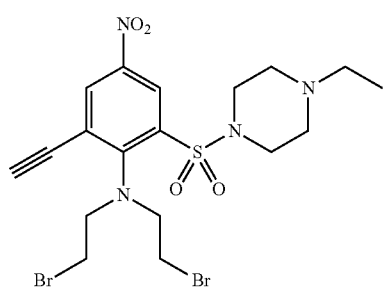
1032
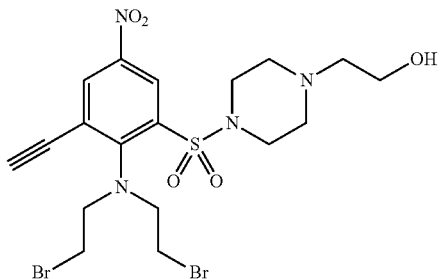
1033
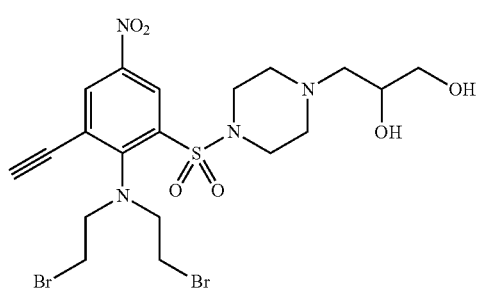
1034
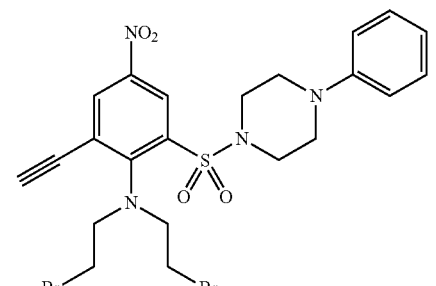
1035
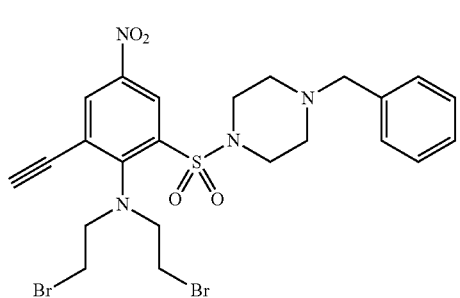
1036
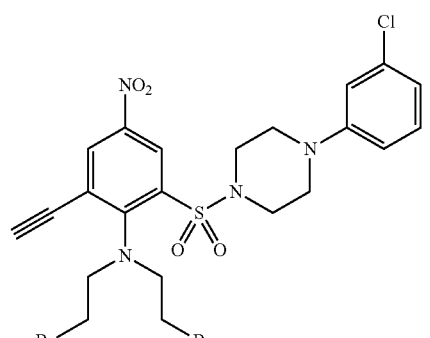
1037

1038 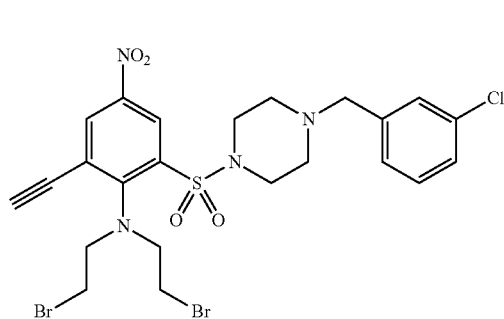
1039 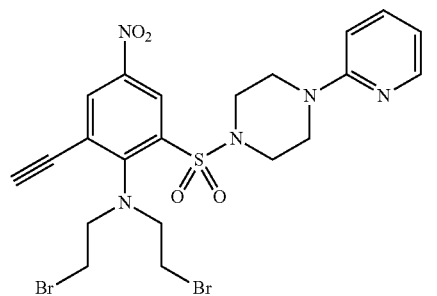
1040 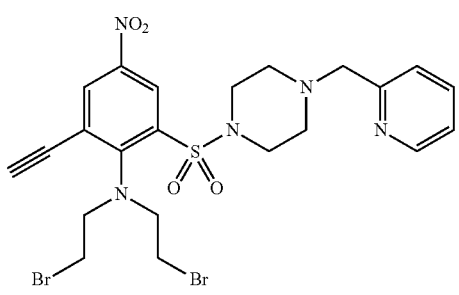
1041 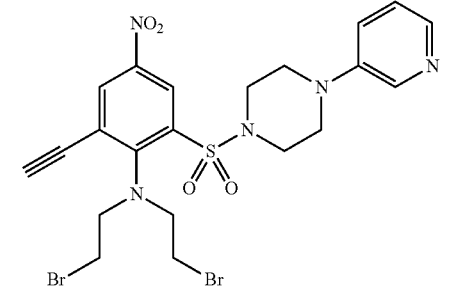
1042 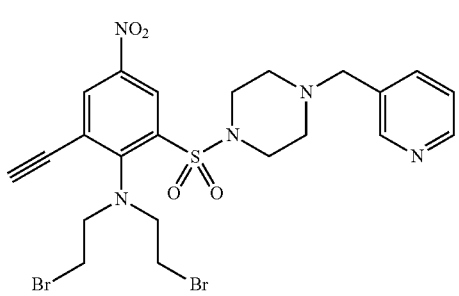
1043 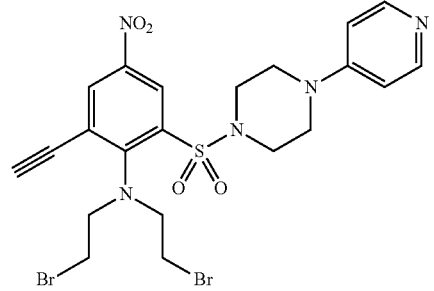
1044 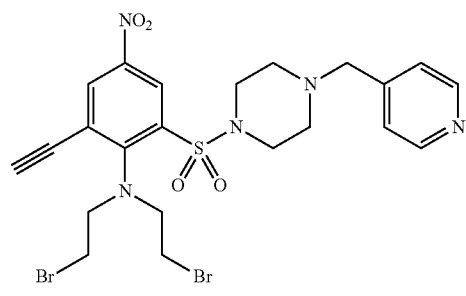
1045 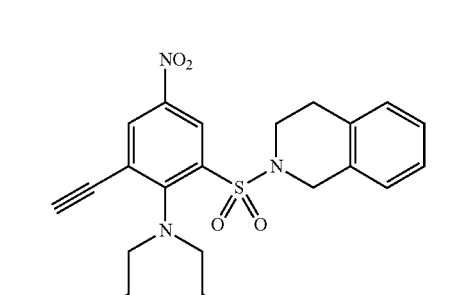
1046 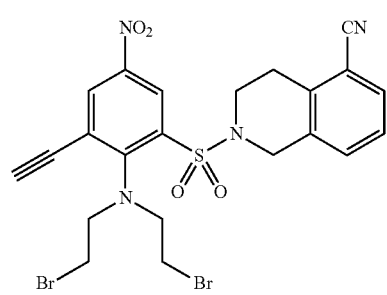
1047 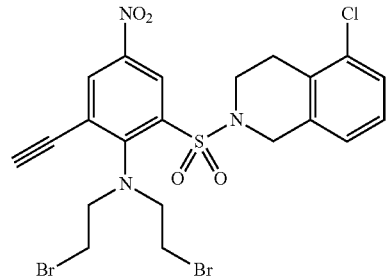

-continued

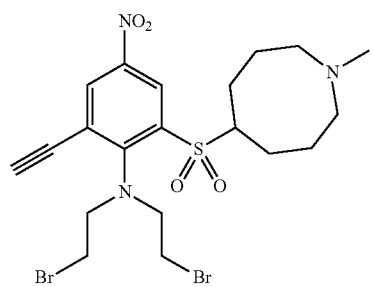
1058
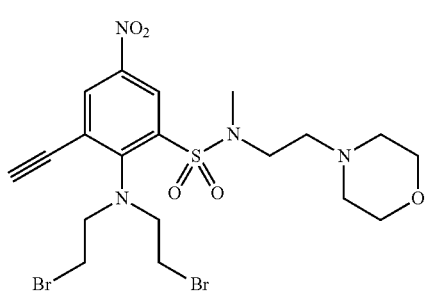
1063
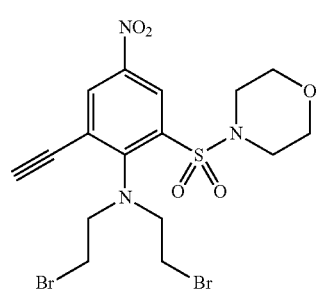
1059
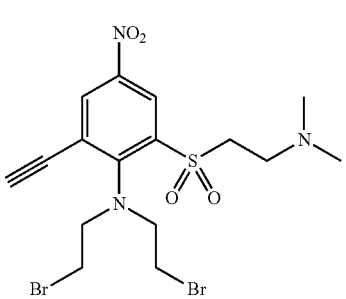
1064
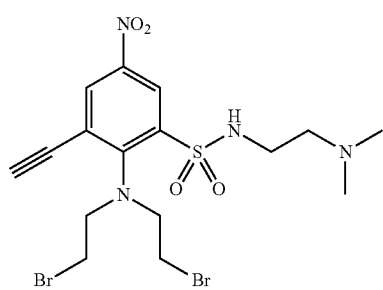
1060
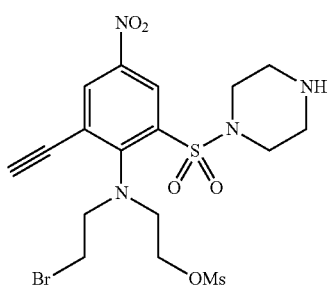
1069
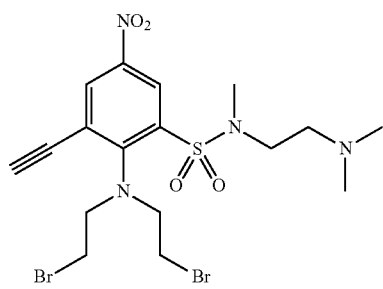
1061
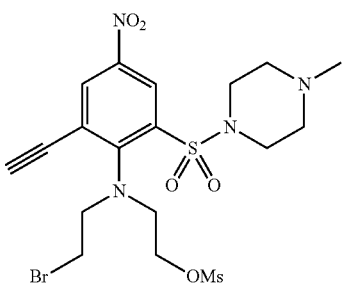
1070
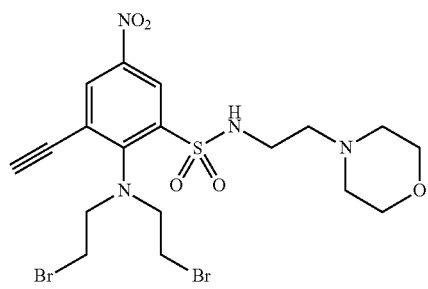
1062
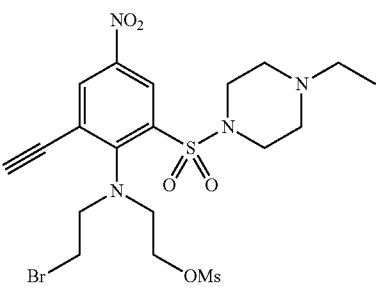
1071

95
-continued
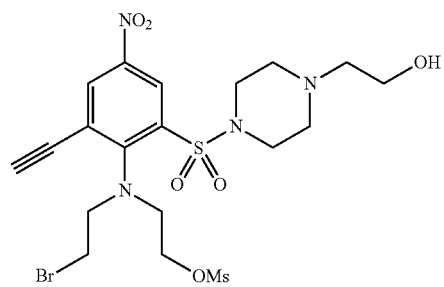
1072
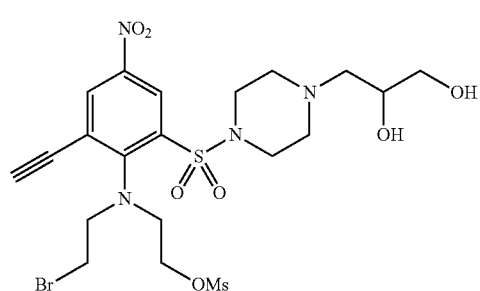
1073
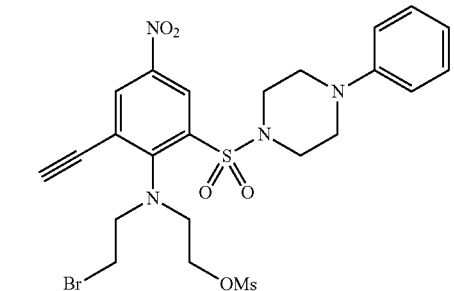
1074
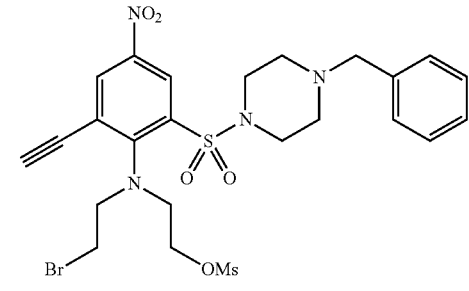
1075
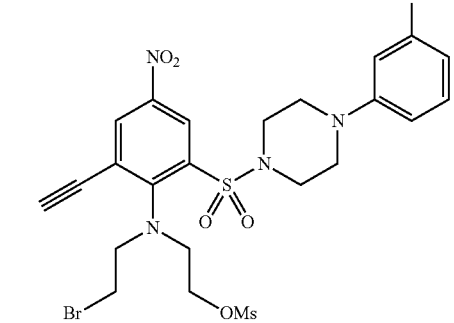
1076
96
-continued
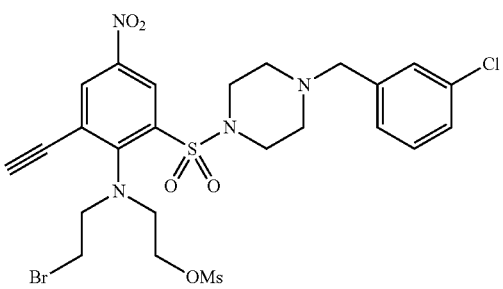
1077
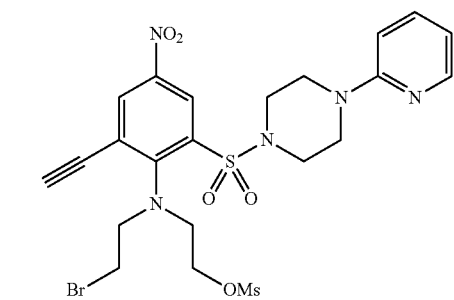
1078
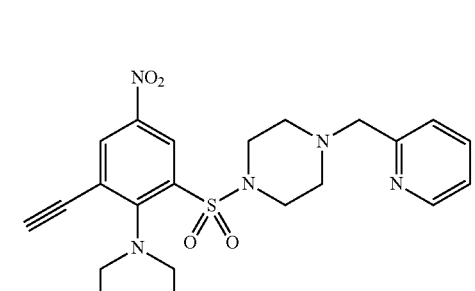
1079
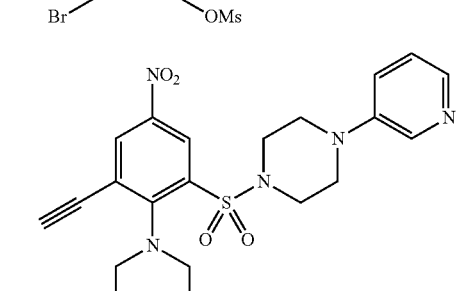
1080
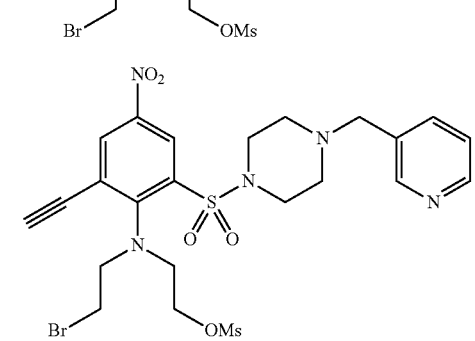
1081

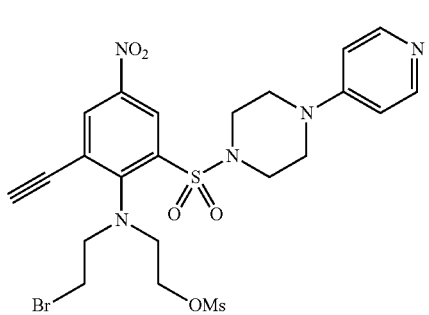
1082
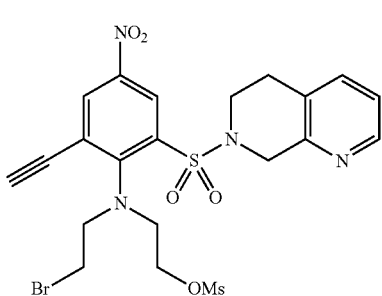
1087
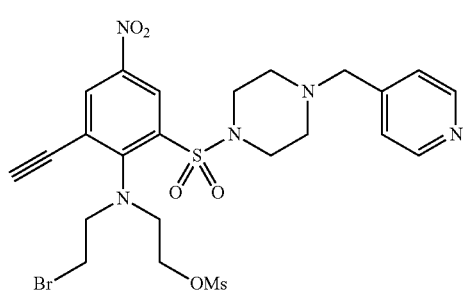
1083
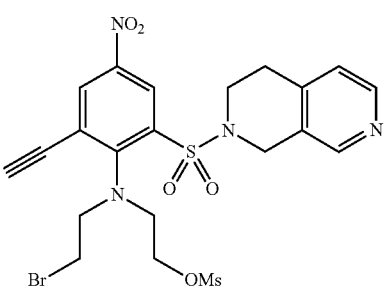
1088
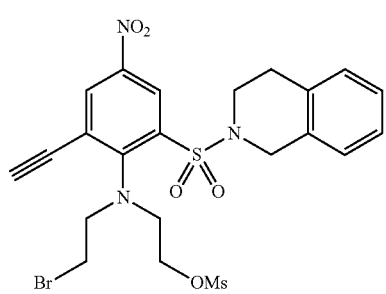
1084
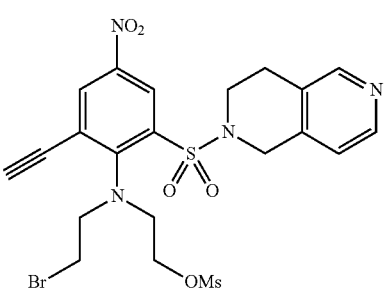
1089
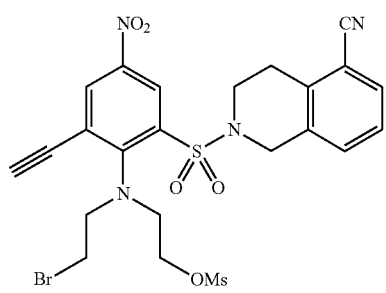
1085
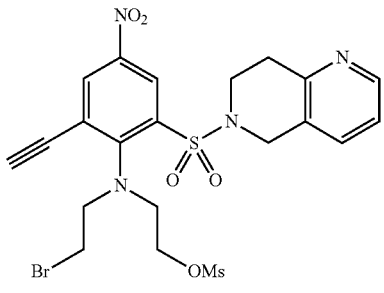
1090
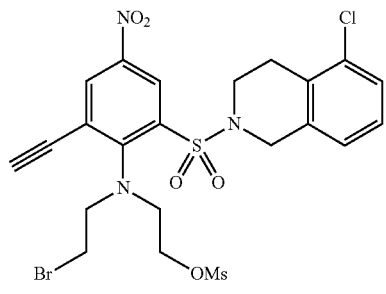
1086
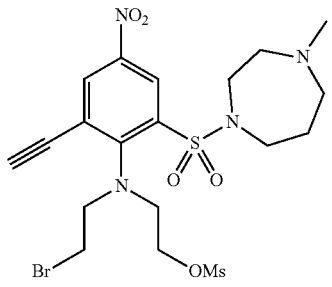
1091

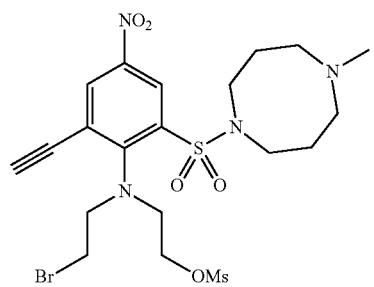
1092
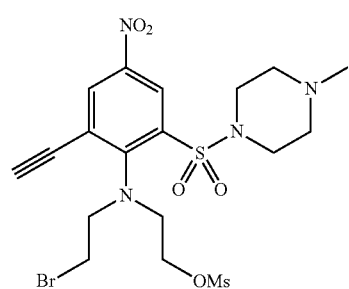
1093
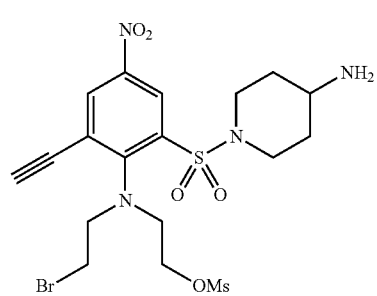
1094
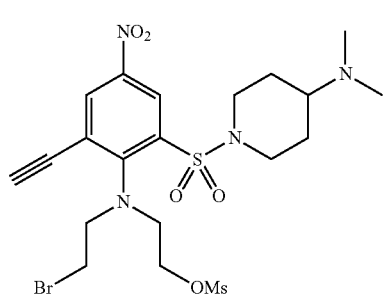
1095
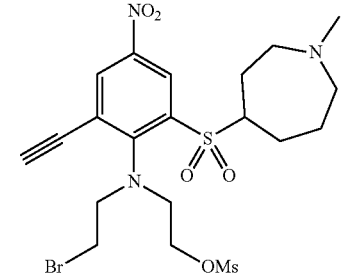
1096
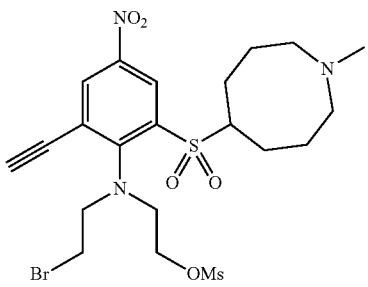
1097
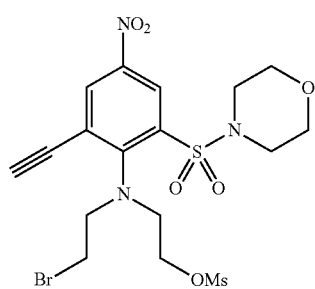
1098
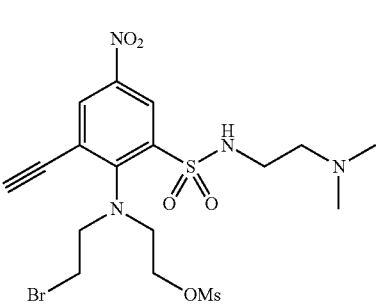
1099
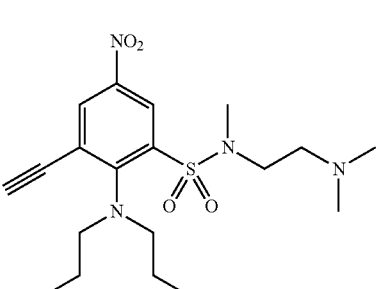
1100
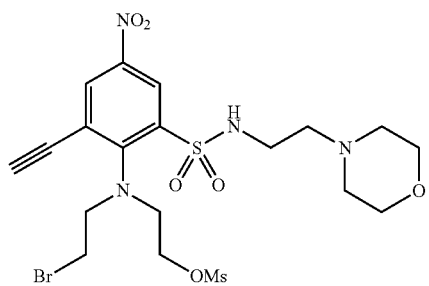
1101

101
-continued
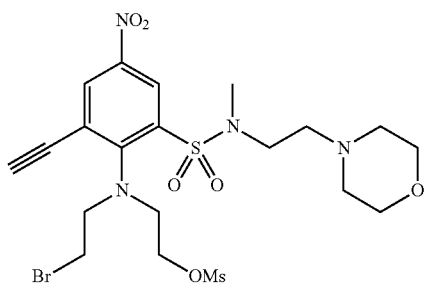
1102
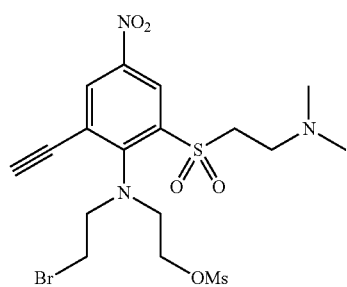
1103
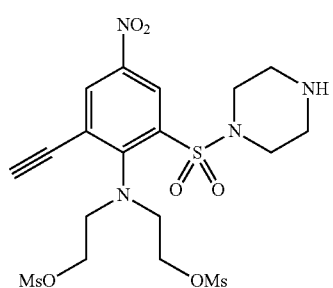
1108
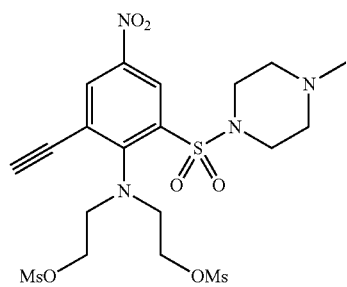
1109
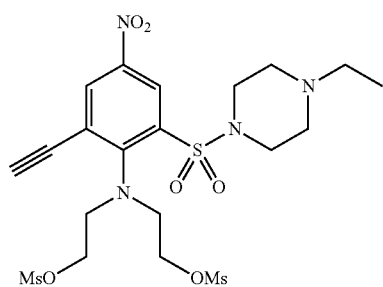
1110
102
-continued
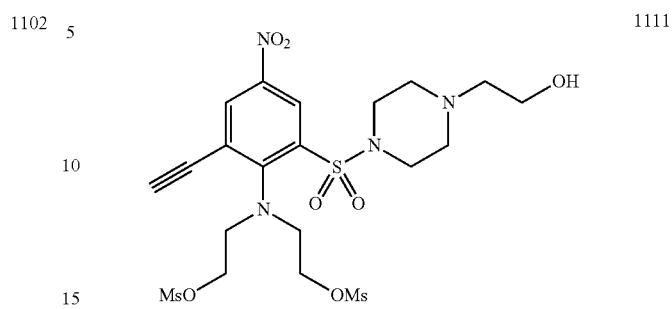
1111
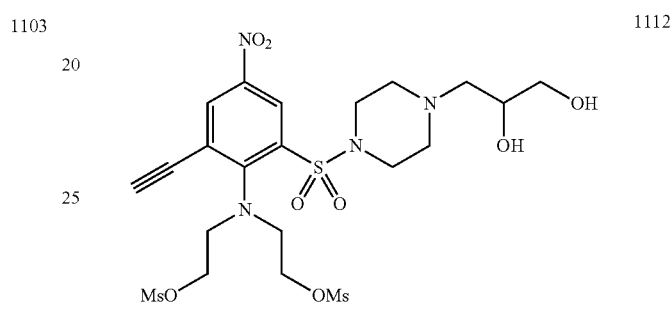
1112
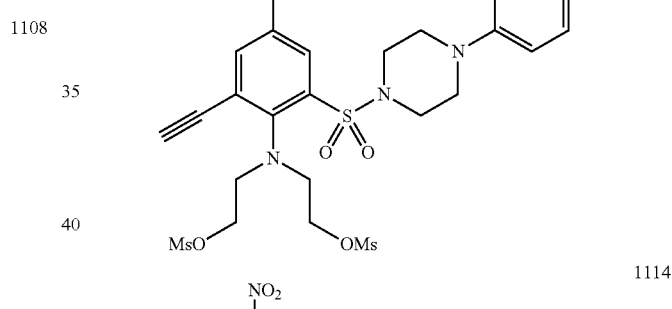
1113
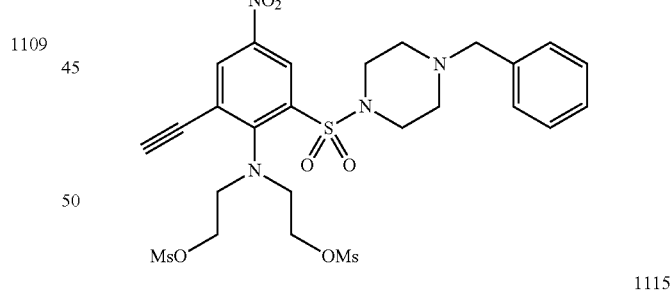
1114
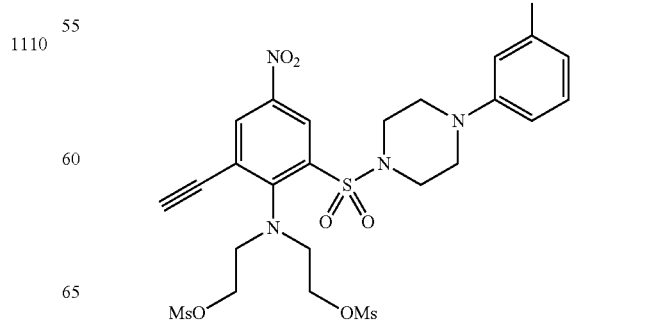
1115

103
-continued
1116
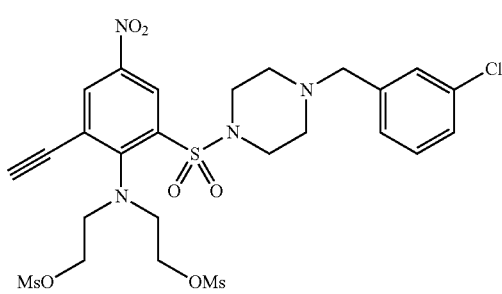
1117
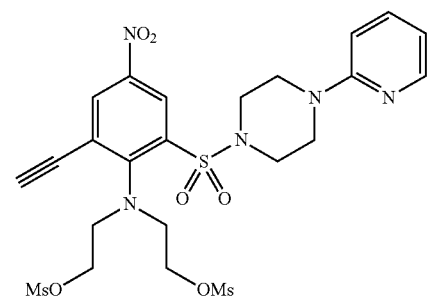
1118
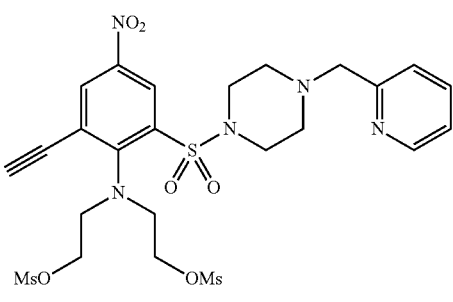
1119
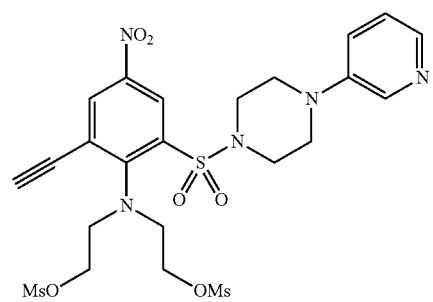
1120
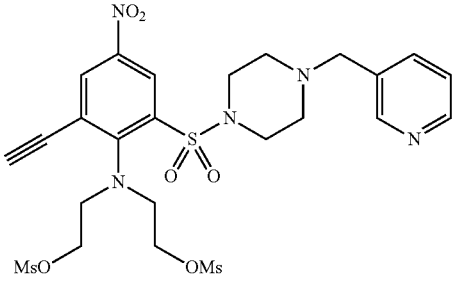
104
-continued
1121
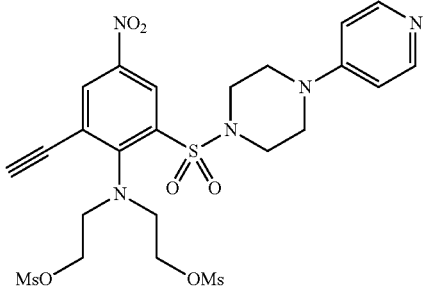
1122
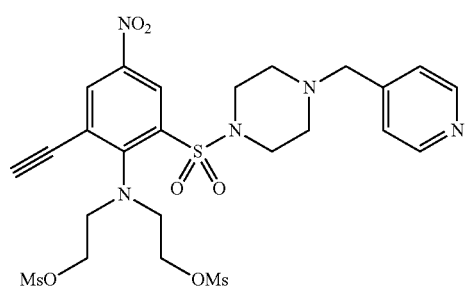
1123
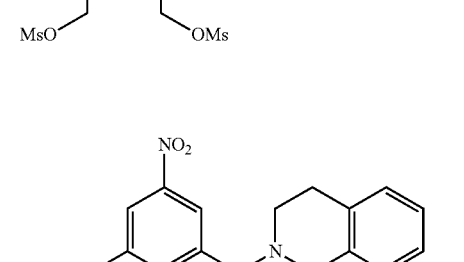
1124
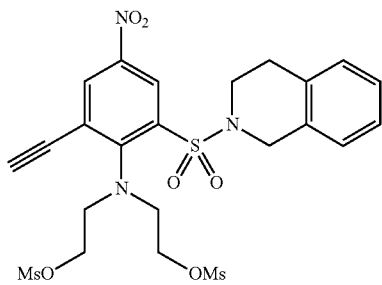
1125
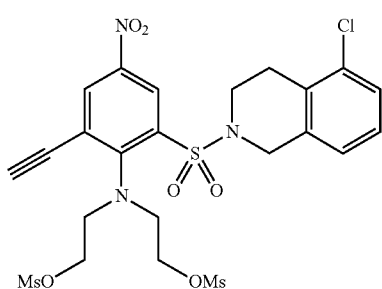

| 1126 | 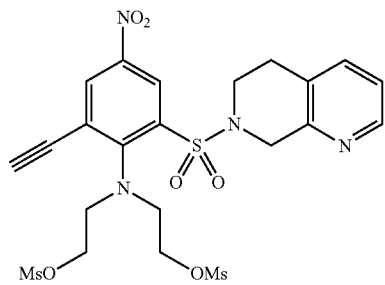 | 1131 | 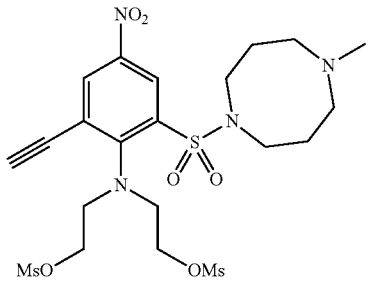 |
| 1127 | 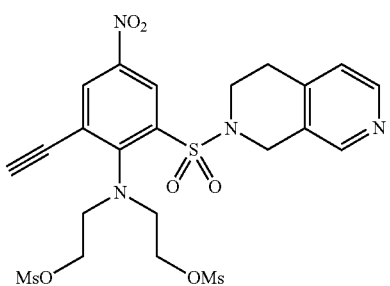 | 1132 | 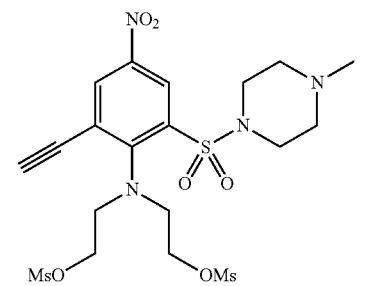 |
| 1128 | 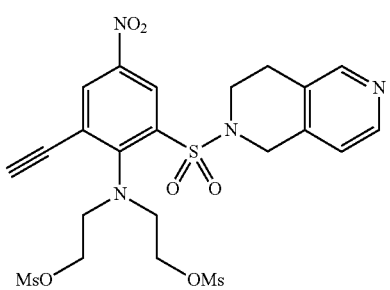 | 1133 | 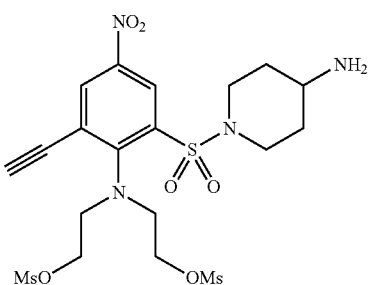 |
| 1129 | 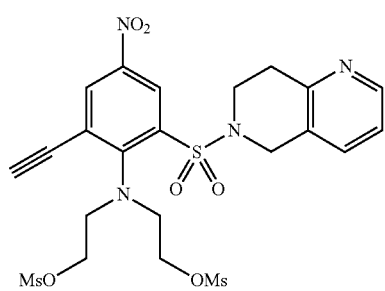 | 1134 | 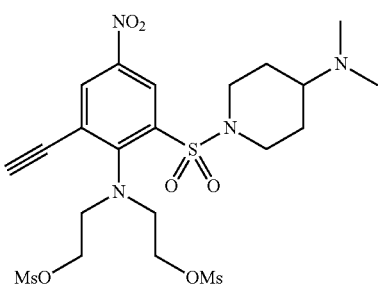 |
| 1130 | 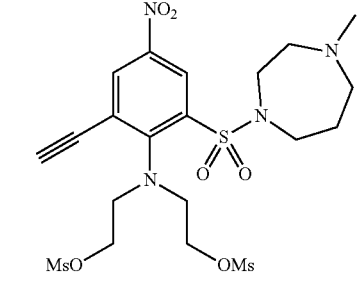 | 1135 | 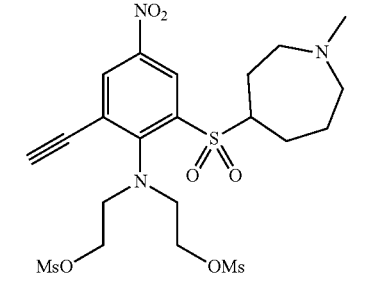 |

107
-continued
1136
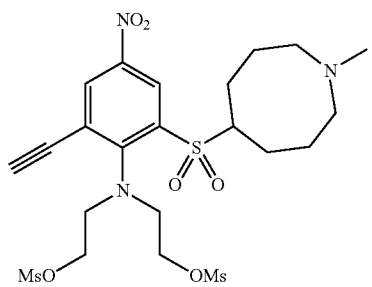
1137
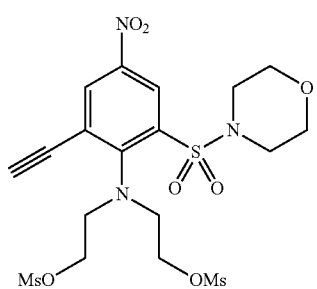
1138
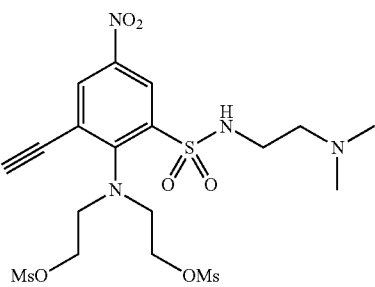
1139
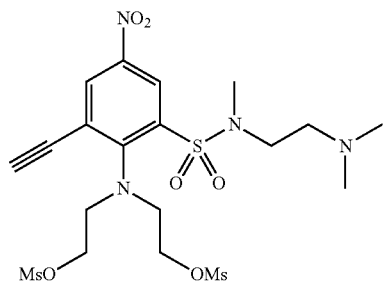
1140
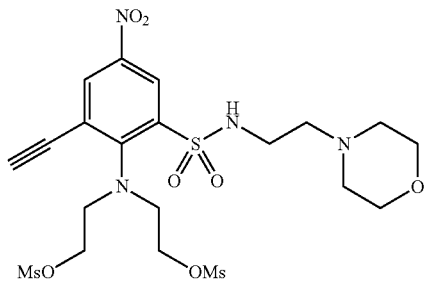
108
-continued
1141
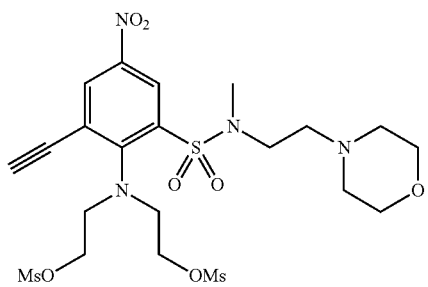
1142
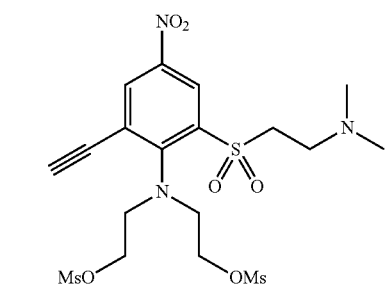
Methanesulfonate salts of 5-nitrobenzenesulfonamide bismesylate mustards (640.Ms-644.Ms, 757.Ms, 758.Ms, 991.Ms, 992.Ms, 1108.Ms and 1109.Ms):
640.Ms
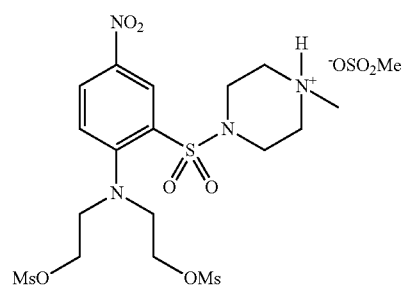
641.Ms
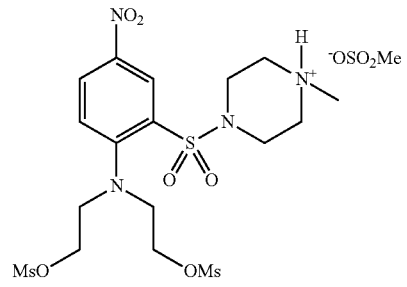
642.Ms
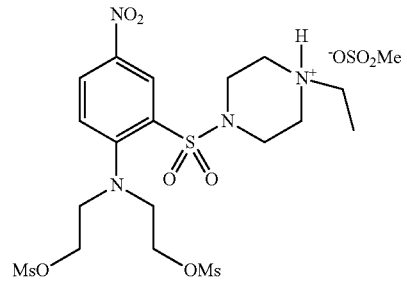

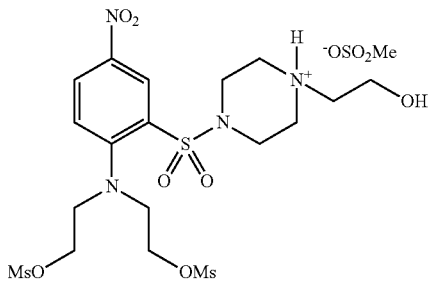

643.Ms

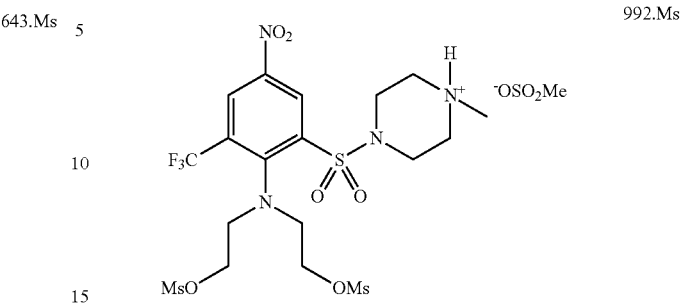

992.Ms

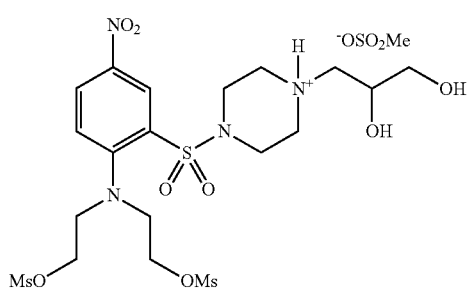

644.Ms

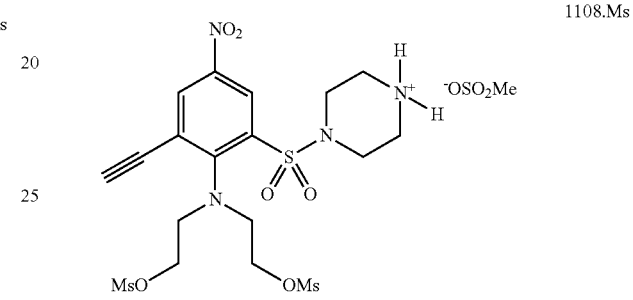

1108.Ms

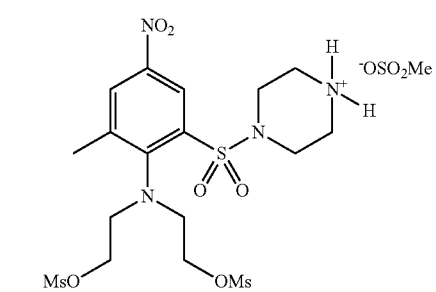

757.Ms

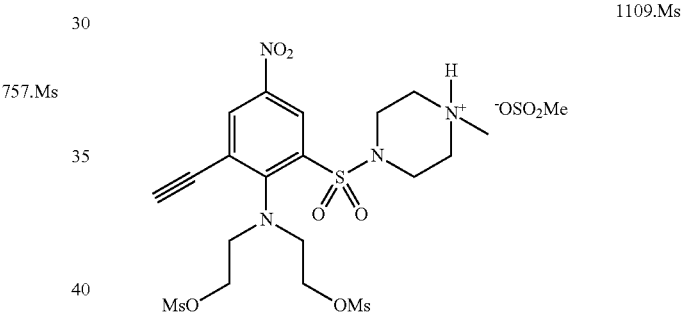

1109.Ms

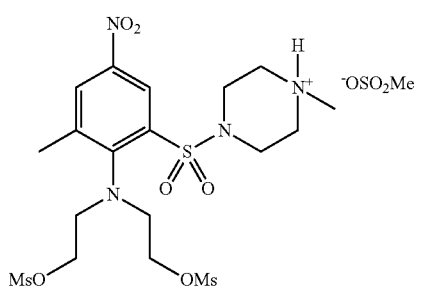

758.Ms

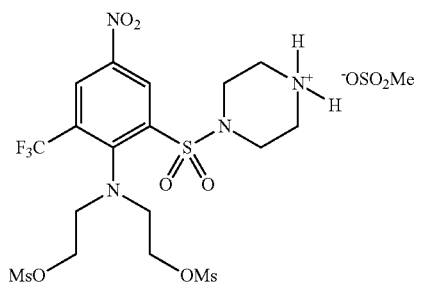

991.Ms

Synthesis of Compounds

It will be appreciated that the compounds of the invention may be prepared by any method. The inventors have synthesised compounds according to Scheme 4 below. In addition, Scheme 3 is provided to teach a skilled person how to produce the compounds referred to therein.

In a particular embodiment, the nitrobenzenesulfonamide prodrugs of the invention that are either unsubstituted at the 3-position or substituted with a range of substituents in the 3-position, can be prepared from 2-fluoro-5-nitrobenzene-1-sulfonyl chloride (V; A=H) or 3-substituted-2-fluoro-5-nitrobenzene-1-sulfonyl chlorides (V), respectively, by coupling to the appropriate primary or secondary amine (H-G) to give the sulfonamides (VI). Subsequent reaction with diethanolamine in dimethylsulfoxide/dichloromethane gives the diols (VII). Reaction of these with the appropriate alkylsulfonyl chloride or alkylsulfonic anhydride in dichloromethane under basic conditions gives the desired bis-alkylsulfonate prodrugs of Formula Ia. Further reaction with a single equivalent of lithium halide provides the asymmetric halo/alkylsulfonate prodrugs of Formula Ib, while reaction with excess lithium halide gives the symmetrical di-halo prodrugs of Formula Ic (Scheme 3).

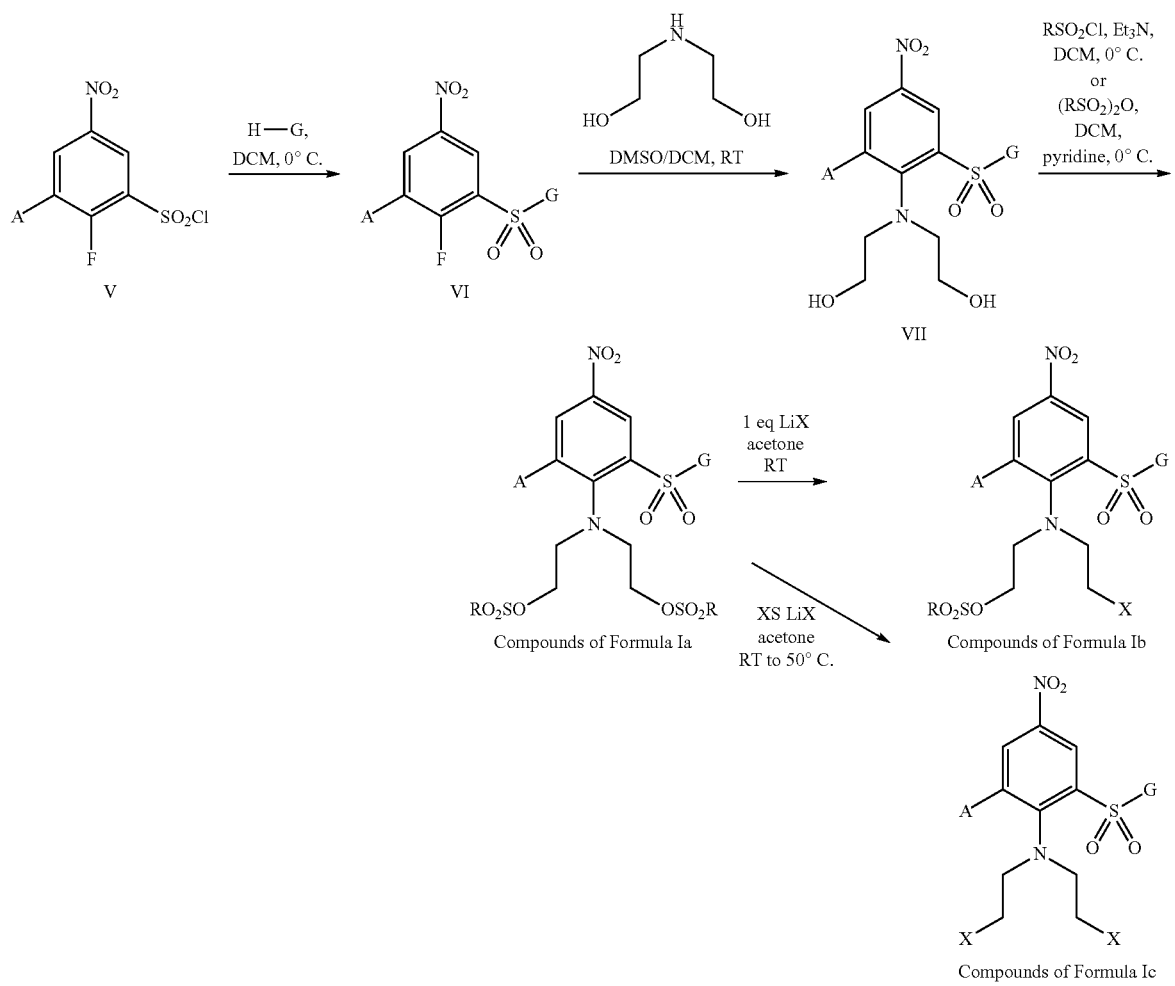

Scheme 3

Pharmaceutical Compositions

The invention also provides a pharmaceutical composition comprising a therapeutically effective amount of a compound of Formula (I) and a pharmaceutically acceptable excipient, adjuvant, carrier, buffer or stabiliser. The composition may be in the form of a tablet, capsule, powder, or liquid. The composition may be formulated for administration parenterally, preferably by intravenous infusion. The composition is preferably soluble in aqueous solution.

The concentration of the compound of the invention will depend on the nature of the compound used and the amount required to achieve a therapeutic effect once activated. It will be understood, however, that the amount of the compound administered will be determined by a physician, in the light of the relevant circumstances, including the condition to be treated, the chosen route of administration, the compound administered, the age, weight, and response of the individual patient, the severity of the patient's symptoms, and the treatment required. In certain embodiments, the composition comprises at least one compound of the invention in the form of pharmaceutically acceptable salts thereof, a hydrate thereof, or a solvate of any of the foregoing.

The composition may include a pharmaceutically acceptable diluent, carrier, buffer, stabiliser, excipient and/or adjuvant of any of the foregoing. The choice of diluent, carrier, buffer, stabiliser excipient and/or adjuvant can depend upon, among other factors, the desired mode of administration. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The composition may additionally include lubricating agents such as talc, magnesium stearate, and mineral oil, wetting agents, emulsifying and suspending agents, preserving agents such as methyl- and propylhydroxy-benzoates, sweetening agents, pH adjusting and buffering agents, toxicity adjusting agents, flavouring agents, and the like. The composition may be formulated so as to provide quick, sustained or delayed release of the active ingredient after administration to the patient by employing procedures known in the art. The composition may be formulated in unit dosage form, each dosage comprising a physically discrete unit suitable as a unitary dosage for humans and other mammals, each unit containing a predetermined quantity of active material calculated to produce the desired therapeutic effect, in association with a suitable pharmaceutical excipient, diluent, carrier and/or adjuvant.

Opportunities for non-systemic administration of an AKR1C3-activated prodrug to a patient exist allowing for relatively larger doses of prodrug to be delivered to tumour tissue relative to normal tissue. For example, intravesical instillation of a compound of the invention via a catheter directly into the bladder of a patient to treat AKR1C3 positive non-muscle-invasive bladder cancer and transcatheter arterial chemoembolization (TACE) therapy for hepatocellular carcinoma, where compound-loaded embolic particles can be introduced selectively to hepatic tumours via the hepatic artery or the compound can be introduced selectively to hepatic tumours via the hepatic artery followed by subsequent administration of an embolising agent via the hepatic artery.

Methods of Treatment

Compounds of the invention as described above have demonstrated efficacy in vitro and in vivo for ablation of AKR1C3-expressing cells. As such the invention provides a method of treatment of a hyperproliferative disorder comprising administering to a subject a compound of Formula (I). Preferably, the hyperproliferative disorder is characterised by the formation of neoplasms with substantial expression of AKR1C3.

WO 2010/044686 describes methods of determining an AKR1C3 profile from a sample from a patient and is incorporated herein by reference. Persons skilled in the art will readily understand and be able to determine those neoplasms in which the level of AKR1C3 is greater than in normal healthy tissues. However, by way of example, the methods described in WO 2010/044686, such as genotypic profiling, gene expression profiling, and protein expression profiling, may also be used.

It will be understood that certain patients or patient groups may exhibit different sensitivity to treatment compounds. WO 2010/044686 describes methods and procedures to determine drug sensitivity in patients to allow the identification of individualised patient profiles which will aid in treating diseases and disorders. In particular, WO 2010/044686 provides prognostic and predictive markers, which would facilitate an individualisation of therapy for each patient, thus accurately predicting patient response to treatments such as those of the present invention.

Although PR-104A and related dinitrobenzenecarboxamide and nitrobenzenecarboxamide analogues (e.g. SN33539, SN34947, SN34951, SN34118, SN33540, SN35028 and SN34454) have been shown to be activated by AKR1C3, there are no nitrobenzenesulfonamide prodrugs which have been shown to exhibit such AKR1C3-dependent activation. In addition, the compounds of the invention exhibit a number of advantageous properties when compared to PR-104A and related dinitrobenzenecarboxamide and nitrobenzenecarboxamide analogues. Accordingly, compounds of the invention provide alternative or improved therapeutic avenues for the treatment of hyperproliferative disorders characterised by the formation of neoplasms with substantial expression of AKR1C3. Such hyperproliferative disorders may be selected from acute myeloid leukaemia (AML), T-cell lineage acute lymphocytic leukaemia (T-ALL), chronic myeloid leukaemia (CML), hepatocellular carcinoma, non-muscle-invasive (superficial) bladder cancer, locally invasive bladder cancer, metastatic bladder cancer, gastric cancer, cervical cancer, pancreatic cancer, colon cancer, rectal cancer, oesophageal cancer, head and neck cancer, ovarian cancer, glioblastoma, sarcoma, endometrial cancer, prostate cancer, renal cancer and lung cancer.

The invention also provides the use of a compound of Formula (I) in the manufacture of a composition for the treatment of a hyperproliferative disorder. Preferably, the hyperproliferative disorder is characterised by the formation of neoplasms with substantial expression of AKR1C3.

The invention also provides the use of a compound of Formula (I) for the treatment of a hyperproliferative disorder. Preferably, the hyperproliferative disorder is characterised by the formation of neoplasms with substantial expression of AKR1C3.

While compounds of the invention will typically be used in therapy of human subjects, they may be used to target cells for ablation in other warm blooded animal subjects, such as other primates, which have a form of AKR1C3 that will metabolise such prodrugs.

Method of Cell Ablation

A cytotoxic metabolite is produced following metabolism/activation of a compound of the invention by an AKR1C3 enzyme. This cytotoxic metabolite has the capacity to ablate the cell expressing the AKR1C3 enzyme. Accordingly, the invention provides a method of cell ablation comprising the steps:

a. activating a compound of Formula (I) with at least one AKR1C3 enzyme to produce a cytotoxic metabolite capable of ablating a target cell; and b. contacting the target cell with the cytotoxic metabolite to ablate the cell.

An AKR1C3 prodrug may be useful for purging bone marrow before a bone marrow stem cell transplant. This could, for example, be in the treatment of leukaemia or for use in gene therapy involving transplant of genetically engineered stem cells to correct a mono-genetic disorder.

Current bone marrow purging (to kill off and clean out the bone marrow so that a transplant has a better chance of taking and therefore a better chance of therapeutic success) typically uses a combination of two toxic chemotherapies (e.g. cyclophosphamide and busulfan). These have severe side effects that are dose-limiting. Therefore, approximately 30% of patients do not have sufficient ablation of their bone marrow and do not get a full therapeutic benefit from the stem cell transplant.

An AKR1C3 prodrug may replace one of the cytotoxins and provide more extensive bone marrow ablation with less systemic toxicity. This is because CD34-positive bone marrow progenitor cells are known to express AKR1C3.

EXAMPLES

General Chemistry Experimental Information

All reagents and solvents were obtained from commercial sources. Flash chromatography was performed using silica gel (300 mesh). All reactions were monitored by TLC, using silica gel plates with fluorescence $F_{25}4$ and UV light visualization. $^1H$ NMR was recorded on a Brucker AV-400 spectrometer at 400 MHz or a Brucker AV-500 spectrometer at 125 MHz. $^{13}C$ NMR spectra was recorded on a Brucker AV-500 spectrometer at 125 MHz. Coupling constants (J) are expressed in hertz (Hz). Chemical shifts (δ) are reported in parts per million (ppm). The high resolution of ESI-MS was recorded on an Applied Biosystems Q-STAR Elite ESI-LC-MS/MS mass spectrometer. The purity of compounds was determined to be over 95% using reverse-phase HPLC analysis. HPLC instrument: Dionex Summit HPLC (Column: Diamonsil C18, 5.0 mm, 4.6×250 mm (Agilent Technologies); detector: PDA-100 photodiode array; injector: ASI-100 autoinjector; pump: p-680A). The flow rate was 1.0 mL/min and mobile phase was MeOH in $H_2O$ with 0.1% modifier (ammonia v/v).

Example 1: ((2-((4-methylpiperazin-1-yl)sulfonyl)-4-nitrophenyl)azanediyl)bis(ethane-2,1-diyl) dimethanesulfonate (641)

A synthetic route for the preparation of 5-nitrobenzenesulfonamide prodrugs (562-564, 566-568, 601-603, 605-607, 640-642, 644-646) of the present invention is outlined in Scheme 4. 2-Fluoro-5-nitrobenzene-1-sulfonyl chloride (2031) coupling with 1-methylpiperazine, 1-ethylpiperazine, 1-allylpiperazine, 1-phenylpiperazine or 1-benzylpiperazine gave the desired sulfonamides 2033-2037, respectively. Reaction of these with diethanolamine in dimethylsulfoxide/dichloromethane gave the diols 2039-2043, respectively. Reaction with methanesulfonyl chloride or methanesulfonic anhydride in dichloromethane (DCM) under basic conditions gave the bis-methanesulfonate ester prodrugs 641, 642, 2045, 645 and 646, respectively. Bis-methanesulfonate ester prodrug 640 was prepared by the reaction of the sulfonyl chloride 2031 with tert-butyl piperazine-1-carboxylate to give sulfonamide 2032, followed by condensation with diethanolamine to give diol 2038, bis-mesylation to give 2044 and subsequent deprotection with methanesulfonic acid. Osmium tetroxide mediated dihydroxylation of allylpiperazine 2045 gave the desired bis-methanesulfonate prodrug 644. Further reaction of prodrugs 640-642 and 644-646 with a single equivalent of lithium bromide in acetone at room temperature gave the asymmetric bromo/methanesulfonate prodrugs 601-603 and 605-607, respectively. Reaction of prodrugs 640-642 and 644-646 with excess lithium bromide in acetone at room temperature to 50° C. gave the symmetrical di-bromo prodrugs 562-564 and 566-568, respectively.

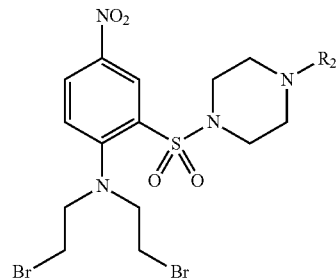

562: R₂ = H
563: R₂ = Me
564: R₂ = Et
566: R₂ = CH₂CH(OH)CH₂OH
567: R₂ = phenyl
568: R₂ = benzyl

1-((2-Fluoro-5-nitrophenyl)sulfonyl)-4-methylpiperazine (2033)

2-Fluoro-5-nitrobenzenesulfonyl chloride (2031) (1.10 g, 4.59 mmol) in CH$_2$Cl$_2$ (10 mL) was treated with dropwise addition of 1-methylpiperazine (920 mg, 9.18 mmol) at 0° C. The reaction mixture was stirred at 0° C. for 30 min then diluted with CH$_2$Cl$_2$ and washed with water. The organic phase was dried over Na$_2$SO$_4$ and concentrated under reduced pressure. The crude product was purified by flash column chromatography on silica gel eluting with CH$_2$Cl$_2$/MeOH (15:1) to give 1-((2-fluoro-5-nitrophenyl)sulfonyl)-4-methylpiperazine (2033) (1.17 g, 84%) as a yellow oil. $^1$H NMR [(CD$_3$)$_2$SO] δ 8.61 (ddd, J=9.0, 4.0, 2.9 Hz, 1H), 8.45 (dd, J=5.9, 2.9 Hz, 1H), 7.81 (d, J=9.3 Hz, 1H), 3.16-3.14 (m, 4H), 2.37-2.35 (m, 4H), 2.16 (s, 3H). HRMS (ESI) calc: for C$_{11}$H$_{15}$FN$_3$O$_4$S (MH$^+$) m/z 304.0762, found: 304.0760.

2,2'-((2-((4-methylpiperazine-1-yl)sulfonyl)-4-nitrophenyl)azanediyl)bis(ethan-1-ol) (2039)

A solution of 1-((2-fluoro-5-nitrophenyl)sulfonyl)-4-methylpiperazine (2033) (888 mg, 2.93 mmol) in DMSO (2 mL) and CH$_2$Cl$_2$ (1 mL) was treated with diethanolamine (616 mg, 5.86 mmol). The reaction mixture was stirred at room temperature for 4 h then poured into a beaker of ice-water, treated with sodium chloride to provide a saturated solution and extracted with EtOAc (×4). The combined organic phases were dried over Na$_2$SO$_4$ and evaporated to dryness under reduce pressure. The yellow gum was purified by flash column chromatography on silica gel eluting with CH$_2$Cl$_2$/MeOH (13:1) to give 2,2'-((2-((4-methylpiperazine-1-yl)sulfonyl)-4-nitrophenyl)azanediyl)bis(ethan-1-ol) (2039) (849 mg, 75%) as a yellow gum. $^1$H NMR [(CD$_3$)$_2$SO] δ 8.49 (d, J=2.8 Hz, 1H), 8.28 (dd, J=9.2, 2.9 Hz, 1H), 7.53 (d, J=9.2 Hz, 1H), 4.57 (t, J=4.9 Hz, 2H), 3.56-3.49 (m, 8H), 3.07-3.05 (m, 4H), 2.34-2.32 (m, 4H), 2.16 (s, 3H). LRMS (APCI) calc: for C$_{15}$H$_{25}$N$_4$O$_6$S (MH$^+$) m/z 389.4, found: 389.8.

((2-((4-methylpiperazine-1-yl)sulfonyl)-4-nitrophenyl)azanediyl)bis(ethane-2,1-diyl) dimethanesulfonate (641)

Method 1: Mesylation Using Methane Sulfonyl Chloride (MsCl)

A solution of 2,2'-((2-((4-methylpiperazine-1-yl)sulfonyl)-4-nitrophenyl)azanediyl)bis(ethan-1-ol) (2039) (813 mg, 2.09 mmol) in CH$_2$Cl$_2$ (27 mL) was treated with Et$_3$N (1.02 mL, 7.32 mmol) and dropwise addition of MsCl (486 µL, 6.28 mmol) at 0° C. The reaction mixture was stirred at 0° C. for 20 min then diluted with CH$_2$Cl$_2$, washed with saturated solution of NaHCO$_3$, dried with Na$_2$SO$_4$ and concentrated under reduced pressure. The residue was purified by flash column chromatography on silica gel eluting with CH$_2$Cl$_2$/Et$_2$O/MeOH (13:10:2) to give ((2-((4-methylpiperazine-1-yl)sulfonyl)-4-nitrophenyl)azanediyl)bis(ethane-2,1-diyl) dimethanesulfonate (641) (836 mg, 73%) as a yellow solid, m.p. 137-140° C.; $^1$H NMR [(CD$_3$)$_2$SO] δ 8.48 (d, J=2.8 Hz, 1H), 8.37 (dd, J=9.0, 2.8 Hz, 1H), 7.66 (d, J=9.1 Hz, 1H), 4.33 (t, J=5.3 Hz, 4H), 3.77 (t, J=5.3 Hz, 4H), 3.14 (s, 6H), 3.05-3.03 (m, 4H), 2.35-2.33 (m, 4H), 2.15 (s, 3H). HRMS (ESI) calc: for C$_{17}$H$_{28}$N$_4$NaO$_{10}$S$_3$ (MNa$^+$) m/z 567.0860, found: 567.0845.

Method 2: Mesylation Using Methane Sulfonic Anhydride (Ms$_2$O)

A solution of 2,2'-((2-((4-methylpiperazine-1-yl)sulfonyl)-4-nitrophenyl)azanediyl)bis(ethan-1-ol) (2039) (635 mg, 1.63 mmol) in CH$_2$Cl$_2$ (20 mL) was treated with pyridine (463 µL, 5.72 mmol), DMAP (20 mg, 0.16 mmol) and portionwise addition of Ms$_2$O (854 mg, 4.90 mmol) at 0° C. The reaction mixture was stirred at 0° C. for 20 min then warmed to the room temperature, diluted with CH$_2$Cl$_2$, washed with saturated solution of NaHCO$_3$, dried with Na$_2$SO$_4$ and concentrated under reduced pressure. The residue was purified by flash column chromatography on alumina eluting with EtOAc/MeOH (200:1) to give ((2-((4-methylpiperazine-1-yl)sulfonyl)-4-nitrophenyl)azanediyl)bis(ethane-2,1-diyl) dimethanesulfonate (641) (768 mg, 86%) as a yellow solid.

Example 2: N,N-bis(2-bromoethyl)-2-((4-methylpiperazin-1-yl)sulfonyl)-4-nitroaniline (563)

Compound 563 was prepared according to the synthetic route outlined in Scheme 4.

$^1$H NMR [(CD$_3$)$_2$SO] δ 8.49 (d, J=2.8 Hz, 1H), 8.35 (dd, J=9.1, 2.8 Hz, 1H), 7.67 (d, J=9.1 Hz, 1H), 3.84 (t, J=7.1 Hz, 4H), 3.59 (t, J=7.1 Hz, 4H), 3.13-3.11 (m, 4H), 2.37-2.35 (m, 4H), 2.17 (s, 3H). HRMS (ESI) calc: for C$_{15}$H$_{23}$Br$_2$N$_4$O$_4$S (MH$^+$) m/z 512.9801, found: 512.9798.

Example 3: 3-(4-((2-(bis(2-bromoethyl)amino)-5-nitrophenyl)sulfonyl)piperazin-1-yl)propane-1,2-diol (566)

Compound 566 was prepared according to the synthetic route outlined in Scheme 4.
$^1$H NMR [(CD$_3$)$_2$SO] δ 8.48 (d, J=2.8 Hz, 1H), 8.34 (dd, J=9.1, 2.8 Hz, 1H), 7.67 (d, J=9.1 Hz, 1H), 4.47 (t, J=5.4 Hz, 1H), 4.40 (d, J=4.6 Hz, 1H), 3.84 (t, J=7.0 Hz, 4H), 3.60 (t, J=7.0 Hz, 4H), 3.57-3.54 (m, 1H), 3.28-3.26 (m, 2H), 3.12-3.10 (m, 4H), 2.47-2.44 (m, 4H), 2.41-2.37 (m, 1H), 2.26-2.21 (m, 1H). HRMS (ESI) calc: for C$_{17}$H$_{26}$Br$_2$N$_4$NaO$_6$S (MNa$^+$) m/z 594.9832, found: 594.9804.

Example 4: 2-((2-bromoethyl)(2-((4-methylpiperazin-1-yl)sulfonyl)-4-nitrophenyl)amino)ethyl methanesulfonate (602)

Compound 602 was prepared according to the synthetic route outlined in Scheme 4.
$^1$H NMR [(CD$_3$)$_2$SO] δ 8.48 (d, J=2.8 Hz, 1H), 8.36 (dd, J=9.0, 2.8 Hz, 1H), 7.66 (d, J=9.1 Hz, 1H), 4.32 (t, J=5.3 Hz, 2H), 3.83 (t, J=7.1 Hz, 2H), 3.78 (t, J=5.3 Hz, 2H), 3.61 (t, J=7.1 Hz, 2H), 3.14 (s, 3H), 3.09-3.07 (m, 4H), 2.36-2.34 (m, 4H), 2.16 (s, 3H). HRMS (ESI) calc: for C$_{16}$H$_{26}$BrN$_4$O$_7$S$_2$ (MH$^+$) m/z 529.0421, found: 529.0414.

Example 5: ((2-((4-ethylpiperazin-1-yl)sulfonyl)-4-nitrophenyl)azanediyl)bis(ethane-2,1-diyl) dimethanesulfonate (642)

Compound 642 was prepared according to the synthetic route outlined in Scheme 4.
$^1$H NMR [(CD$_3$)$_2$SO] δ 8.47 (d, J=2.8 Hz, 1H), 8.37 (dd, J=9.0, 2.8 Hz, 1H), 7.66 (d, J=9.1 Hz, 1H), 4.34 (t, J=5.3 Hz, 4H), 3.78 (t, J=5.2 Hz, 4H), 3.14 (s, 6H), 3.05-3.02 (m, 4H), 2.40-2.38 (m, 4H), 2.31 (q, J=7.2 Hz, 2H), 0.94 (t, J=7.2 Hz, 3H). HRMS (ESI) calc: for C$_{18}$H$_{31}$N$_4$O$_{10}$S$_3$ (MH$^+$) m/z 559.1197, found: 559.1212.

Example 6: 4-((2-(bis(2-((methylsulfonyl)oxy)ethyl)amino)-5-nitrophenyl)sulfonyl)-1-methylpiperazin-1-ium methanesulfonate (641.Ms)

((2-((4-Methylpiperazine-1-yl)sulfonyl)-4-nitrophenyl) azanediyl)bis(ethane-2,1-diyl) dimethanesulfonate (641) (1.81 g, 3.32 mmol) in CH$_2$Cl$_2$ (35 mL) and MeOH (70 mL) was treated with methane sulfonic acid (259 µL, 3.99 mmol). After stirring at room temperature for 1.5 h, the solvents were removed to half a volume by evaporation and the yellow solid was collected by filtration to provide 4-((2-(bis (2-((methylsulfonyl)oxy)ethyl)amino)-5-nitrophenyl)sulfonyl)-1-methylpiperazine-1-ium methanesulfonate (641.Ms) (2.05 g, 96%) as a yellow solid, m.p. 146-148° C.; $^1$H NMR [(CD$_3$)$_2$SO] δ 9.50 (br, s, 1H), 8.47 (d, J=2.8 Hz, 1H), 8.43 (dd, J=9.0, 2.8 Hz, 1H), 7.73 (d, J=9.1 Hz, 1H), 4.36 (t, J=5.3 Hz, 4H), 3.84-3.81 (m, 2H), 3.76 (t, J=5.2 Hz, 4H), 3.43-3.37 (m, 2H), 3.15 (s, 6H), 3.11-3.09 (m, 2H), 2.82 (s, 3H), 2.80-2.77 (m, 2H), 2.30 (s, 3H). Anal. (C$_{18}$H$_{32}$N$_4$O$_{13}$S$_4$) calc: C, 33.74; H, 5.03; N, 8.74; found: C, 33.54; H, 4.92; N, 8.51.

Example 7: 4-((2-(bis(2-((methylsulfonyl)oxy)ethyl)amino)-5-nitrophenyl)sulfonyl)piperazin-1-ium methanesulfonate (640.Ms)

Compound 640.Ms was prepared according to the method described for compound 641.Ms.
M.p. 147-149° C.; $^1$H NMR [(CD$_3$)$_2$SO] δ 8.57 (br, s, 2H), 8.47 (d, J=2.8 Hz, 1H), 8.43 (dd, J=9.0, 2.8 Hz, 1H), 7.72 (d, J=9.0 Hz, 1H), 4.36 (t, J=5.2 Hz, 4H), 3.76 (t, J=5.1 Hz, 4H), 3.24-3.22 (m, 4H), 3.17-3.15 (m, 4H), 3.15 (s, 6H), 2.29 (s, 3H). Anal. (C$_{17}$H$_3$N$_4$O$_{13}$S$_4$) calc: C, 32.58; H, 4.82; N, 8.94; found: C, 32.60; H, 4.75; N, 8.76.

Example 8: Metabolism of Prodrugs of the Present Invention by Recombinant Human AKR1C3

Metabolism of prodrugs of the invention by recombinant human AKR1C3 was determined relative to positive control compounds PR-104A (Scheme 1), SN33539, SN35028, SN34947, SN34951, SN34118 and SN34454 (Scheme 2).

Materials and Methods

Purification of Recombinant AKR1C3 Enzyme

*E. coli* BL21(DE3) cells expressing the pET22b-AKR1C3 construct with a C-terminal hexahistidine (His$_6$) tag and constitutive promoter was generated. Colonies of these transformed *E. coli* cells were grown in LB agar medium containing 100 µg/mL of ampicillin. A single colony was picked the following day and grown in 400 mL batches of bacterial medium containing ampicillin (100 µg/mL) at 37° C., with continuous shaking at 200 rpm overnight. Bacterial cultures were pelleted by centrifugation (4000×g, 15 minutes) and resuspended in lysis buffer (10 mL/400 mL culture). The cells were disrupted by sonication (Sonicator 3000, Misonix) and centrifuged at 14,000 rpm for 30 minutes (at 4° C.). The cleared lysate was filtered in successive filters containing pore sizes of 1.20 µm, 0.8 µm and 0.2 µm and loaded onto a nickel-agarose affinity chromatography column on an ÄKTA Purifier system. The column was washed with 20 mL of the lysis buffer and the His$_6$-tagged AKR1C3 protein was eluted with lysis buffer supplemented with 500 mM imidazole. The protein was further purified by a liquid chromatography gel filtration column (Superdex 200 HR16/60) using lysis buffer (supplemented with 5% v/v glycerol) and 1 mM DTT (pH 7.0) at a flow rate of 0.3 mL/min. Protein was monitored by absorbance at 280 nm, and purity of the fractions (1 mL) was assessed by SDS-PAGE. Active fractions containing the purified protein were pooled and concentrated by centrifugation (3,000×g, 4° C.) on a Vivaspin concentrator (MWCO 10,000 cutoff; GE Healthcare). The protein containing solution was supplemented with glycerol (to a final concentration of 15%, v/v) and NADP$^+$ was added to a final concentration of 2 mM.

Kinetics Assay

Kinetic parameters of compounds of the invention were determined in a 96-well plate format. The 100 mM potassium phosphate buffer used in this assay was made with the following reagents to a pH of 7.4:
  0.5 M K$_2$HPO$_4$— 8.2 mL
  0.5 M KH$_2$PO$_4$— 1.8 mL
  BSApowder—25 mg
  Milli Q water—40 mL For the assay, 2 µL of varying substrate concentrations were incubated with 94 µL of the potassium phosphate buffer and 2 µL of 5 mM NADPH for 5 minutes in the pre-warmed (37° C.) plate chamber of a Molecular Devices SpectraMax M2 plate reader. Purified AKR1C3 enzyme (2 µL) was added to a final concentration of 100 µM in each well using an Eppendorf electronic multi-channel pipette. Absorbance measurements were recorded immediately upon addition of enzyme over a period of 5 minutes at a wavelength of 400 nm. Absorbance changes for each compound concentration were plotted against time to obtain the rate of absorbance change over the 5 minute period. The rate of absorbance change was then plotted against the compound concentration and non-linear regression analysis and Michaelis-Menten curve fitting performed on GraphPad-Prism (version 5.00 for Windows, GraphPad Software, San Diego Calif. USA) in order to determine kinetic parameters of compounds.

Results

Compounds of the invention were shown to be superior substrates for AKR1C3 compared to PR-104A. The compounds demonstrated improved affinity for AKR1C3 compared to PR-104A, with a 2-fold to 4-fold decrease in $K_m$ compared to PR-104A. All of the compounds demonstrated an acceptable catalytic turnover with $k_{cat}$ spanning the range of 28.1 s$^{-1}$ to 78.5 s$^{-1}$. All of the compounds demonstrated improved catalytic efficiency compared to PR-104A, as determined by the key kinetic parameter $k_{cat}/K_m$ which was improved by 6.4 to 9.3-fold (Table 1). While the catalytic efficiency of known compounds SN33539, SN35028, SN34947, SN34951, SN34118 and SN34454 was also found to be improved over PR-104A, as determined by increased $k_{cat}/K_m$, it was surprisingly found that selected examples (SN35028, SN34947 and SN34951) demonstrated inhibition of AKR1C3 metabolism at concentrations above 20 μM (FIG. 1). This is a predicted consequence of the significantly increased binding affinity for AKR1C3 for these compounds over PR-104A and the compounds of the present invention. SN33539, SN35028, SN34947, SN34951, SN34118 and SN34454 all possess $K_m$<10 μM. The unfavourable property of inhibition of substrate metabolism at high concentrations of substrate was not observed for compound 641 at concentrations as high as 300 μM (FIG. 1). This finding was surprising and favourable for an AKR1C3-activated prodrug, reflecting an optimal balance of affinity for the AKR1C3 catalytic site and substrate turnover.

TABLE 1

Kinetic parameters for metabolism of prodrugs by recombinant human AKR1C3

| Compound | $K_m$ (μM) | $k_{cat}$ (s$^{-1}$) | $k_{cat}/K_m$ (M$^{-1}$ s$^{-1}$) |
| --- | --- | --- | --- |
| PR-104A | 72.9 | 18.7 | 256,206 |
| SN33539 | 6.7 | 28.6 | 4,271,612 |
| SN35028 | 7.3 | 29.1 | 3,980,137 |
| SN34947 | 7.8 | 23.8 | 3,059,088 |
| SN34951 | 8.5 | 29.0 | 3,419,286 |
| SN34118 | 9.0 | 18.7 | 2,045,579 |
| SN34454 | 3.0 | 5.2 | 1,738,985 |
| 566 | 32.2 | 67.1 | 2,084,888 |
| 602 | 33.1 | 78.5 | 2,370,091 |
| 605 | 17.1 | 28.1 | 1,645,614 |
| 641 | 21.5 | 41.3 | 1,922,414 |

Example 9: AKR1C3-Dependent Cellular Cytotoxicity in HCT-116 Cells

The cellular cytotoxicity of compounds of the invention resulting from AKR1C3-dependent metabolism of the compounds can readily be observed in anti-proliferative IC50 testing in isogenic cell lines that have been engineered to over-express human AKR1C3, relative to their wild-type counterparts that have been selected for their comparatively low levels of endogenous AKR1C3 expression (by Western blot analysis). The direct role of AKR1C3 in metabolism and cytotoxicity of the compounds is further supported for selected examples by repeat anti-proliferative experiments in the presence of a potent and selective small molecule inhibitor of AKR1C3, SN34037 (Flanagan et al., Bioorganic & Medicinal Chemistry (2014), 22(3), 967-977).

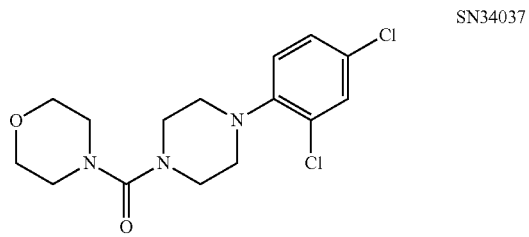 [SMILES: O=C(N1CCOCC1)N1CCN(c2ccc(Cl)cc2Cl)CC1]

Materials and Methods
Anti-Proliferative IC50 Assay Experimental Methods
Solutions required
40% (w/v) Trichloroacetic acid (TCA)
TCA—500 g
Milli Q water—750 mL
0.4% (w/v) Sulforhodamine B (SRB)
SRB— 4 g
Acetic acid—10 mL
Milli Q water—986 mL
10 mM unbuffered Tris base [tris(hydroxymethyl)aminomethane)]
Tris—1.2 g
Milli Q water—1 L
The pH of this solution was adjusted to 10.5.

Cell Seeding and Compound Addition

Four hundred cells were seeded in a volume of 100 μL in each well of a 96-well plate. The cells were left in a humidified incubator (37° C., 5% CO$_2$) for 2 hours in order to enable attachment to the surface of the wells prior to compound addition. All compounds were prepared as stocks in DMSO and stored at −80° C. Frozen stocks of compounds were thawed immediately prior to addition to cells. Working solutions of each compound were made in α-MEM+5% FBS (v/v) at 3 times the required final concentration for the top well. The final concentration of DMSO in the α-MEM solution was ensured to not exceed 1% of the total volume. 50 μL of the working solution was added to the top wells (in duplicates) and gently mixed. The solubility of some compounds precluded the working solution in α-MEM to be 3 times the desired top well concentration. Hence, the media of such top wells were removed and replaced with 150 μL of the working solution. A 3-fold serial dilution was carried out along the plate starting from the top well. The first column of wells on the plate served as blanks (containing α-MEM+FBS) and the second column served as control wells (containing cells with no compound added). Following compound addition, the plates were incubated for 4 hours in a humidified incubator (37° C., 5% CO$_2$).

Washing and Staining Plates

Following the 4 hour compound exposure, the 96-well plates were washed three times by aspirating media with an Immuno Washer (Nunc) and each well replaced with 150 μL of α-MEM+5% (v/v) FBS+1% (v/v) P/S. The plates were left in a humidified incubator (37° C., 5% CO$_2$) for 5 days to enable cell growth. The cells in 96-well plates were fixed 5 days after compound exposure by adding 50 μL of a 40% (w/v) trichloroacetic acid (TCA) solution so as to obtain a final TCA concentration of 10% in each well. The plates were left in the refrigerator (4° C.) for 1 hour and subsequently rinsed 3 times in tap water. Any excess water was left to drain and the cells were stained with 50 μL of 0.4%

(w/v) sulforhodamine B (SRB). The plates with the SRB stain were left in the dark for 30 minutes. Excess stain was removed from the wells by rinsing the plates 4 times in water containing 1% (v/v) acetic acid. The stain was solubilised by adding 100 µL of 10 mM unbuffered Tris (pH 10.5) to each well and the plates were left in a shaker in a dark environment at room temperature for at least 1 hour. The absorbance values of the wells were determined by an ELx 808 Absorbance Microplate Reader (Bio-Tek Instruments, Winooski, Vt., USA), with the wavelength of the measurement filter set at 490 nm and a reference filter set at 450 nm. The absorbance of the reference filter was subtracted from the measurement filter to obtain a final absorbance of $\lambda_{490-450}$ nm. The absorbance data was analysed and $IC_{50}$ values determined by the KC4 microplate data analysis software (KC4™ V3.4, Bio-Tek).

AKR1C3 Inhibition with SN34037

Anti-proliferative IC50 assays were repeated as described above including the addition of 3 µM SN34037, a selective and potent small molecule inhibitor of AKR1C3.

Results

HCT116 colon cancer cells demonstrated a 687-fold to 4260-fold increase in sensitivity to compounds of the invention when the cells express AKR1C3 (Table 2). This is considerably greater than the 29-fold to 98-fold increase in sensitivity observed for the control compounds (PR-104A, SN27686, SN33539, SN35028, SN34947, SN34951 and SN34118). A direct comparison of a known nitrobenzenecarboxamide (SN34118) and a nitrobenzenesulfonamide of the invention (compound 563) shows that compound 563 is 43-fold more cytotoxic to AKR1C3-expressing HCT116 cells than SN34118, a surprising result that could not be readily predicted. The inventors have clearly demonstrated a surprising finding in that, although sterically similar (isosteres), sulfonamide and carboxamide substituents on the aromatic ring have markedly different effects on sensitivity. Further, for all compounds studied, the increase in cytotoxicity resulting from expression of AKR1C3 was found to be fully reversed by addition of an AKR1C3 inhibitor (SN34037), directly implicating metabolism of the prodrugs by AKR1C3 in the observed increase in cytotoxicity. As an important control, introduction of SN34037 has no anti-proliferative effects in wild-type HCT116 cells treated with compounds of the invention.

Example 10: AKR1C3-Dependent Cellular Cytotoxicity in Hepatocellular Carcinoma Cells Materials and methods used are as described for Example 9. Comparable with the results observed in wild-type and AKR1C3 over-expressing HCT116 cells, SNU398 hepatocellular carcinoma cells demonstrated up to a 5,150-fold increase in sensitivity to preferred compounds of the invention when the cells express AKR1C3 (Table 3). This is a surprising finding and considerably greater than the approximately 77-fold, 270-fold and 400-fold increase in sensitivity observed for PR-104A, SN33540 and SN34454, respectively. In all cases, this increase in cytotoxicity resulting from expression of AKR1C3 can be substantially reversed by addition of an AKR1C3 inhibitor (SN34037), directly implicating metabolism of the prodrugs by AKR1C3 in the observed increase in cytotoxicity. As an important control, introduction of SN34037 had no anti-proliferative effects in wild-type SNU398 cells treated with compounds of the invention.

TABLE 3

Anti-proliferative IC50 (µM) of compounds of the invention in wild-type SNU398 hepatocellular carcinoma cells and SNU398 hepatocellular carcinoma cells engineered to over-express AKR1C3, with and without addition of 3 µM of a selective small molecule inhibitor of AKR1C3 (SN34037).

| | Anti-proliferative IC50 (µM) | | | |
|---|---|---|---|---|
| | SNU398-WT | | SNU398-AKR1C3 | |
| Compound | | +AKR1C3 Inhibitor | | +AKR1C3 Inhibitor |
| PR-104A | 89.8 | 92.4 | 1.16 | 89.9 |
| SN33540 | 230.9 | 248.1 | 0.844 | 193.2 |
| SN34454 | 60.5 | 48.9 | 0.150 | 62.7 |
| 563 | 6.93 | 5.87 | 0.015 | 4.19 |
| 566 | 9.64 | 10.2 | 0.011 | 6.41 |
| 602 | 6.74 | 6.65 | 0.003 | 2.66 |
| 605 | 16.2 | 14.4 | 0.028 | 10.5 |
| 640 | 8.47 | 8.49 | 0.026 | 6.54 |
| 641 | 10.3 | 15.4 | 0.004 | 5.07 |
| 642 | 10.3 | 12.1 | 0.002 | 1.28 |
| 644 | 73.8 | 68.4 | 0.262 | 63.7 |

TABLE 2

Anti-proliferative IC50 (µM) of compounds of the invention in wild-type HCT116 colon cancer cells and HCT116 colon cancer cells engineered to over-express AKR1C3, with and without addition of 3 µM of a selective small molecule inhibitor of AKR1C3 (SN34037) for selected examples.

| Compound | HCT116-WT IC50 (µM) | HCT116-WT + AKR1C3 Inhibitor IC50 (µM) | HCT116-AKR1C3 IC50 (µM) | IC50 Ratio WT:AKR1C3 | HCT116-AKR1C3 + AKR1C3 Inhibitor IC50 (µM) |
|---|---|---|---|---|---|
| PR-104A | 55.8 | 70.7 | 1.12 | 50 | 41.8 |
| SN27686 | 42.6 | | 1.46 | 29 | |
| SN33539 | 135.0 | | 2.38 | 57 | |
| SN35028 | >150 | | 4.15 | >36 | |
| SN34947 | 66.8 | | 2.41 | 28 | |
| SN34951 | >150 | | 3.97 | >38 | |
| SN34118 | 38.2 | 29.3 | 0.389 | 98 | 23.9 |
| 563 | 7.34 | 5.89 | 0.009 | 816 | 3.26 |
| 566 | 3.34 | 3.93 | 0.001 | 3340 | 1.72 |
| 602 | 4.26 | 4.33 | 0.001 | 4260 | 1.78 |
| 605 | 6.18 | 6.90 | 0.009 | 687 | 3.54 |
| 640 | 4.22 | 4.10 | 0.009 | 469 | 2.06 |
| 641 | 5.91 | 6.40 | 0.002 | 2955 | 3.11 |
| 642 | 1.93 | 2.37 | 0.001 | 1930 | 0.828 |
| 644 | 106.6 | 111.8 | 0.109 | 978 | 47.0 |

Example 11: AKR1C3-Dependent Cellular Cytotoxicity in Lung Cancer and Hepatocellular Carcinoma Cells Materials and methods used are as described for Example 9. Compounds of the invention demonstrated potent anti-proliferative activity in wild-type H460 lung cancer cells and wild-type PLC/PRF/5 hepatocellular carcinoma cells known to endogenously express AKR1C3 at high and moderate levels, respectively, by Western blot analysis.

Compounds of the invention demonstrated IC50's in the range of 3 to 27 nM in H460 lung cancer cells, being 100-fold to 900-fold more cytotoxic than PR-104A in this cell line (IC50=2.7 µM). Compound 641 was found to be 135-fold, 179-fold and 520-fold more cytotoxic in H460 cells than SN34454, SN33540 and SN34118, respectively. A further direct comparison of known carboxamides and sulphonamides of the invention can be seen when comparing SN34118 with compound 563 and SN34454 with compound 602. The compounds of the invention are 82-fold and 102-fold, respectively, more cytotoxic in H460 cells than known direct comparator compounds. These findings are surprising and could not reasonably have been predicted. In all cases, the cytotoxicity demonstrated was found to be ameliorated by addition of an AKR1C3 inhibitor (SN34037), directly implicating metabolism of the compounds by endogenous AKR1C3 in the observed cytotoxicity in wild-type H460 cells (Table 4).

Compounds of the invention demonstrated low micromolar IC50's in PLC/PRF/5 hepatocellular carcinoma cells, being up to 90-fold more cytotoxic than PR-104A in this cell line (IC50=108.4 µM). As a further direct comparison, compound 602 was found to be 94-fold more cytotoxic than SN34454 in this cell line. In all cases, the cytotoxicity demonstrated was found to be ameliorated by addition of an AKR1C3 inhibitor (SN34037), directly implicating metabolism of the prodrugs by endogenous AKR1C3 in the observed cytotoxicity in wild-type PLC/PRF/5 cells (Table 4). The degree of cytotoxicity observed in this cell line in vitro for compounds of the invention (and PR-104A) is considerably less than that observed in HCT116-AKR1C3, SNU398-AKR1C3 and wild-type H460 cells, consistent with the lower levels of endogenous expression of AKR1C3 observed in this cell line in vitro.

TABLE 4

Anti-proliferative IC50 (µM) of compounds of the invention in wild-type H460 lung cancer cells and wild-type PLC/PRF/5 hepatocellular carcinoma cells known to express AKR1C3 at high and moderate levels, respectively, with and without addition of 3 µM of a selective small molecule inhibitor of AKR1C3 (SN34037).

| | Anti-proliferative IC50 (µM) | | | |
|---|---|---|---|---|
| | H460-WT | | PLC/PRF/5-WT | |
| Compound | | +AKR1C3 Inhibitor | | +AKR1C3 Inhibitor |
| PR-104A | 2.70 | 50.0 | 108.4 | 181.2 |
| SN33540 | 0.536 | 97.7 | 83.9 | 247.8 |
| SN34118 | 1.56 | 28.9 | 114.6 | 174.2 |
| SN34454 | 0.406 | 46.0 | 111.4 | 131.4 |
| 563 | 0.019 | 3.09 | 4.20 | 21.5 |
| 566 | 0.004 | 4.03 | | |
| 602 | 0.004 | 4.19 | 1.19 | 23.7 |
| 605 | 0.025 | 7.80 | | |
| 640 | 0.027 | 5.88 | | |
| 641 | 0.003 | 5.86 | 1.42 | 40.5 |
| 642 | 0.001 | 2.24 | | |
| 644 | 0.387 | 88.3 | | |

Example 12: Resistance to Activation by Hypoxia in Wild-Type Cell Lines

PR-104A was initially designed and optimised as a hypoxia-selective cytotoxin (Patterson et al, Clinical Cancer Research, 2007, 13, 3922-3932). In the context of an AKR1C3-activated prodrug, this route of activation is considered off-mechanism and may potentially be undesirable, leading to off-target toxicities in a subject. Preferred compounds of the invention have been determined to be substantially resistant to hypoxia-dependent activation and cytotoxicity in wild-type HCT116 colon cancer cells. HCT116 cells were treated with compounds of the invention under either oxic or anoxic conditions and then their degree of anti-proliferative activity determined.

Materials and Methods

Evaluation of Cytotoxicity Under Hypoxic Conditions

Selected compounds were evaluated for cytotoxic potential ($IC_{50}$) under anoxic conditions. The same procedures as described above for Examples 9-11 were carried out in a Bactron anoxic chamber (Sheldon Manufacturing Inc) with internal 37° C. incubators where palladium catalyst scrubbed gas (90% $N_2$, 5% $H_2$, 5% $CO_2$) ensured severe anoxia (<0.001% $O_2$) in the whole chamber. All materials required (including cells) were taken into the chamber through two cycles of vacuum and gassing with 100% $N_2$, followed by a single cycle with 5% $CO_2$ and 5% hydrogen in nitrogen. All experimental materials were placed in the anoxic chamber at least 3 days prior to the day required for the experiment in order to remove any traces of residual $O_2$. The medium used for the 96-well plates in the anoxic chamber consisted of α-MEM+10% (v/v) FBS+1% (v/v) additives (1 M β-D-Glucose and 20 mM 2'-Deoxycytidine).

Results

PR-104A and SN33540 were determined to be 20-fold and 25-fold more cytotoxic to HCT116 cells under anoxia, respectively (Hypoxic Cytotoxicity Ratios [HCRs]=20 and 25, respectively), whereas preferred AKR1C3-activated prodrugs 602 and 641 were either equitoxic under anoxic conditions or demonstrated a modest HCR of 2 (Table 5).

TABLE 5

Anti-proliferative IC50 (µM) of compounds of the invention in wild-type HCT116 colon cancer cells under oxic and anoxic conditions.

| | HCT116-WT Anti-proliferative IC50 (µM) | | |
|---|---|---|---|
| Compound | Oxic | Anoxic | Hypoxic Cytotoxicity Ratio (HCR) |
| PR-104A | 55.8 | 2.83 | 20 |
| SN33540 | 127.3 | 5.10 | 25 |
| 602 | 4.26 | 3.51 | 1 |
| 641 | 5.91 | 2.52 | 2 |

Example 13: Formulation of Prodrugs

The solubility and stability of compound 641 was studied by HPLC in lactate buffer (pH 4) and water as the free base and the mesylate salt (641.Ms) at 0° C. and room temperature (RT). The free base had acceptable solubility (3.4 mmol/L) as a free base in lactate buffer. However, this was improved considerably by formulation as the mesylate salt, producing a solubility of greater than 100 mmol/L in lactate buffer and greater than 70 mmol/L in water. The free base and the mesylate salt had comparable stability in solution in lactate buffer at room temperature with a half-life of approximately 24 hours. This stability was improved considerably by reducing the temperature of the solution to 0° C.

TABLE 6

Solubility and stability of compound 641 as a free base and a
mesylate salt in water and lactate buffer (pH 4) at 0° C. and room temperature (RT).

| Chemical Structure | Form | Compound | Solubility (mmol/L) | | Stability (% Parent after 24 hours) | | | |
|---|---|---|---|---|---|---|---|---|
| | | | Water RT | Lactate Buffer RT | Water 0° C. | Water RT | Lactate Buffer 0° C. | Lactate Buffer RT |
| [structure with NO$_2$, piperazine sulfonyl, N(CH$_2$CH$_2$OSO$_2$CH$_3$)$_2$] | Free Base | 641 | | 3.4 | | | | 54.4 |
| | Mesylate Salt | 641.Ms | >71 | >104 | | 53.8 | 91.7 | 51.9 |

Example 14: In Vivo Efficacy in Xenograft Models that Express Human AKR1C3

Materials and Methods
Animal Husbandry

Specific pathogen-free female homozygous nude NIH-III (NIH-Lyst$^{bg}$ Foxn1$^{nu}$ Btk$^{xid}$) mice were bred by the Vernon Jansen Unit (shared vivarium, University of Auckland). Animals were housed in Techniplast microisolator cages and provided with a standard twelve hour day-night light schedule. Animals received standard rodent diet (Harlan Teklad diet 2018i) and water ad libitum. All animal studies were approved by the University of Auckland Animal Ethics Committee.

Tumour Cell Inoculation

Animals weighed 18-25 g at the time of tumour inoculation. Tumours were grown subcutaneously on the right flank of mice by inoculating cells grown in tissue culture (1×10$^7$ cells in 100 uL serum free α-MEM). Tumour sizes were monitored three times weekly using electronic callipers and treatments were initiated once tumour diameter reached ≥7 mm.

Growth Delay

Tumour bearing mice were randomised into the appropriate treatment groups and tumour size and body weight recorded. Test compounds were formulated on the day of the experiment and kept in foil-wrapped tubes out of direct fluorescent light. If recruitment of animals occurred over multiple days, the drug stocks were aliquoted into tubes and frozen once at −80° C. until required. Mice were treated with a single (or q4dx3 or q4dx4 or q4dx6) dose of a compound of the invention by intraperitoneal injection and thereafter tumour size and body weight was monitored every second day. Tumour volume was calculated as n (l×w×w)/6, where l is the major axis and w is the perpendicular minor axis. Animals were culled when they had reached the appropriate survival endpoint or when body weight loss exceeded 20% of the pre-treatment value.

Results

Results of the in vivo efficacy testing of SN34454 and compounds 602, 641 and 641.Ms in H460, PLC/PRF/5, SW780, SNU-398$^{WT}$ (wild type) and SNU-398$^{AKR1C3}$ tumour xenografts in female NIH-III mice are shown in FIGS. 2 to 7.

Figure 2:
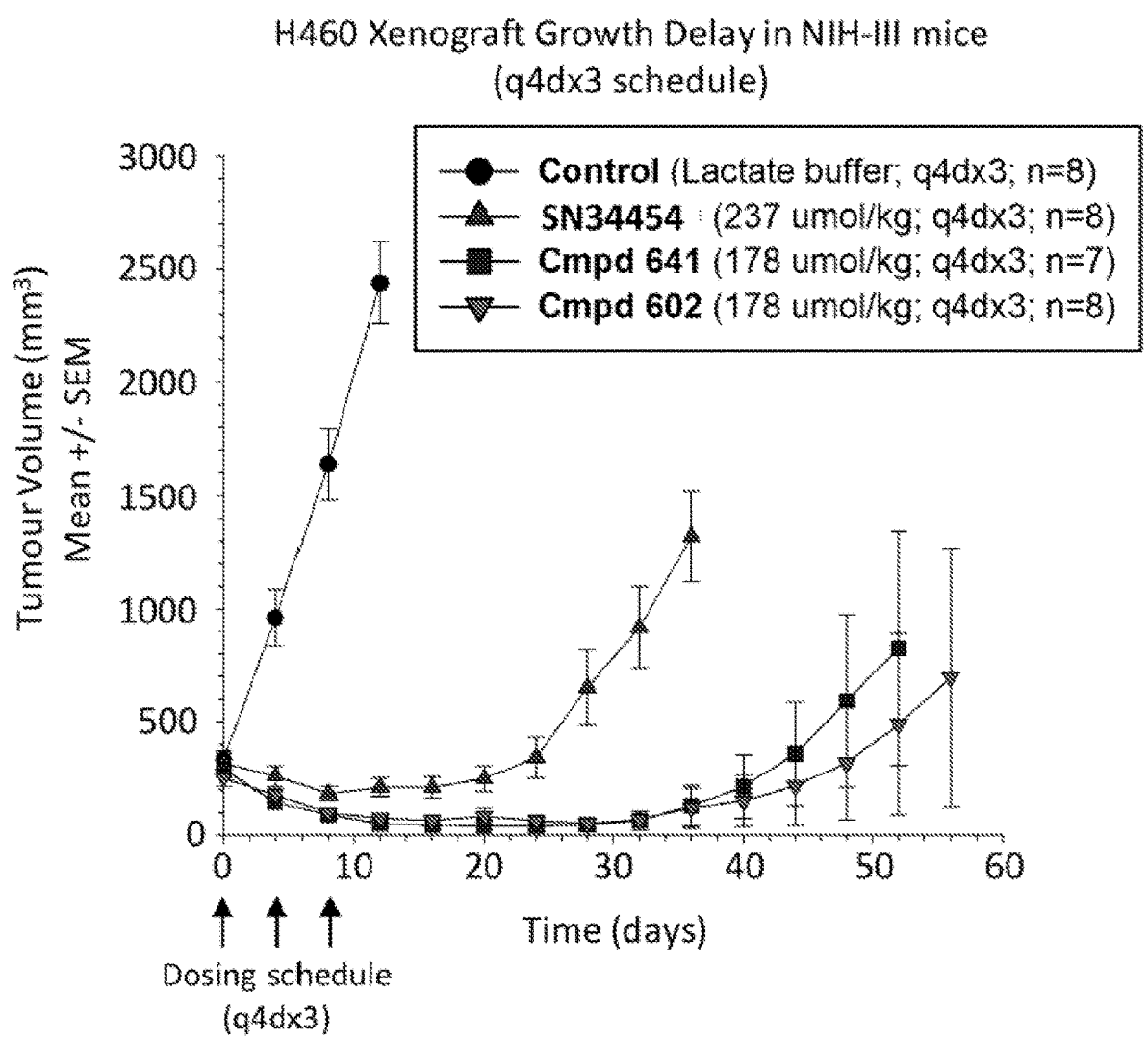
FIG. 2 shows the mean tumour volume (mm$^3$) of H460 lung cancer xenografts in NIH-III mice administered a well-tolerated 3-dose schedule (q4dx3) of the prior art prodrug SN34454, compared to compounds 602 and 641 at doses of 237, 178 and 178 µmol/kg, respectively (intraperitoneal). All of the compounds display anti-tumour efficacy. Compounds 602 and 641 are significantly more active than the prior art compound SN34454, despite being administered at 75% of the respective dose.

NIH-III mice bearing H460 lung cancer xenografts were administered a well-tolerated 3-dose schedule (q4dx3) of SN34454, compared to compounds 602 and 641 at doses of 237, 178 and 178 μmol/kg, respectively (intraperitoneal). All of the compounds displayed anti-tumour efficacy (FIG. 2). Compounds 602 and 641 were significantly more active than SN34454, despite being administered at 75% of the respective dose. The improved efficacy of sulfonamide compound 602 relative to the direct comparator carboxamide SN34454, despite the use of a significantly lower administered dose, was surprising.

Figure 3:
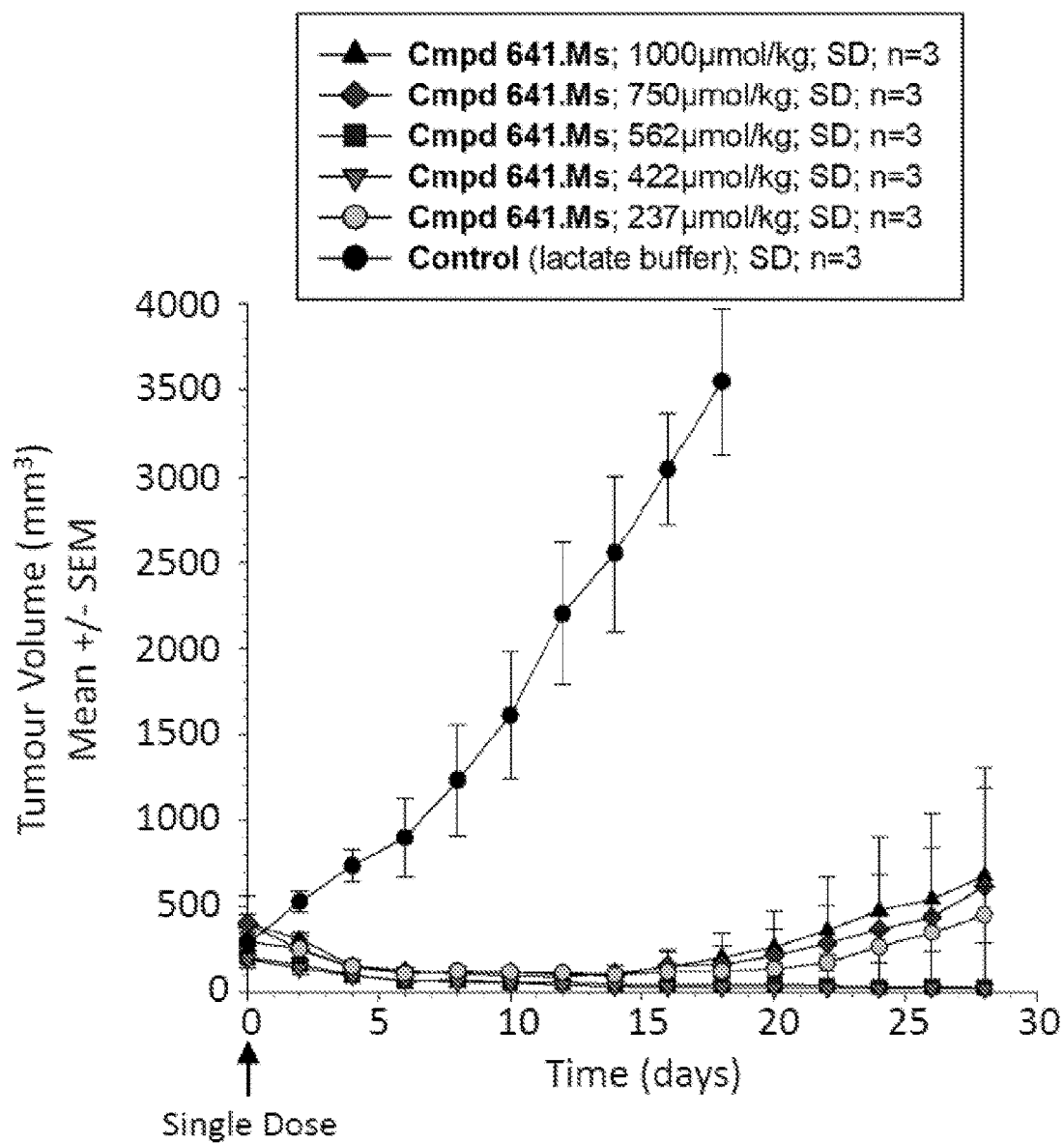
FIG. 3 shows the mean tumour volume (mm$^3$) of H460 lung cancer xenografts in NIH-III mice administered a single dose of compound 641.Ms (intraperitoneal). Doses used were 237, 422, 562, 750 and 1000 µmol/kg. All doses of compound 641.Ms displayed significant anti-tumour efficacy.

NIH-III mice bearing H460 lung cancer xenografts were administered a single dose of compound 641.Ms (intraperitoneal). Doses used were 237, 422, 562, 750 and 1000 μmol/kg. All doses of the compound were well-tolerated and displayed significant anti-tumour efficacy (FIG. 3).

Figure 4:
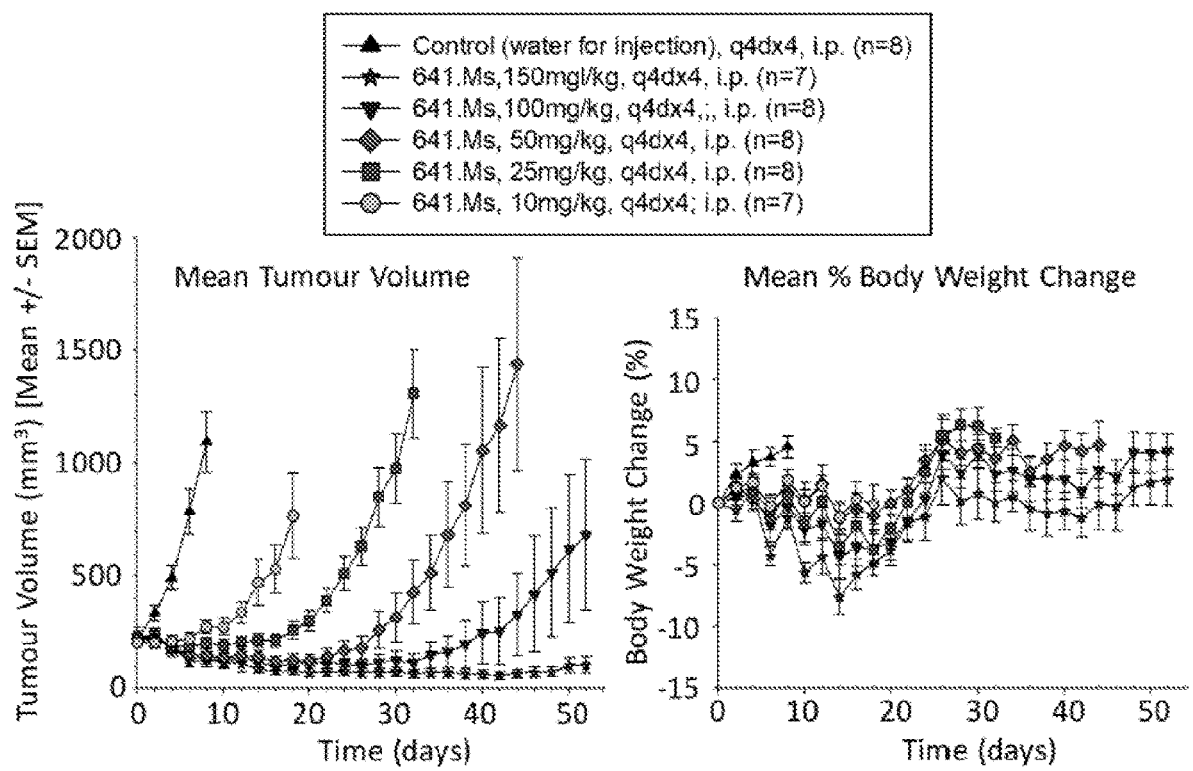
FIG. 4 shows the mean tumour volume (mm$^3$) of H460 lung cancer xenografts in NIH-III mice administered a 4-dose schedule (q4dx4) of compound 641.Ms (intraperitoneal). Doses used were 10, 25, 50, 100 and 150 mg/kg. All doses of compound 641.Ms displayed significant anti-tumour efficacy and were well tolerated as determined by mean percentage change in body weight with no dose cohort exceeding −10%.

NIH-III mice bearing H460 lung cancer xenografts were administered a 4-dose schedule (q4dx4) of compound 641.Ms (intraperitoneal). Doses used were 10, 25, 50, 100 and 150 mg/kg. All doses of the compound displayed significant anti-tumour efficacy and were well-tolerated as determined by mean percentage change in body weight with no dose cohort exceeding −10% (FIG. 4).

Figure 5:
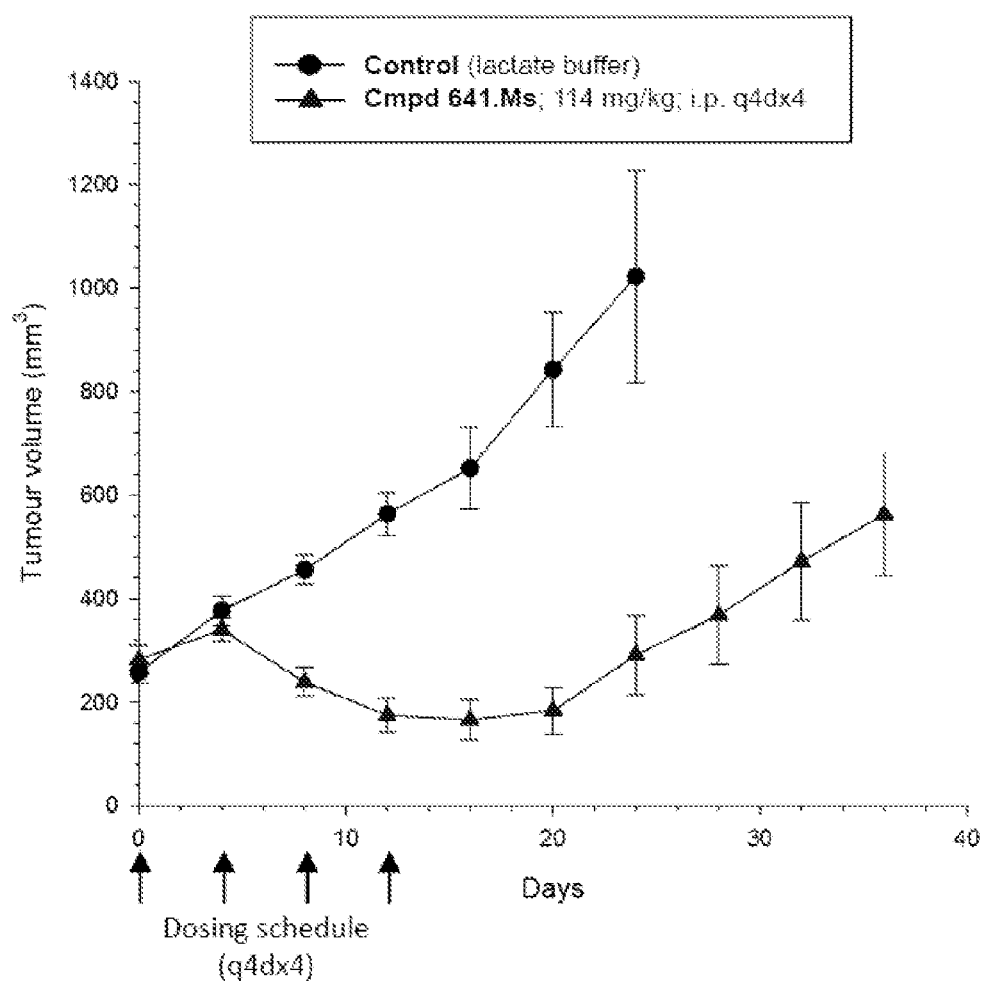
FIG. 5 shows the mean tumour volume (mm3) of PLC/PRF/5 hepatocellular carcinoma xenografts in NIH-III mice administered a well-tolerated 4-dose schedule (q4dx4) of compound 641.Ms at a dose of 114 mg/kg (intraperitoneal). Compound 641.Ms showed significant anti-tumour activity.

NIH-III mice bearing PLC/PRF/5 hepatocellular carcinoma xenografts were administered a well-tolerated 4-dose schedule (q4dx4) of compound 641.Ms at a dose of 114 mg/kg (intraperitoneal). Compound 641.Ms showed significant anti-tumour activity (FIG. 5).

Figure 6:
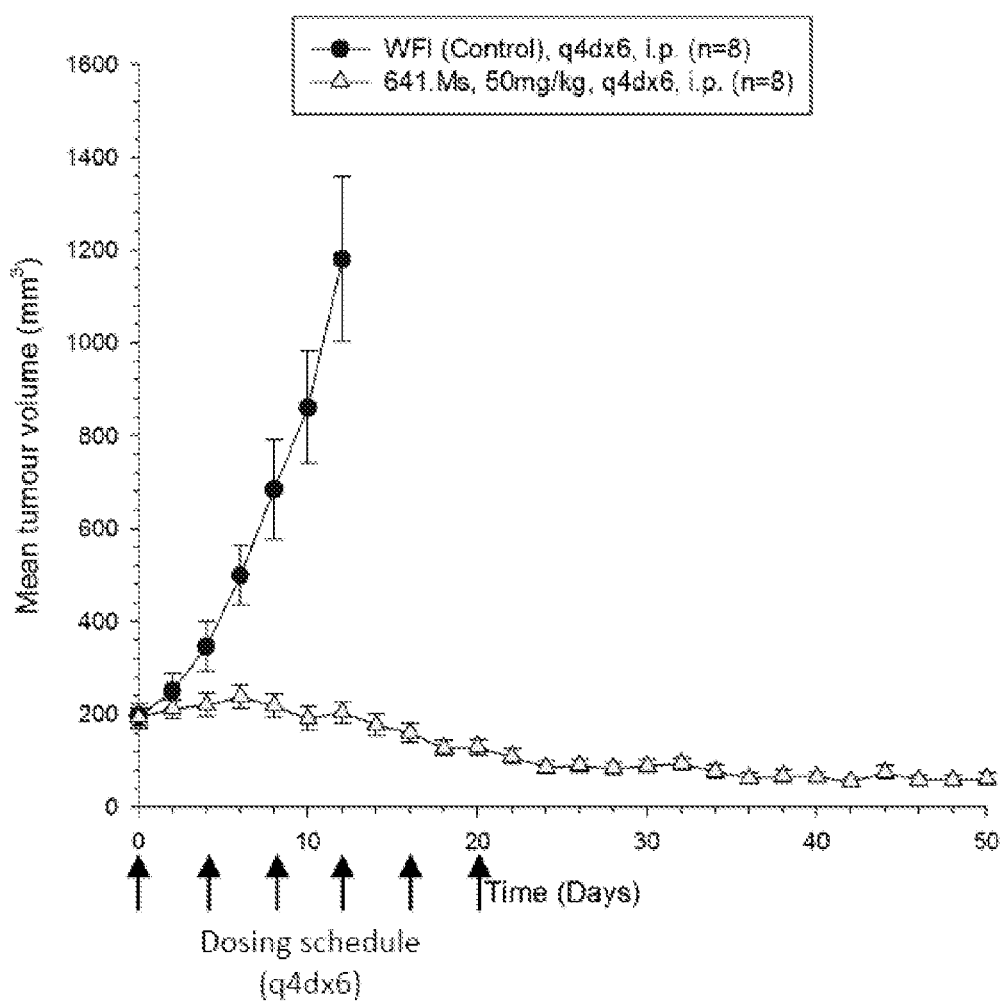
FIG. 6 shows the mean tumour volume (mm3) of SW780 bladder carcinoma xenografts in NIH-III mice administered a well-tolerated 6-dose schedule (q4dx6) of compound 641.Ms at a dose of 50 mg/kg (intraperitoneal). Compound 641.Ms showed significant anti-tumour activity.

NIH-III mice bearing SW780 bladder carcinoma xenografts were administered a well-tolerated 6-dose schedule (q4dx6) of compound 641.Ms at a dose of 50 mg/kg (intraperitoneal). Compound 641.Ms showed significant anti-tumour activity (FIG. 6).

Figure 7:
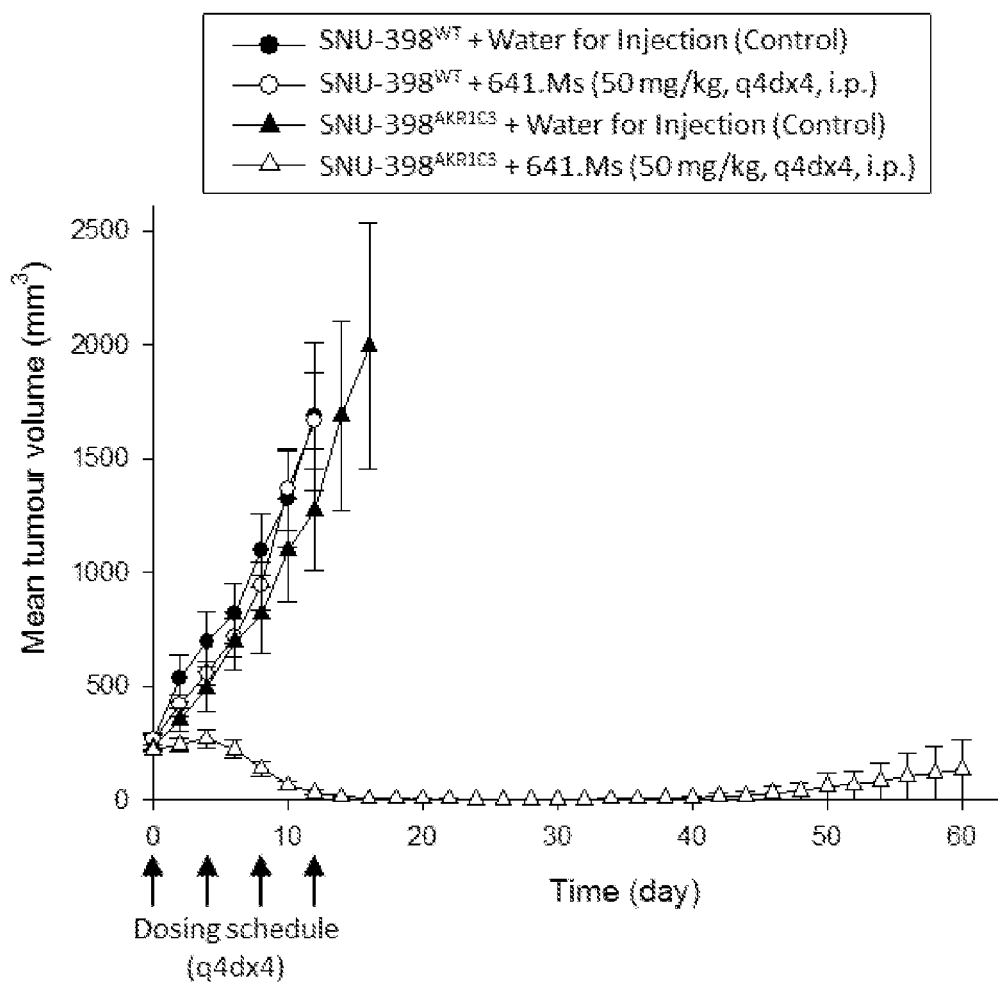
FIG. 7 shows the mean tumour volume (mm3) of SNU-398$^{WT}$ (wild type) and SNU-398$^{AKR1C3}$ (AKR1C3 overexpressing) isogenic hepatocellular carcinoma xenografts in NIH-III mice administered a well-tolerated 4-dose schedule (q4dx4) of compound 641.Ms at a dose of 50 mg/kg (intraperitoneal). Compound 641.Ms only showed significant anti-tumour activity in the SNU-398$^{AKR1C3}$ xenograft model engineered to over-express AKR1C3. Compound 641.Ms was inactive in the SNU-398$^{WT}$ xenograft model known to have negligible expression of AKR1C3.

NIH-III mice bearing either SNU-398$^{WT}$ (wild type) or SNU-398$^{AKR1C3}$ (AKR1C3 over-expressing) isogenic hepatocellular carcinoma xenografts were administered a well-tolerated 4-dose schedule (q4dx4) of compound 641.Ms at a dose of 50 mg/kg (intraperitoneal). Compound 641.Ms only showed significant anti-tumour activity in the SNU-398$^{AKR1C3}$ xenograft model engineered to over-express AKR1C3. Compound 641.Ms was inactive in the SNU-398*T xenograft model known to have negligible expression of AKR1C3 (FIG. 7).

In summary, all compounds of the invention tested provided a profound tumour growth delay following a single, q4dx3, q4dx4 or q4dx6 intraperitoneal dosing schedule in xenograft models known to express AKR1C3. Notably, compound 641.Ms was inactive in SNU-398 wild type xenografts. Collectively, the data indicates that prodrug metabolism by AKR1C3 expressed in xenograft models leads to the production of cytotoxic metabolites, resulting in anti-tumour activity.

Example 15: Determination of Bystander Cell Killing

Compounds which displayed a high efficacy against AKR1C3 over-expressing cells in the low cell density antiproliferative assay were also be evaluated for efficacy against AKR1C3 over-expressing cells in a high cell density multicellular layer (MCL) assay. The MCL model utilised for this evaluation consisted of AKR1C3 overexpressing (activator) cells or non-AKR1C3 expressing (target) cells or a mixture of these two cell types grown in a ratio of 5:95. The mixture of the two distinct cell populations enabled the determination of the extent of the transfer of cytotoxic metabolites from the activator cell to the target cell population.

Plating efficiencies were calculated as the fraction of colonies formed relative to the number of cells seeded. The compound concentrations for 10% survival ($C_{10}$) of target cells grown without activators (T), targets in co-culture ($T_c$) and activators in co-culture ($A_c$) was determined by interpolation. Bystander effect efficiency (BEE) was calculated as (Log $C_{10}$T–Log $C_{10}T_c$)/(Log $C_{10}$T–Log $C_{10}A_c$), where BEE is the measure of cytotoxic metabolite transfer. In contrast to PR-104A, preferred compounds of the invention have a minimal BEE, reducing off-target side effects from ablation of neighbouring non-AKR1C3 expressing cells.

Materials and Methods
Preparation of MCLs

Millicell-CM membrane inserts were coated in calf-skin collagen type III. The collagen solution was prepared dissolving in sterile 0.01 N HCl to a concentration of 3 mg/mL. The collagen solution was diluted (1:5) in sterile 60% ethanol and 100 µL of this solution was used to coat the membrane inserts and left overnight in a sterile environment to dry.

Prior to adding cells, the inserts were sterilised in 70% ethanol and left to aerate in a sterile environment in order for the ethanol to evaporate. A sterile polyethylene foam ring was placed around each insert to enable subsequent floatation. Single cell suspensions of $1 \times 10^6$ cells in a volume of 500 µL was added to each insert. When mixtures of cells were required, $1 \times 10^6$ cells of the mixed cell suspension (in 500 µL) were added to each insert. The type of mixed MCLs used in experiments consisted of 95% HCT116$^{NeoR}$ and 5% HCT116$^{AKR1C3}$ cells. The HCT116$^{NeoR}$ ells were used in this mixture as an AKR1C3 negative cell line which can subsequently be grown in selective medium containing Geneticin (G418), and which enabled discrimination with the AKR1C3 positive cell line (which can be grown in selective medium containing puromycin). The inserts containing cells were placed in a sterile screw-top plastic jar containing 300 mL of α-MEM+10% v/v FBS+1% PSG, with a maximum of 6 inserts in a jar. The inserts were left floating in the medium for 4 hours in a humidified incubator (37° C., 5% $CO_2$) to enable cells to adhere to the collagen coat and then submerged in the medium with a sterile stainless steel grid. Cells were left to grow and form MCLs on the inserts for a period of 3 days by placing the jars in a 37° C. water bath with continuous magnetic stirring of the medium.

MCL Experimental Procedure

Three days after growth of cells as MCLs in inserts, each insert was inspected with an inverted phase contrast microscope to ensure uniform growth of cells. Suitable MCLs were transferred to 25 mL glass vessels containing 10 mL of medium (α-MEM+10% v/v FBS+1% PSG) with the required drug concentrations. Each insert in the glass vessel was held by a stainless steel loop attached to the lid. The vessels were placed in a 37° C. water bath. Ports on the lid of each bottle enabled gassing with the required gas phase. The glass vessels containing the MCL inserts and drug were left in the 37° C. water bath for 5 hours with continuous gassing and magnetic stirring of medium. The gas phase used was 5% $CO_2$:95% $O_2$, with the high oxygen concentration used to minimise bioreductive drug activation by endogenous one-electron reductases.

After the 5 hour incubation, each insert was trypsinised in 0.07% trypsin in PBS for 10 minutes at 37° C. to dissociate the MCL into a single cell suspension. The dissociated cells were incubated for a further 10 minutes in α-MEM containing 10% FBS and 100 µg/ml DNAase I. Cells were then counted on a Z2 Coulter® Particle Count and Size Analyzer and resuspended in fresh medium. The cells were serially diluted and plated in P60 dishes at between $10^2$ and $10^5$ cells/dish to determine clonogenic survival. To discriminate clonogenic activators (HCT116$^{AKR1C3}$) from targets (HCT116$^{NeoR}$), ells from mixed MCLs were plated in two types of selective media; medium containing 1 µM puromycin (which enables growth of the activator colonies) and medium containing 500 µg/mL of Geneticin (which enables growth of target colonies). Cells from MCLs containing 100% target cells were left to grow in medium containing Geneticin (500 µg/mL). Colonies were left to grow in a 37° C., 5% $CO_2$ incubator for 10 days prior to staining with methylene blue (2 g/L in 50% v/v aqueous ethanol). Colonies containing more than 50 cells were counted as clonogenic survivors. Plating efficiencies were calculated as the fraction of colonies formed relative to the number of cells seeded. The drug concentrations for 10% survival ($C_{10}$) of target cells grown without activators (T), targets in co-culture ($T_c$) and activators in co-culture ($A_c$) were determined by interpolation. Bystander effect efficiency (BEE) was calculated as (Log $C_{10}$T–Log $C_{10}T_c$)/(Log $C_{10}$T–Log $C_{10}A_c$).

Results

Figure 8:
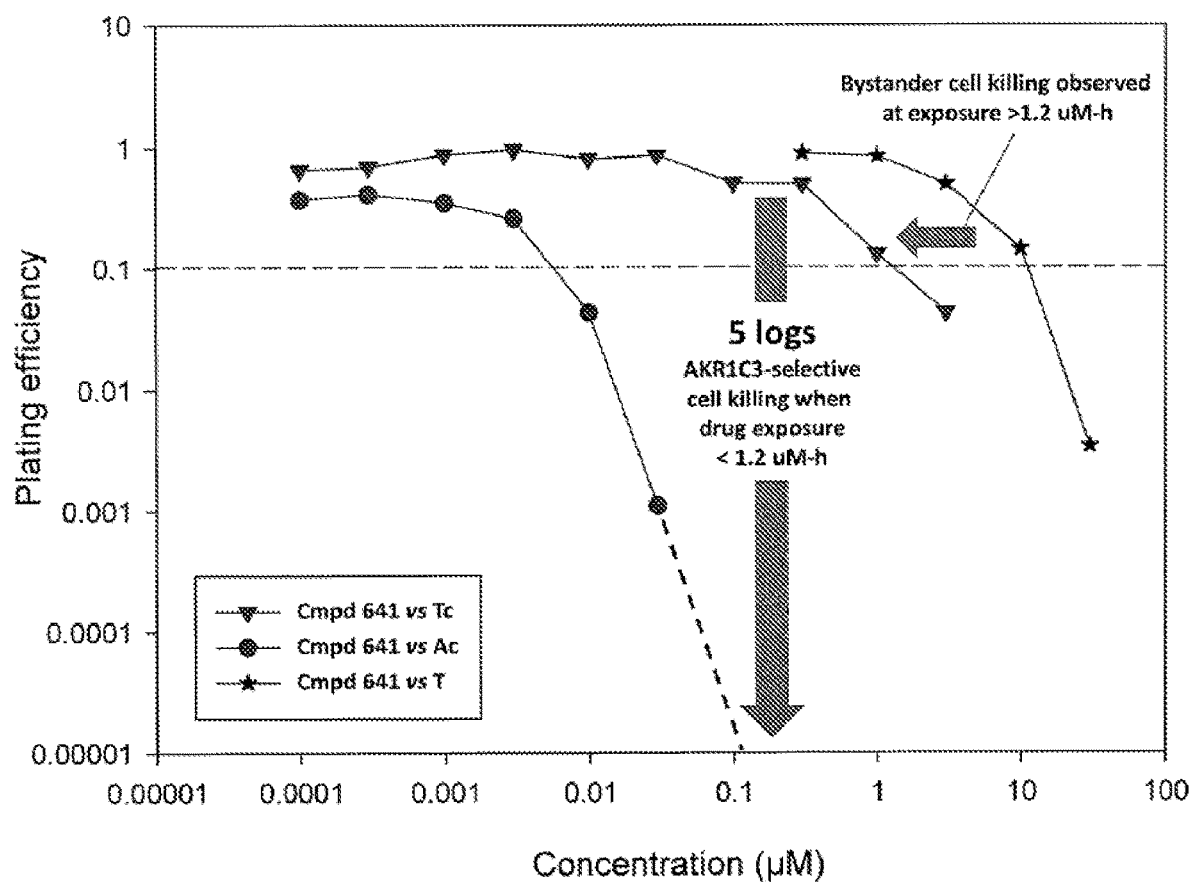
FIG. 8 shows the results of a high cell density multicellular layer (MCL) assay for compound 641 in mixed HCT116 colon cancer MCLs containing 5% AKR1C3 overexpressing cells to determine bystander effect efficiency. Compound 641 demonstrates a modest bystander effect at exposures above 1.2 µM·h and no bystander effect at exposures <1.2 µM·h, providing 5 logarithms of clonogenic cell killing of AKR1C3-positive cells selectively in a mixed 3D cell culture.

The results of a high cell density multicellular layer (MCL) assay for compound 641 in mixed HCT116 colon cancer MCLs containing 5% AKR1C3 over-expressing cells is shown in FIG. 8. Compound 641 demonstrated a target cell $C_{10}$ of 11.1 µM (T), a targets in co-culture $C_{10}$ of 1.27 µM ($T_c$) and an activators in co-culture $C_{10}$ of 0.0054 µM ($A_c$). Together this data indicates that AKR1C3 expressing cells are 2055-fold more sensitive to clonogenic cell kill by compound 641 than AKR1C3-negative cells when grown at high cell density (T/Ac) and that a 5% population of AKR1C3-positive cells in multicellular layer exerts only a modest degree of cell killing on the AKR1C3-negative cell population by cytotoxic metabolite transfer (bystander effect), with only a 9-fold shift in the $C_{10}$ from 11.1 µM (T) to 1.27 µM (Tc). It will be apparent from FIG. 8 that at least 99.9% of the AKR1C3-positive HCT116 cells are clonogenically sterilised at concentrations of compound 641 ranging from 0.002 µM to 0.2 µM. This occurs in the absence of concurrent clonogenic cell kill in wild type AKR1C3-negative HCT116 despite these cells being exposed to compound 641 while in a multicellular tissue-like environment that ensures intimate contact with the AKR1C3-positive HCT116 cells.

At compound exposures <1.2 uM·hr (0.2 μM for 5 hours), compound 641 results in up to 5 logarithms of clonogenic cell killing of AKR1C3-positive cells while not effecting the clonogenic survival of AKR1C3-negative cells, despite their being intimately mixed in a high cell density (3D) multicellular layer. At exposures >1.2 uM·hr (0.2 μM for 5 hours) compound 641 demonstrated a minimal bystander effect efficiency (BEE) of 28%. This result was surprising when compared to literature reports that PR-104A (also known as SN27858) has a substantial bystander effect (Foehrenbacher et al, Frontiers in Oncology, 2013, 3, 263) and that compounds SN27686, SN33539, SN33540 and SN34118 have been reported to have BEE's of 57.6%, 82.1%, 60%, and 52.7%, respectively in AKR1C3 mixed MCLs (Silva, S., University of Auckland Library, MSc Thesis, 2013).

CONCLUSIONS

Collectively, the data indicate that the AKR1C3-activated prodrugs of the invention are improved substrates for AKR1C3 compared to the known compounds as exemplified by PR-104A, by virtue of structural modifications that result in increased affinity for the AKR1C3 enzyme (lower $K_m$) and improved catalytic efficiency by AKR1C3 (increased $k_{cat}/K_m$). The data further indicates preferred examples of the invention are improved AKR1C3-activated prodrugs compared to known compounds, as exemplified by SN33539, SN35028, SN34947, SN34951, SN34118 and SN34454, because they achieve an optimal balance of affinity for the AKR1C3 catalytic site and substrate turnover, such that they do not inhibit AKR1C3 metabolism at high concentrations.

Prodrugs of the invention are metabolised by AKR1C3 and demonstrate increased clonogenic cell kill in multicellular layers of cells engineered to over-express AKR1C3 relative to multicellular layers of wild type isogenic cells.

The AKR1C3-activated prodrugs of the invention are significantly more cytotoxic than the prior art in wild-type cell lines (HCT116, SNU398) that have been engineered to over-express human AKR1C3. This cytotoxicity can be ameliorated by the inhibition of AKR1C3 with a known potent and selective AKR1C3 inhibitor, directly implicating AKR1C3 expression and prodrug metabolism in the observed cytotoxicity.

The AKR1C3-activated prodrugs of the invention are significantly more cytotoxic than the prior art in wild-type cell lines (H460, PLC/PRF/5) that endogenously express human AKR1C3. This cytotoxicity can be ameliorated by the inhibition of AKR1C3 with a known potent and selective AKR1C3 inhibitor, directly implicating AKR1C3 expression and prodrug metabolism in the observed cytotoxicity.

The AKR1C3-activated prodrugs of the invention demonstrate significant improved anti-tumour efficacy in H460 lung cancer xenograft-bearing NIH-III mice compared to known compounds as exemplified by SN34454. The prodrugs of the invention further demonstrate significant anti-tumour activity in PLC/PRF/5, SW780, and SNU-398$^{AKR1C3}$ tumour xenografts in female NIH-III mice at well-tolerated doses and schedules. The AKR1C3-dependence of this anti-tumour efficacy has been confirmed by the lack of activity in AKR1C3-negative SNU-398$^{WT}$ (wild type) tumour xenografts in female NIH-III mice.

Reference to any prior art in this specification is not, and should not be taken as, an acknowledgment or any suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Wherein the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the scope of the invention and without diminishing its attendant advantages. It is therefore intended that such changes and modifications be included within the scope of the invention.

The invention claimed is:
1. A compound of Formula (I):

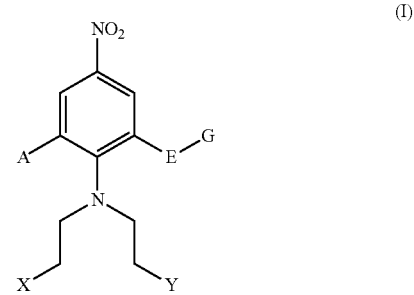

wherein:
A is H, C1-C6 alkyl, C2-C6 alkenyl, C2-C6 alkynyl, $CFH_2$, $CF_2H$, $CF_3$, F, Cl, Br, I, $OCF_3$, COR, or $CON(R)_2$;
E is SO, or $SO_2$;
X is Cl, Br, I, or $OSO_2R$;
Y is Cl, Br, I, or $OSO_2R$;
each R is independently H or C1-C6 alkyl;
G is a radical selected from the group comprising Formulae (B)-(AA):

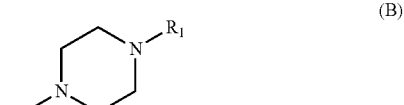

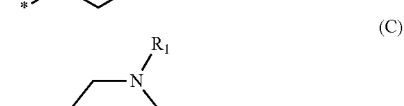

-continued (F) 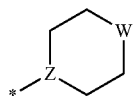

(H) 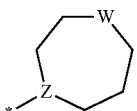

(J) 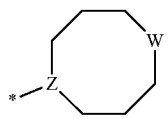

(K) 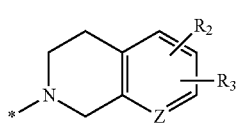

(L) 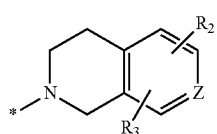

(M) 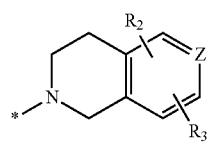

(N) 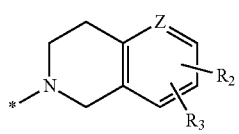

(O) 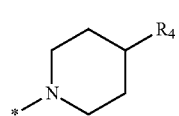

(P) 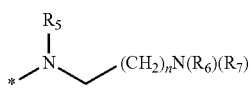

(Q) 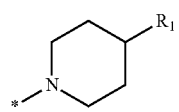

(S) 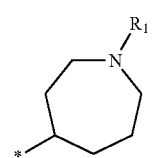

(T) 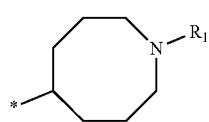

-continued (U) 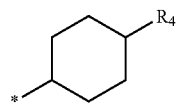

(AA) 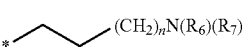

wherein:
R$_1$ is H, C1-C6 alkyl, CH$_2$(CH$_2$)$_n$OH, CH$_2$CH(OH) CH$_2$OH, phenyl, pyridinyl, benzyl, or pyridinylmethyl, provided that when R$_1$ is phenyl, pyridinyl, benzyl or pyridinylmethyl, R$_1$ is optionally substituted in any available position with C1-C6 alkyl, C2-C6 alkenyl, C2-C6 alkynyl, OR$_6$, N(R$_6$)(R$_7$), CFH$_2$, CF$_2$H, CF$_3$, F, Cl, Br, I, OCF$_3$, COR$_6$, CON(R$_6$)(R$_7$), SOR$_6$, SON(R$_6$)(R$_7$), SO$_2$R$_6$, SO$_2$N(R$_6$)(R$_7$), CN, or NO$_2$;

R$_2$ and R$_3$ are each independently H, C1-C6 alkyl, C2-C6 alkenyl, C2-C6 alkynyl, OR$_6$, N(R$_6$)(R$_7$), CFH$_2$, CF$_2$H, CF$_3$, F, Cl, Br, I, OCF$_3$, COR$_6$, CON(R$_6$)(R$_7$), SOR$_6$, SON(R$_6$)(R$_7$), SO$_2$R$_6$, SO$_2$N(R$_6$)(R$_7$), CN, or NO$_2$;

R$_4$ is N(R$_6$)(R$_7$), OH, OCH$_2$(CH$_2$)$_n$N(R$_6$)(R$_7$), or CH$_2$(CH$_2$)$_n$N(R$_6$)(R$_7$);

R$_5$ is H, or C1-C6 alkyl group;

R$_6$ and R$_7$ are each independently H, or C1-6 alkyl, or R$_6$ and R$_7$ taken together form a substituted or unsubstituted 5- or 6-membered heterocyclic ring;

Z is CH or N;

W is CH$_2$, O, S, SO, or SO$_2$;

n is 0 to 6;

* represents a point of attachment to Formula (I);

or a pharmaceutically acceptable salt thereof.

2. A compound as claimed in claim 1, wherein:
A is H, C1-C6 alkyl, C2-C6 alkenyl, C2-C6 alkynyl, CFH$_2$, CF$_2$H, CF$_3$, or OCF$_3$;
E is SO, or SO$_2$;
X is Br, or OSO$_2$R;
Y is Br, or OSO$_2$R;
each R is independently H or C1-C6 alkyl;
G is a radical selected from the group comprising Formulae (B), (C), (D), (O) and (P):

(B) 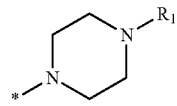

(C) 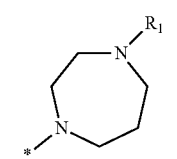

(D) 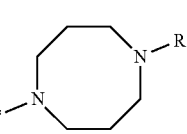

(O) 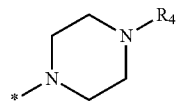

-continued

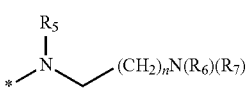
(P)

wherein
R₁ is H, C1-C6 alkyl, $CH_2(CH_2)_nOH$, $CH_2CH(OH)CH_2OH$;
R₄ is $N(R_6)(R_7)$, $OCH_2(CH_2)_nN(R_6)(R_7)$, or $CH_2(CH_2)_nN(R_6)(R_7)$;
R₅ is H, or C1-C6 alkyl;
R₆ and R₇ are each independently H, or C1-6 alkyl, or R₆ and R₇ taken together form a substituted or unsubstituted 5- or 6-membered heterocyclic ring;
n is 0 to 6;
* represents a point of attachment to Formula I;
or a pharmaceutically acceptable salt thereof.

3. A compound as claimed in claim 1, wherein:
A is H, C2-C6 alkynyl, $CFH_2$, $CF_2H$, or $CF_3$;
E is $SO_2$;
X is Br, or $OSO_2R$;
Y is Br, or $OSO_2R$;
each R is independently H or C1-C6 alkyl;
G is a radical selected from the group comprising Formulae (B), (C), (D), (O) and (P):

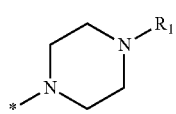
(B)

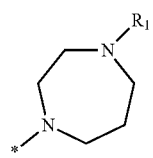
(C)

(D)

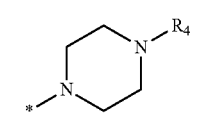
(O)

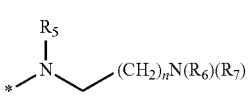
(P)

wherein
R₁ is H, C1-C6 alkyl, $CH_2(CH_2)_nOH$, $CH_2CH(OH)CH_2OH$;
R₄ is $N(R_6)(R_7)$, $OCH_2(CH_2)_nN(R_6)(R_7)$, or $CH_2(CH_2)_nN(R_6)(R_7)$;
R₅ is H, or C1-C6 alkyl;
R₆ and R₇ are each independently H, or C1-6 alkyl, or R₆ and R₇ taken together form a substituted or unsubstituted 5- or 6-membered heterocyclic ring;
n represents 0 to 6;
* represents a point of attachment to Formula I;
or a pharmaceutically acceptable salt thereof.

4. A compound as claimed in claim 1, wherein A is H.

5. A compound as claimed in claim 1 which is selected from the group comprising:
N,N-bis(2-bromoethyl)-4-nitro-2-(piperazin-1-ylsulfonyl)aniline (562);
N,N-bis(2-bromoethyl)-2-((4-methylpiperazin-1-yl)sulfonyl)-4-nitroaniline (563);
N,N-bis(2-bromoethyl)-2-((4-ethylpiperazin-1-yl)sulfonyl)-4-nitroaniline (564);
2-(4-((2-(bis(2-bromoethyl)amino)-5-nitrophenyl)sulfonyl)piperazin-1-yl)ethanol (565);
3-(4-((2-(bis(2-bromoethyl)amino)-5-nitrophenyl)sulfonyl)piperazin-1-yl)propane-1,2-diol (566);
N,N-bis(2-bromoethyl)-2-((4-methyl-1,4-diazepan-1-yl)sulfonyl)-4-nitroaniline (584);
N,N-bis(2-bromoethyl)-2-((5-methyl-1,5-diazocan-1-yl)sulfonyl)-4-nitroaniline (585);
N,N-bis(2-bromoethyl)-2-((1-methylpiperidin-4-yl)sulfonyl)-4-nitroaniline (586);
1-((2-(bis(2-bromoethyl)amino)-5-nitrophenyl)sulfonyl)piperidin-4-amine (587);
1-((2-(bis(2-bromoethyl)amino)-5-nitrophenyl)sulfonyl)-N,N-dimethylpiperidin-4-amine (588);
N,N-bis(2-bromoethyl)-2-((1-methylazepan-4-yl)sulfonyl)-4-nitroaniline (589);
N,N-bis(2-bromoethyl)-2-((1-methylazocan-5-yl)sulfonyl)-4-nitroaniline (590);
N,N-bis(2-bromoethyl)-2-(morpholinosulfonyl)-4-nitroaniline (591);
2-(bis(2-bromoethyl)amino)-N-(2-(dimethylamino)ethyl)-5-nitrobenzenesulfonamide (592);
2-(bis(2-bromoethyl)amino)-N-(2-(dimethylamino)ethyl)-N-methyl-5-nitrobenzenesulfonamide (593);
2-(bis(2-bromoethyl)amino)-N-(2-morpholinoethyl)-5-nitrobenzenesulfonamide (594);
2-(bis(2-bromoethyl)amino)-N-methyl-N-(2-morpholinoethyl)-5-nitrobenzenesulfonamide (595);
2-((2-bromoethyl)(4-nitro-2-(piperazin-1-ylsulfonyl)phenyl)amino)ethyl methanesulfonate (601);
2-((2-bromoethyl)(2-((4-methylpiperazin-1-yl)sulfonyl)-4-nitrophenyl)amino)ethyl methanesulfonate (602);
2-((2-bromoethyl)(2-((4-ethylpiperazin-1-yl)sulfonyl)-4-nitrophenyl)amino)ethyl methanesulfonate (603);
2-((2-bromoethyl)(2-((4-(2-hydroxyethyl)piperazin-1-yl)sulfonyl)-4-nitrophenyl)amino)ethyl methanesulfonate (604);
2-((2-bromoethyl)(2-((4-(2,3-dihydroxypropyl)piperazin-1-yl)sulfonyl)-4-nitrophenyl)amino)ethyl methanesulfonate (605);
2-((2-bromoethyl)(2-((4-methyl-1,4-diazepan-1-yl)sulfonyl)-4-nitrophenyl)amino)ethyl methanesulfonate (623);
2-((2-bromoethyl)(2-((5-methyl-1,5-diazocan-1-yl)sulfonyl)-4-nitrophenyl)amino)ethyl methanesulfonate (624);
2-((2-bromoethyl)(2-((1-methylpiperidin-4-yl)sulfonyl)-4-nitrophenyl)amino)ethyl methanesulfonate (625);
2-((2-((4-aminopiperidin-1-yl)sulfonyl)-4-nitrophenyl)(2-bromoethyl)amino)ethyl methanesulfonate (626);
2-((2-bromoethyl)(2-((4-(dimethylamino)piperidin-1-yl)sulfonyl)-4-nitrophenyl)amino)ethyl methanesulfonate (627);
2-((2-bromoethyl)(2-((1-methylazepan-4-yl)sulfonyl)-4-nitrophenyl)amino)ethyl methanesulfonate (628);
2-((2-bromoethyl)(2-((1-methylazocan-5-yl)sulfonyl)-4-nitrophenyl)amino)ethyl methanesulfonate (629);
2-((2-bromoethyl)(2-(morpholinosulfonyl)-4-nitrophenyl)amino)ethyl methanesulfonate (630);

2-((2-bromoethyl)(2-(N-(2-(dimethylamino)ethyl)sulfamoyl)-4-nitrophenyl)amino)ethyl methanesulfonate (631);

2-((2-bromoethyl)(2-(N-(2-(dimethylamino)ethyl)-N-methylsulfamoyl)-4-nitrophenyl)amino)ethyl methanesulfonate (632);

2-((2-bromoethyl)(2-(N-(2-morpholinoethyl)sulfamoyl)-4-nitrophenyl)amino)ethyl methanesulfonate (633);

2-((2-bromoethyl)(2-(N-methyl-N-(2-morpholinoethyl)sulfamoyl)-4-nitrophenyl)amino)ethyl methanesulfonate (634);

((4-nitro-2-(piperazin-1-ylsulfonyl)phenyl)azanediyl)bis(ethane-2,1-diyl) dimethanesulfonate (640);

((2-((4-methylpiperazin-1-yl)sulfonyl)-4-nitrophenyl)azanediyl)bis(ethane-2,1-diyl) dimethanesulfonate (641);

((2-((4-ethylpiperazin-1-yl)sulfonyl)-4-nitrophenyl)azanediyl)bis(ethane-2,1-diyl) dimethanesulfonate (642);

((2-((4-(2-hydroxyethyl)piperazin-1-yl)sulfonyl)-4-nitrophenyl)azanediyl)bis(ethane-2,1-diyl) dimethanesulfonate (643);

((2-((4-(2,3-dihydroxypropyl)piperazin-1-yl)sulfonyl)-4-nitrophenyl)azanediyl)bis(ethane-2,1-diyl) dimethanesulfonate (644);

((2-((4-methyl-1,4-diazepan-1-yl)sulfonyl)-4-nitrophenyl)azanediyl)bis(ethane-2,1-diyl) dimethanesulfonate (662);

((2-((5-methyl-1,5-diazocan-1-yl)sulfonyl)-4-nitrophenyl)azanediyl)bis(ethane-2,1-diyl) dimethanesulfonate (663);

((2-((1-methylpiperidin-4-yl)sulfonyl)-4-nitrophenyl)azanediyl)bis(ethane-2,1-diyl) dimethanesulfonate (664);

((2-((4-aminopiperidin-1-yl)sulfonyl)-4-nitrophenyl)azanediyl)bis(ethane-2,1-diyl) dimethanesulfonate (665);

((2-((4-(dimethylamino)piperidin-1-yl)sulfonyl)-4-nitrophenyl)azanediyl)bis(ethane-2,1-diyl) dimethanesulfonate (666);

((2-((1-methylazepan-4-yl)sulfonyl)-4-nitrophenyl)azanediyl)bis(ethane-2,1-diyl) dimethanesulfonate (667);

((2-((1-methylazocan-5-yl)sulfonyl)-4-nitrophenyl)azanediyl)bis(ethane-2,1-diyl) dimethanesulfonate (668);

((2-(morpholinosulfonyl)-4-nitrophenyl)azanediyl)bis(ethane-2,1-diyl) dimethanesulfonate (669);

((2-(N-(2-(dimethylamino)ethyl)sulfamoyl)-4-nitrophenyl)azanediyl)bis(ethane-2,1-diyl) dimethanesulfonate (670);

((2-(N-(2-(dimethylamino)ethyl)-N-methylsulfamoyl)-4-nitrophenyl)azanediyl)bis(ethane-2,1-diyl) dimethanesulfonate (671);

((2-(N-(2-morpholinoethyl)sulfamoyl)-4-nitrophenyl)azanediyl)bis(ethane-2,1-diyl) dimethanesulfonate (672);

((2-(N-methyl-N-(2-morpholinoethyl)sulfamoyl)-4-nitrophenyl)azanediyl)bis(ethane-2,1-diyl) dimethanesulfonate (673);

N,N-bis(2-bromoethyl)-2-methyl-4-nitro-6-(piperazin-1-ylsulfonyl)aniline (679);

N,N-bis(2-bromoethyl)-2-methyl-6-((4-methylpiperazin-1-yl)sulfonyl)-4-nitroaniline (680);

N,N-bis(2-bromoethyl)-2-((4-ethylpiperazin-1-yl)sulfonyl)-6-methyl-4-nitroaniline (681);

3-(4-((2-(bis(2-bromoethyl)amino)-3-methyl-5-nitrophenyl)sulfonyl)piperazin-1-yl)propane-1,2-diol (683);

N,N-bis(2-bromoethyl)-2-methyl-6-((4-methyl-1,4-diazepan-1-yl)sulfonyl)-4-nitroaniline (701);

N,N-bis(2-bromoethyl)-2-methyl-6-((5-methyl-1,5-diazocan-1-yl)sulfonyl)-4-nitroaniline (702);

N,N-bis(2-bromoethyl)-2-methyl-6-((1-methylpiperidin-4-yl)sulfonyl)-4-nitroaniline (703);

1-((2-(bis(2-bromoethyl)amino)-3-methyl-5-nitrophenyl)sulfonyl)piperidin-4-amine (704);

1-((2-(bis(2-bromoethyl)amino)-3-methyl-5-nitrophenyl)sulfonyl)-N,N-dimethylpiperidin-4-amine (705);

2-((2-bromoethyl)(2-methyl-4-nitro-6-(piperazin-1-ylsulfonyl)phenyl)amino)ethyl methanesulfonate (718);

2-((2-bromoethyl)(2-methyl-6-((4-methylpiperazin-1-yl)sulfonyl)-4-nitrophenyl)amino)ethyl methanesulfonate (719);

2-((2-bromoethyl)(2-((4-ethylpiperazin-1-yl)sulfonyl)-6-methyl-4-nitrophenyl)amino)ethyl methanesulfonate (720);

2-((2-bromoethyl)(2-((4-(2,3-dihydroxypropyl)piperazin-1-yl)sulfonyl)-6-methyl-4-nitrophenyl)amino)ethyl methanesulfonate (722);

2-((2-bromoethyl)(2-methyl-6-((4-methyl-1,4-diazepan-1-yl)sulfonyl)-4-nitrophenyl)amino)ethyl methanesulfonate (740);

2-((2-bromoethyl)(2-methyl-6-((5-methyl-1,5-diazocan-1-yl)sulfonyl)-4-nitrophenyl)amino)ethyl methanesulfonate (741);

2-((2-bromoethyl)(2-methyl-6-((1-methylpiperidin-4-yl)sulfonyl)-4-nitrophenyl)amino)ethyl methanesulfonate (742);

2-((2-((4-aminopiperidin-1-yl)sulfonyl)-6-methyl-4-nitrophenyl)(2-bromoethyl)amino)ethyl methanesulfonate (743);

2-((2-bromoethyl)(2-((4-(dimethylamino)piperidin-1-yl)sulfonyl)-6-methyl-4-nitrophenyl)amino)ethyl methanesulfonate (744);

((2-methyl-4-nitro-6-(piperazin-1-ylsulfonyl)phenyl)azanediyl)bis(ethane-2,1-diyl) dimethanesulfonate (757);

((2-methyl-6-((4-methylpiperazin-1-yl)sulfonyl)-4-nitrophenyl)azanediyl)bis(ethane-2,1-diyl) dimethanesulfonate (758);

((2-((4-ethylpiperazin-1-yl)sulfonyl)-6-methyl-4-nitrophenyl)azanediyl)bis(ethane-2,1-diyl) dimethanesulfonate (759);

((2-((4-(2,3-dihydroxypropyl)piperazin-1-yl)sulfonyl)-6-methyl-4-nitrophenyl)azanediyl)bis(ethane-2,1-diyl) dimethanesulfonate (761);

((2-methyl-6-((4-methyl-1,4-diazepan-1-yl)sulfonyl)-4-nitrophenyl)azanediyl)bis(ethane-2,1-diyl) dimethanesulfonate (779);

((2-methyl-6-((5-methyl-1,5-diazocan-1-yl)sulfonyl)-4-nitrophenyl)azanediyl)bis(ethane-2,1-diyl) dimethanesulfonate (780);

((2-methyl-6-((1-methylpiperidin-4-yl)sulfonyl)-4-nitrophenyl)azanediyl)bis(ethane-2,1-diyl) dimethanesulfonate (781);

((2-((4-aminopiperidin-1-yl)sulfonyl)-6-methyl-4-nitrophenyl)azanediyl)bis(ethane-2,1-diyl) dimethanesulfonate (782);

((2-((4-(dimethylamino)piperidin-1-yl)sulfonyl)-6-methyl-4-nitrophenyl)azanediyl)bis(ethane-2,1-diyl) dimethanesulfonate (783);

2-((2-bromoethyl)(4-nitro-2-(piperazin-1-ylsulfonyl)-6-(trifluoromethyl)phenyl)amino)ethyl methanesulfonate (952);

2-((2-bromoethyl)(2-((4-methylpiperazin-1-yl)sulfonyl)-4-nitro-6-(trifluoromethyl)phenyl)amino)ethyl methanesulfonate (953);

2-((2-bromoethyl)(2-((4-ethylpiperazin-1-yl)sulfonyl)-4-nitro-6-(trifluoromethyl)phenyl)amino)ethyl methanesulfonate (954);

2-((2-bromoethyl)(2-((4-(2,3-dihydroxypropyl)piperazin-1-yl)sulfonyl)-4-nitro-6-(trifluoromethyl)phenyl)amino)ethyl methanesulfonate (956);

2-((2-bromoethyl)(2-((4-methyl-1,4-diazepan-1-yl)sulfonyl)-4-nitro-6-(trifluoromethyl)phenyl)amino)ethyl methanesulfonate (974);

2-((2-bromoethyl)(2-((5-methyl-1,5-diazocan-1-yl)sulfonyl)-4-nitro-6-(trifluoromethyl)phenyl)amino)ethyl methanesulfonate (975);

2-((2-((4-aminopiperidin-1-yl)sulfonyl)-4-nitro-6-(trifluoromethyl)phenyl)(2-bromoethyl)amino)ethyl methanesulfonate (977);

2-((2-bromoethyl)(2-((4-(dimethylamino)piperidin-1-yl)sulfonyl)-4-nitro-6-(trifluoromethyl)phenyl)amino)ethyl methanesulfonate (978);

((4-nitro-2-(piperazin-1-ylsulfonyl)-6-(trifluoromethyl)phenyl)azanediyl)bis(ethane-2,1-diyl) dimethanesulfonate (991);

((2-((4-methylpiperazin-1-yl)sulfonyl)-4-nitro-6-(trifluoromethyl)phenyl)azanediyl)bis(ethane-2,1-diyl) dimethanesulfonate (992);

((2-((4-ethylpiperazin-1-yl)sulfonyl)-4-nitro-6-(trifluoromethyl)phenyl)azanediyl)bis(ethane-2,1-diyl) dimethanesulfonate (993);

((2-((4-(2,3-dihydroxypropyl)piperazin-1-yl)sulfonyl)-4-nitro-6-(trifluoromethyl)phenyl)azanediyl)bis(ethane-2,1-diyl) dimethanesulfonate (995);

((2-((4-methyl-1,4-diazepan-1-yl)sulfonyl)-4-nitro-6-(trifluoromethyl)phenyl)azanediyl)bis(ethane-2,1-diyl) dimethanesulfonate (1013);

((2-((5-methyl-1,5-diazocan-1-yl)sulfonyl)-4-nitro-6-(trifluoromethyl)phenyl)azanediyl)bis(ethane-2,1-diyl) dimethanesulfonate (1014);

((2-((4-aminopiperidin-1-yl)sulfonyl)-4-nitro-6-(trifluoromethyl)phenyl)azanediyl)bis(ethane-2,1-diyl) dimethanesulfonate (1016);

((2-((4-(dimethylamino)piperidin-1-yl)sulfonyl)-4-nitro-6-(trifluoromethyl)phenyl)azanediyl)bis(ethane-2,1-diyl) dimethanesulfonate (1017);

2-((2-bromoethyl)(2-ethynyl-4-nitro-6-(piperazin-1-ylsulfonyl)phenyl)amino)ethyl methanesulfonate (1069);

2-((2-bromoethyl)(2-ethynyl-6-((4-methylpiperazin-1-yl)sulfonyl)-4-nitrophenyl)amino)ethyl methanesulfonate (1070);

2-((2-bromoethyl)(2-((4-ethylpiperazin-1-yl)sulfonyl)-6-ethynyl-4-nitrophenyl)amino)ethyl methanesulfonate (1071);

((2-ethynyl-4-nitro-6-(piperazin-1-ylsulfonyl)phenyl)azanediyl)bis(ethane-2,1-diyl) dimethanesulfonate (1108);

((2-ethynyl-6-((4-methylpiperazin-1-yl)sulfonyl)-4-nitrophenyl)azanediyl)bis(ethane-2,1-diyl) dimethanesulfonate (1109);

((2-((4-ethylpiperazin-1-yl)sulfonyl)-6-ethynyl-4-nitrophenyl)azanediyl)bis(ethane-2,1-diyl) dimethanesulfonate (1110);

4-((2-(bis(2-((methylsulfonyl)oxy)ethyl)amino)-5-nitrophenyl)sulfonyl)piperazin-1-ium methanesulfonate (640.Ms);

4-((2-(bis(2-((methylsulfonyl)oxy)ethyl)amino)-5-nitrophenyl)sulfonyl)-1-methylpiperazin-1-ium methanesulfonate (641.Ms);

4-((2-(bis(2-((methylsulfonyl)oxy)ethyl)amino)-5-nitrophenyl)sulfonyl)-1-ethylpiperazin-1-ium methanesulfonate (642.Ms);

4-((2-(bis(2-((methylsulfonyl)oxy)ethyl)amino)-5-nitrophenyl)sulfonyl)-1-(2-hydroxyethyl)piperazin-1-ium methanesulfonate (643.Ms);

4-((2-(bis(2-((methylsulfonyl)oxy)ethyl)amino)-5-nitrophenyl)sulfonyl)-1-(2,3-dihydroxypropyl)piperazin-1-ium methanesulfonate (644.Ms);

4-((2-(bis(2-((methylsulfonyl)oxy)ethyl)amino)-3-methyl-5-nitrophenyl)sulfonyl)piperazin-1-ium methanesulfonate (757.Ms);

4-((2-(bis(2-((methylsulfonyl)oxy)ethyl)amino)-3-methyl-5-nitrophenyl)sulfonyl)-1-methylpiperazin-1-ium methanesulfonate (758.Ms);

4-((2-(bis(2-((methylsulfonyl)oxy)ethyl)amino)-5-nitro-3-(trifluoromethyl)phenyl)sulfonyl)piperazin-1-ium methanesulfonate (991.Ms);

4-((2-(bis(2-((methylsulfonyl)oxy)ethyl)amino)-5-nitro-3-(trifluoromethyl)phenyl)sulfonyl)-1-methylpiperazin-1-ium methanesulfonate (992.Ms);

4-((2-(bis(2-((methylsulfonyl)oxy)ethyl)amino)-3-ethynyl-5-nitrophenyl)sulfonyl)piperazin-1-ium methanesulfonate (1108.Ms); and 4-((2-(bis(2-((methylsulfonyl)oxy)ethyl)amino)-3-ethynyl-5-nitrophenyl)sulfonyl)-1-methylpiperazin-1-ium methanesulfonate (1109.Ms).

6. A compound as claimed in claim 1 which has the formula:

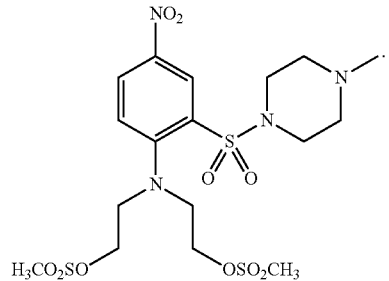

7. A compound as claimed in claim 1 which has the formula:

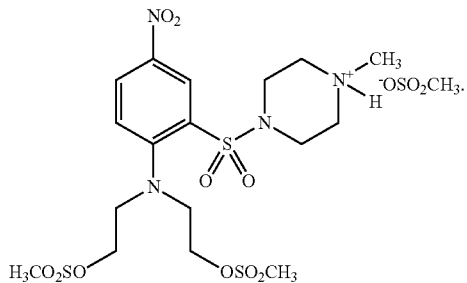

8. A compound as claimed in claim 1, wherein the pharmaceutically acceptable salt is a mesylate salt.

9. A pharmaceutical composition comprising a compound of claim 1 together with a pharmaceutically acceptable carrier.

10. A method of treating a hyperproliferative disorder comprising administering to a person a compound of claim 1.

11. A method as claimed in claim 10, wherein the hyperproliferative disorder is characterised by association with the formation of neoplasms that express a detectable amount of AKR1C3.

12. A method as claimed in claim 10, wherein the hyperproliferative disorder is cancer.

13. A method as claimed in claim 12, wherein the cancer is acute myeloid leukaemia, T-cell lineage acute lymphocytic leukaemia (T-ALL), chronic myeloid leukaemia (CML), hepatocellular carcinoma, non-muscle-invasive (superficial) bladder cancer, locally invasive bladder cancer, metastatic bladder cancer, gastric cancer, cervical cancer, pancreatic cancer, colon cancer, rectal cancer, oesophageal cancer, head and neck cancer, ovarian cancer, glioblastoma, sarcoma, endometrial cancer, prostate cancer, renal cancer or lung cancer.

14. A method of cell ablation comprising the steps:
   a. activating a compound of claim 1 with at least one AKR1C3 enzyme to produce a cytotoxic metabolite capable of ablating a target cell; and
   b. contacting the target cell with the cytotoxic metabolite to ablate the cell.

15. A method as claimed in claim 10, wherein the compound is:

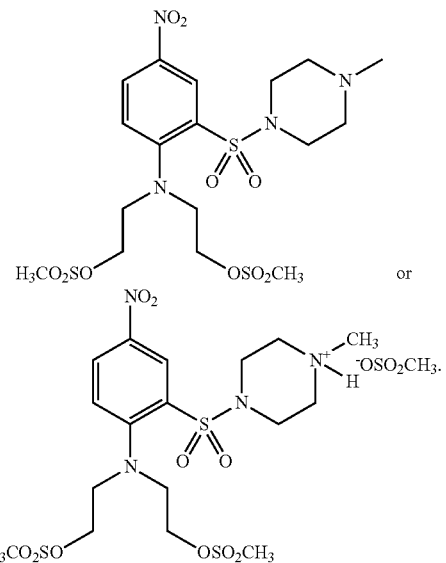

* * * * *